United States Patent [19]

Baldwin et al.

[11] Patent Number: 4,916,223

[45] Date of Patent: Apr. 10, 1990

[54] SUBSTITUTED HEXAHYDROARYLQUINOLIZINES

[75] Inventors: John J. Baldwin, Gwynedd Valley; Joel R. Huff, Lederach; Susan J. DeSolms, Norristown; Joseph P. Vacca, Telford, all of Pa.; Jonathan M. Wiggins, Lafayette, Ind.; Steven D. Young, Lansdale, Pa.

[73] Assignee: Merck & Co., Inc., Rahway, N.J.

[21] Appl. No.: 306,138

[22] Filed: Feb. 6, 1989

Related U.S. Application Data

[63] Continuation-in-part of Ser. No. 76,495, Jul. 27, 1987, Pat. No. 4,831,035, which is a continuation-in-part of Ser. No. 901,485, Aug. 28, 1986, abandoned.

[51] Int. Cl.$^4$ .................. A61K 31/505; C07D 495/20
[52] U.S. Cl. ..................................................... 544/231
[58] Field of Search ........................... 546/18; 544/231

[56] References Cited

U.S. PATENT DOCUMENTS 4,831,035  5/1989  Baldwin et al. ...................... 546/18

Primary Examiner—Robert T. Bond
Attorney, Agent, or Firm—Alice O. Robertson; Joseph F. DiPrima

[57] ABSTRACT

Certain substituted hexahydroarylquinolizines and pharmaceutically acceptable salts thereof are peripherally selective $\alpha_2$-adrenoceptor antagonists. The compounds are adapted to be employed for the treatment of certain pathological disorders such as hypertension, diabetes, disorders involving platelet aggregation and the like without side effects attributable to effect on the central nervous system.

2 Claims, No Drawings

SUBSTITUTED HEXAHYDROARYLQUINOLIZINES

This is a continuation-in-part of copending application Ser. No. 76,495, filed Jul. 27, 1987, now U.S. Pat. No. 4,831,035, which in turn is a continuation-in-part of copending application Ser. No. 901,485, filed Aug. 28, 1986, now abandoned.

BACKGROUND OF THE INVENTION

Peripheral $\alpha_2$-adrenoceptors are associated with a variety of important physiological effects. Vascular $\alpha_2$-adrenoceptors when stimulated mediate vasoconstriction which gives rise to hypertension. Pancreatic $\alpha_2$-adrenoceptors modulate release of insulin. Platelet $\alpha_2$-adrenoceptors when activated cause platelet aggregation. Other $\alpha_2$-adrenoceptors affect gastrointestinal motility and fat cell metabolism. Molecules which selectively antagonize these peripheral $\alpha_2$-adrenoceptors offer a novel approach to the treatment of pathological conditions such as hypertension, diabetes, obesity, and disorders involving platelet aggregation and gas gastrointestinal motility.

$\alpha_2$-Adrenoceptors are located also in the central nervous system and mediate a variety of other physilogical effects such as respiratory stimulation, psychomotor activity, increase in wakefulness and reduction in appetite.

Various compounds have been reported which affect $\alpha_2$-adrenoceptor activity. Thus, for example, certain benzoquinolizines have been reported in UK patent applications 1435573, 2106909 and 2136804 to posses $\alpha_2$-adrenoceptor antagonistic activity. Generally, however, the $\alpha_2$-adrenoceptor antagonistic activity shown by most of the known compounds are non-selective, i.e., the compounds have a mediating effect on both central and peripheral $\alpha$-antagonistic activity.

SUMMARY OF THE INVENTION

According to the present invention it has been discovered that certain substituted hexahydroarylquinolizines are selective peripheral $\alpha_2$-adrenoceptor antagonists, i.e., they have $\alpha_2$-adrenoceptor blocking activity but are further characterized by tending not to penetrate the blood brain barrier. Thus, the novel compounds are adapted to be employed in the treatment of conditions where selective antagonisms of peripheral $\alpha_2$-adrenoceptors is desirable, such as antihypertensives, antidiabetic agents, anti-obesity agents, platelet aggregation inhibtors, modifiers of gastrointestinal motility and the like. The invention also relates to methods for antagonizing peripheral $\alpha_2$-adrenoceptors and to compositions for carrying out the methods.

DETAILED DESCRIPTION OF THE INVENTION

This invention is concerned with a hexahydroarylquinolizine compound of the formula:

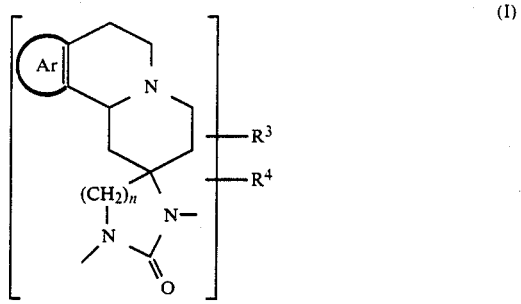

or a pharmaceutically acceptable salt thereof, wherein Ar is an aromatic ring system selected from

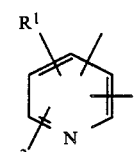

$R^1,R^2$-pyridino-

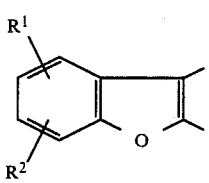

$R^1,R^2$-benzofuro-

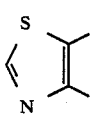

thiazolo-

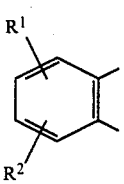

$R^1,R^2$-benzo-

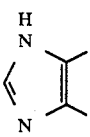

imidazo-

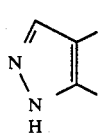

pyrazolo-

-continued

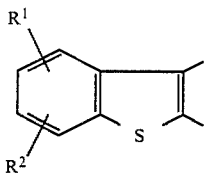

$R^1,R^2$-benzothieno-

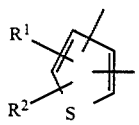

$R^1,R^2$-thieno-

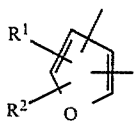

$R^1,R^2$-furo-

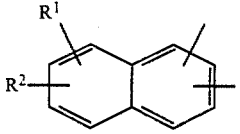

$R^1,R^2$-naptho-

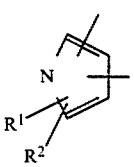

$R^1,R^2$-pyrrolo-

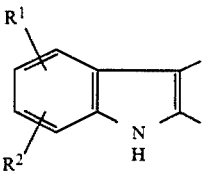

$R^1,R^2$-indolowherein $R^1$ and $R^2$ are indenpendently hydrogen, halo, hydroxy, $C_{1-3}$ alkoxy or lower alkyl, carboxy, or together are methylenedioxy or $C_{3-4}$ alkylene; and wherein the free bonds of Ar may be attached to the quinolizine ring in either configuration of Ar;

$R^3$ is attached to the free bond of one of the nitrogens and is hydrogen, lower alkyl, benzyl or R;

$R^4$ is attached to the free bond of the other nitrogen and is -alkylene-OXR,

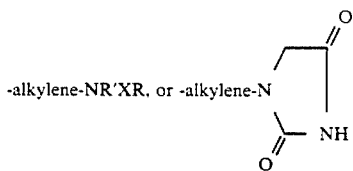

-alkylene-NR'XR, or -alkylene-N wherein R is lower alkyl, $C_1$-$C_3$ alkoxy, phenyl, halophenyl, lower alkylphenyl, lower alkoxyphenyl, benzyl, trifluoromethyl, amino or di(lower alkyl)amino; R' is H or lower alkyl; and X is —CO—, —SO$_2$—, —P(O)(OR')$_2$, —SCNH—, —CONH, or —C(NCN); and n is 1–2.

The compounds have a reduced quinolizine ring and are therefore hexahydroquinolizines. However, the expression "octahydro" may be embraced in the nomenclature of compounds in which n is 2; this reflects the reduced pyrimidine ring.

By the expression "lower alkyl" as herein employed is meant preferably a branched or straight chain alkyl group having from 1 to 6 carbon atoms, inclusive. By the expression "alkylene" is meant a straight, branched, or cyclic chain of the designated carbon content or from 2 to 6 carbon atoms where not specifically designated. By the expression "halo" is meant preferably bromo, chloro, or fluoro.

The pharmaceutically acceptable salts coming within the purview of this invention include the pharmaceutically acceptable acid addition salts. Acids useful for preparing these acid addition salts include, inter alia, inorganic acids, such as the hydrohalic acids (e.g., hydrochloric and hydrobromic acids), sulfuric acid, nitric acid, and phosphoric acid, and organic acids such as maleic, fumaric, tartaric, citric, acetic, benzoic, 2-acetoxybenzoic, salicylic, succinic, p-aminobenzoic, p-acetamidobenzoic, methanesulfonic, or ethanedisulfonic acid, theophylline and 8-chlorotheophylline.

In a preferred embodiment of the present invention, Ar is $R^1,R^2$-benzo[b]furo-, $R^1,R^2$-benzo, $R^1,R^2$-benzo[b]thiono or $R^1$, $R^2$-naphtho, more preferably $R^1,R^2$-benzo[b]furo or $R^1$, $R^2$-benzo, $R^3$ is hydrogen, and $R^4$ is 2-alkanesulfonamidoalkyl.

In a more preferred embodiment, Ar is $R^1$, $R^2$-benzo wherein $R^1$ is 9-methoxy and $R^2$ is hydrogen; $R^3$ is hydrogen; and $R^4$ is 2-methanesulfonamidoethyl.

In another more preferred embodiment, Ar is $R^1,R^2$-benzo[b]thieno, $R^1,R^2$ and $R^3$ are hydrogen and $R^4$ is 2-methanesulfonamidoethyl.

In the most preferred embodiment, Ar is $R^1,R^2$-benzofuro and $R^1$, $R^2$, and $R^3$ are hydrogen, and $R^4$ is 2-methanesulfonamidoethyl.

The compounds of the present invention are solids. Those compounds which are bases are soluble in most inert organic solvents; those which are salts are soluble in polar solvents.

The novel compounds of this invention are described herein as having a configuration such that the hetero atom in the spiro-4-imidazolidin-2-one or spiro-4-(5,6-dhydro-1H-pyrimidin-2-[3H]-one) attached to carbon 2 of the quinolizine ring and the hydrogen at 12b of the quinolizine ring are trans,

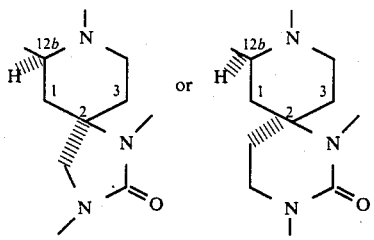

While the trans configuration is the more preferred isomer for $\alpha_2$-adrenoceptor blockade activity hereinafter detailed, the cis isomers are also active and are considered to be within the scope of the present invention. Each of these configurational isomers are racemates capable of being resolved into dextrorotatory and levorotatory enantiomers. The present invention includes pure enantiomers, racemates and mixtures of isomers, and when the compound is named without designation as to a specific isomer or to a racemic mixture or to a specific mixture of isomers, it is intended to be a generic designation embracing all isomers and mixtures of isomers, including unequal mixtures of enantiomers or other isomers.

The compounds of Formula I both as enantiomers, as mixtures of enantiomers, and as acid addition salts are highly effective in selectively antagonizing $\alpha_2$-adrenergic rceptors. Thus, the compounds and the pharmaceutical compositions of the present invention may be used as selective peripheral $\alpha_2$-adrenergic receptor antagonists in the treatment of hypertension, diabetes, platelet aggregation, obesity and gastrointestinal motility dysfunction.

The present invention also embraces a method of treating pathological conditions attributable to undesirable $\alpha$-adrenoceptor activity which comprises administering to subjects with such a condition, a therapeutically effective amount of the hexahydroarylquinolizine compound of Formula I or a pharmaceutically acceptable acid addition salt thereof, or compositions containing said compound.

The present invention further embraces compositions comprising a hexahydroarylquinolizine compound of Formula I or salt thereof, alone or in combination for the purpose of carrying out the method of treatment in accordance with the present invention.

Compounds of Formula I in which $R^4$ is -alkyleneOXR and represented by the formula:

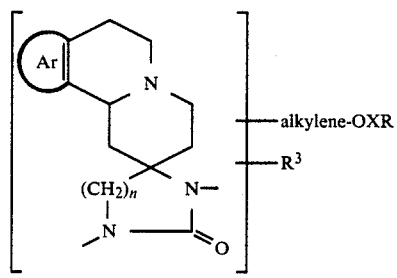

(IA)

may be further classified as follows:

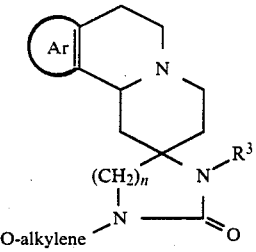

(IA-1)

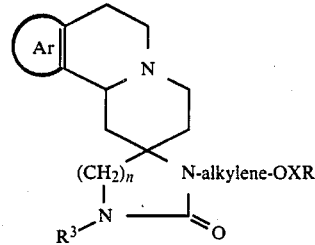

(IA-2)

The compounds of Formula IA may be prepared by the reaction of a hydroxyalkyl compound of Formula II:

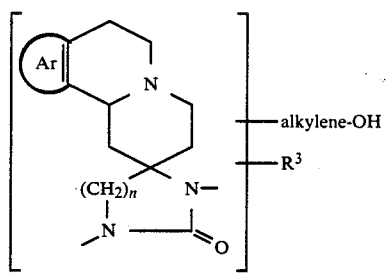

(II)

with an acid chloride:

RXCl    (III)

provided that when $R^3$ is an alkyl group substituted on the 1'-nitrogen, (nitrogen not attached to the spiro carbon), and n is 1, then the alkyl group is introduced by alkylating the corresponding IA compound in which $R^3$ is H.

In carrying out this reaction, the hydroxyalkyl compound of Formula II and an appropriate acid chloride of Formula III are stirred together in an inert solvent such as acetonitrile or chloroform with an organic base or in a basic organic solvent at ambient temperature for time sufficient for the reaction to take place with the formation of the ester compound in the reaction mixture. At the end of the reaction period, the solvent is removed under reduced pressure to obtain a residue. The residue is partitioned between water and chloroform to separate the ester compound and the salt formed between hydrogen chloride and base or basic solvent. The chloroform solution is then dried and the solvent vaporized from the dried solution to recover the ester compound of Formula IA.

In the reaction, the acid halide is employed in molar excess. Generally about 1-2 moles of RXCl is employed for each mole of hydroxyalkyl compound (II). The reaction medium is preferably methylene chloride with an organic base such as triethylamine, diisopropylethylamine, pyridine, collidine, picoline and the like which can bind the hydrogen chloride by-product.

The reactant hydroxyalkyl compound of Formula II may be obtained by a method hereinafter described but more fully described and claimed in copending applications Ser. No. 740,609, filed Jun. 3, 1985 in the name of J. J. Baldwin et al., now abandoned, and Ser. No. 848,262, filed Apr. 4, 1986 in the name of J. J. Baldwin et al., now U.S. Pat. No. 4,710,504, Dec. 1, 1987, which are incorporated by reference.

The reactants RXCl are readily available organic reagents or may be easily formed from readily available chemical reagents.

In preparing the compounds of the formula IA in which $R^3$ is an alkyl substituted on the 1'-nitrogen and n is 1, a compound in which $R^3$ is H and represent by

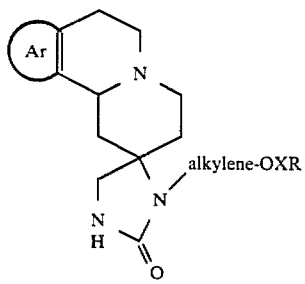

(IA')

may be contacted with an alkyl halide in a vigorously stirred mixture of inert organic solvent, and phase transfer catalyst in aqueous alkali for time sufficient for reaction to take place with the formation of

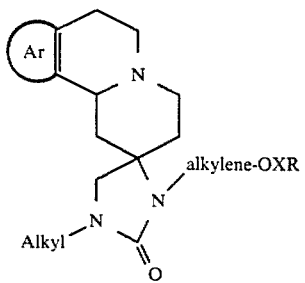

(IA'')

and the latter recovered from the reaction mixture employing conventional procedures.

Compounds of Formula I in which $R^4$ is alkylene-NR'XR and represented by the formula:

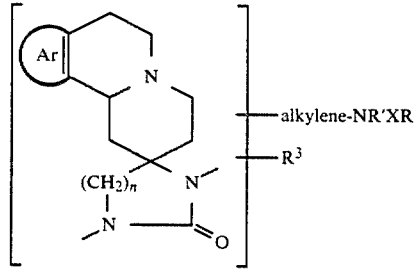

(IB)

may be further classified as follows:

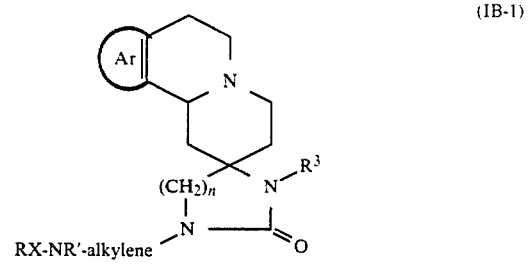

(IB-1)

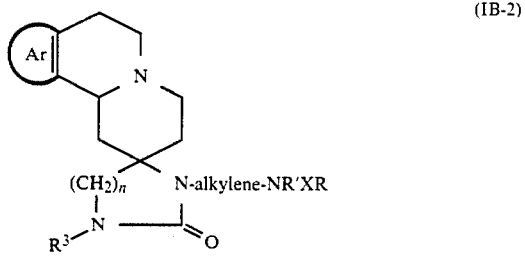

(IB-2)

The compounds in which R' is H may be prepared by a series of reactions in which the compound of Formula IA is a starting material as follow:

$$(IA) \xrightarrow{NaN_3}$$

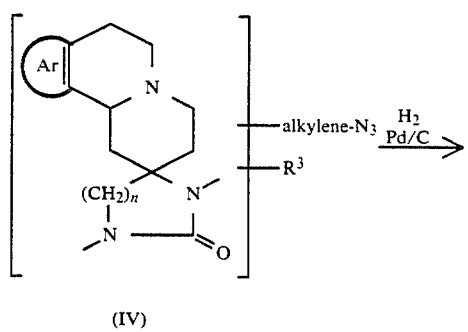

(IV)

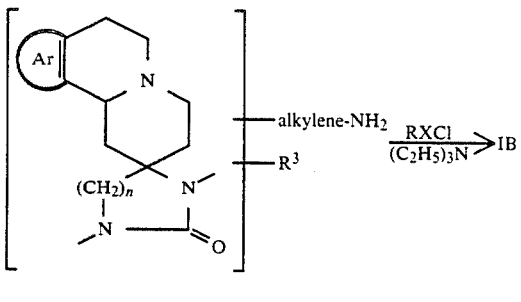

(V)

In carrying out the first step, sodium azide is added to a solution of the ester compound (IA) in an inert solvent and the mixture is heated preferably in the range of 90°–100° C. for several hours to obtain an azidoalkyl compound (IV) in the reaction mixture. The mixture is cooled to ambient temperature, then added to ice water and the azido alkyl compound recovered employing conventional procedures.

In the next step, the azidoalkyl intermediate (IV) is catalytically hydrogenated to the aminoalkyl compound (V). The reaction is carried out in a low pressure hydrogenation apparatus in alcohol solvent in the presence of palladium on carbon catalyst. The reaction is complete in several hours with the formation of the aminoalkyl compound. At the end of this period, the catalyst is removed by filtration and the solvent evaporated to obtain the aminoalkyl compound as residue.

In the next step, the aminoalkyl compound (V) is acylated with an acid chloride, RXCl (III). The reaction is carried out by adding the acid chloride to a solution of aminoalkyl compound and a tertiary amine in an inert solvent, and RXCl added thereto portionwise and with cooling while the temperature is maintained at about 0° C. to produce the acylated aminoalkyl compound (IB) in the reaction mixture. After completion of the addition, the reaction mixture is allowed to warm up to ambient temperature and then partitioned between water and methylene chloride. The organic layer containing compound IB is separated, washesd, dried, the solvent then evaporated employing conventional procedures to recover the desired product of Formula IB where R' is H.

Alternatively, the compounds of Formula IB may be prepared from a compound of Formula IA by reacting said compound with an acid amide RXNH$_2$ thereby directly substituting an amide group for the ester group in Formula IA. The process may be carried out by adding an appropriate imidazolidinone ester of Formula IA and an acid amide RXNH$_2$ to a slurry of potassium hydride in inert solvent and stirring and heating the mixture in a temperature range of about 70° to 90° C. to obtain the amide product of Formula IB. The latter then may be recovered and purified employing conventional procedures.

The compound also may be obtained from a quinolizin-2-one (VI) without prior ester formation as subsequently described.

When R' is lower alkyl, the product thus obtained may be alkylated employing conventional procedures. Since the 1'-nitrogen is also susceptible to alkylation, it is necessary to avoid using excess alkylating agent.

Compounds of the formula IB in which R$^3$ is an alkyl substituted on the 1'-nitrogen and n is 1, may be prepared by an alternative method of alkylating a compound represented by

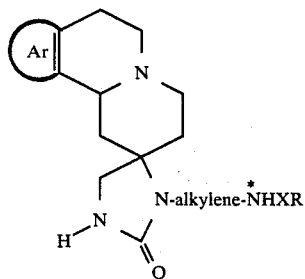

(IB')

However, in view of the hydrogen on the amido nitrogen, the alkylation is carried out after first protecting the amido nitrogen. This may be carried out by forming a lithium derivative of (IB') by reacting same with n-butyl lithium in the cold and thereafter adding chloromethyl benzyl ether in the cold and stirring together to form an N*-benzyloxymethyl derivative which after recovery by conventional procedures may be alkylated by conventional means, in the manner previously described.

The starting material (Formula II) may be prepared from a quinolizin-2-one (VI):

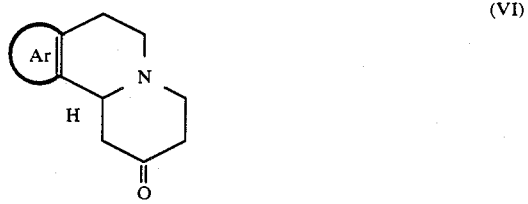

The particular sequence of reactions to be followed depends on whether the hydroxyalkyl group is on the nitrogen attached to the spiro carbon or on the more remote nitrogen. The sequence also depends on whether the ring is an imidazolidinone or a diazinone ring.

(A) When the compound of Formula II is represented by:

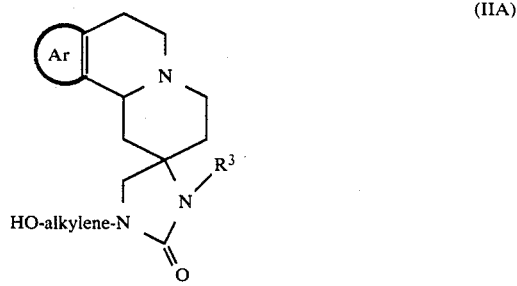

it may be prepared through the following series of reactions:

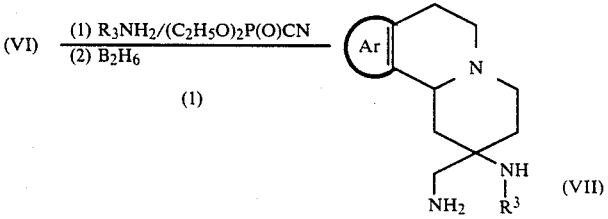

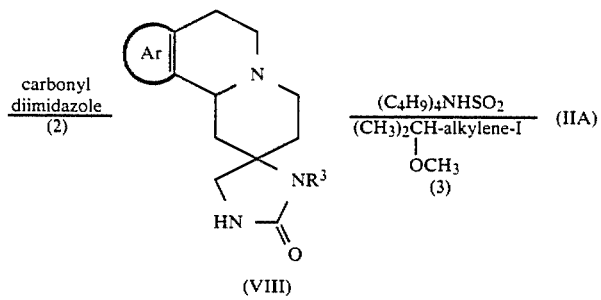

As the first step in carrying out the sequence of reactions for the preparation of the compound of Formula IIA, diethyl cyanophosphonate is added to a solution of quinolizin-2-one (VI) in dry ethereal solvent, such as tetrahydrofuran, previously saturated at 0° C. with alkylamine, the mixture is stirred for at least several hours, conveniently overnight, and the solvent then is vaporized to obtain an aminonitrile intermediate. The latter is dissolved in tetrahydrofuran and to it is added a solution of 1M borane in tetrahydrofuran and the resulting mixture heated at reflux temperature for 10 to 24 hours. The reaction mixture is then cooled, methanol is slowly added thereto to quench the reaction, followed by 6N hydrochloric acid and the resulting mixture refluxed for several hours to obtain 2-aminomethyl 2-alkylamino substituted quinolizine intermediate (VII) in the reaction mixture as the hydrochloride salt. The desired substituted quinolizine (VII) may be recovered by basifying the reaction mixture with saturated sodium carbonate solution, extracting the product therefrom with an inert solvent such as chloroform, purifying and separating the enantiomorphs by medium pressure column chromatography (employing chloroform saturated with ammonia as eluant).

In the second step, 1,1'-carbonyldiimidazole is added to a solution of a 2-aminomethyl 2-alkylamino-substituted-quinolizine in an inert organic solvent such as toluene and the resulting mixture stirred at ambient temperature to 50° C. for several hours to obtain a quinolizin-imidazolidinone compound (VIII) in the reaction mixture. The latter then may be recovered and purified employing conventional procedures.

In the third step of hydroxyalkylating the nitrogen, the reagent for such alkylation is first prepared. The preferred reagent, 2-methoxy-2-(ω-iodoalkoxy)propane, is readily prepared by adding ω-iodoalkanol and a drop of phosphorous oxychloride to cold (0° C.) methoxypropene, stirring for about one hour, then adding a solid base such as potassium carbonate, separating the liquid and concentrating to obtain the iodoalkoxypropane reagent as residue.

The iodoalkoxypropane reagent is added with vigorous stirring to a solution of the imidazolidinone compound (VIII) in toluene to which previously had been added tetrabutylammonium hydrogen sulfate and 40 percent sodium hydroxide. After completion of the addition the reaction mixture is stirred for from 20 to 50 hours, and the organic layer then poured into and intimately admixed with 5 percent hydrochloric acid solution, then the mixture made basic. The organic layer separated and the desired hydroxyalkyl compound (IIA) recovered employing conventional procedures and purified by chromatographing on silica gel and eluting with ammonia saturated chloroform.

(B) When the compound of Formula II is represented by (IIB)

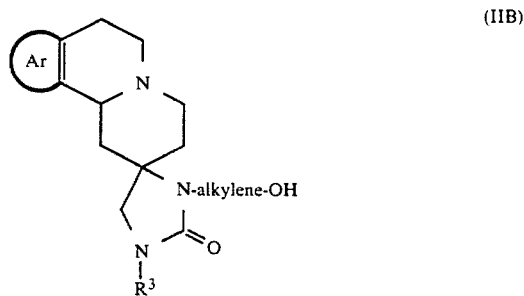

where $R^3$ is H, it may be prepared through the following series of reactions:

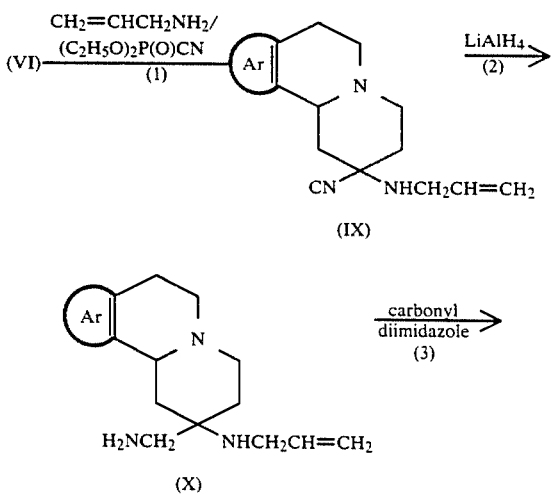

-continued

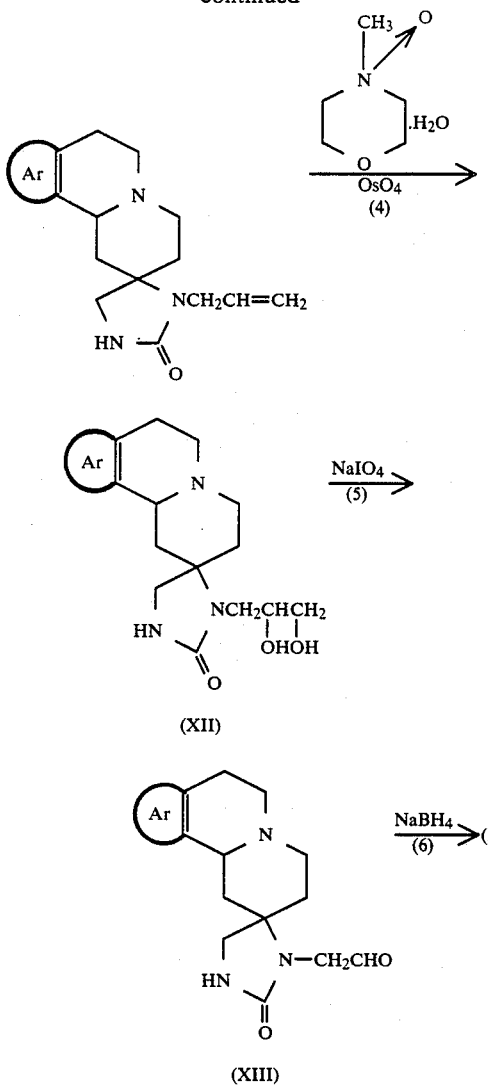

As the first step in carrying out the sequence of reactions for the preparation of the compounds of Formula IIB when $R^3$ is H and m is 2, about a two-molar excess of allylamine and then about a two-molar excess of diethyl cyanophosphonate are added to a solution of a quinolizin-2-one compound (VI) in tetrahydrofuran. The mixture is stirred at ambient temperature for several hours to complete the reaction, and then concentrated to recover a residue which is purified conveniently by low pressure chromatography, preferably on silica gel using ammonia saturated chloroform or methanol/ethylacetate as eluant, to recover 2-cyano-2-(2-propenylamino)quinolizine intermediate (IX).

In the second step, a solution of the quinolizine intermediate IX in tetrahydrofuran is added to a cooled to 0° C. solution of lithium aluminum hydride in ether and the resulting mixture stirred for 1 to 2 hours. At the end of this period, the reaction is quenched with water, and the intermediate 2-aminomethyl-2-(2-propenylamino)-quinolizine compound (X) recovered by conventional procedures.

In the third step, 1,1'-carbonyldiimidazole is added to a solution of the 2-aminomethyl-2-(2-propenylamino)-quinolizine intermediate in an inert solvent such as methylene chloride and the mixture allowed to react at ambient temperature for several hours after which time the product is recovered from the reaction mixture by washing, drying the organic solution and vaporizing the solvent to obtain the imidazolidinone intermediate (XI) as residue.

In the fourth step, a 0.4M solution of osmium tetroxide (0.05 mole for each mole of XI) is added dropwise to a solution in tetrahydrofuran of the intermediate (XI) and 4-methylmorpholine-4-oxide monohydrate (two moles for each mole of intermediate) and the resulting mixture stirred for 16 to 20 hours to obtain the 3-(2,3-dihydroxypropyl)imidazolidinone intermediate (XII) in the reaction mixture which may then be recovered employing conventional procedures.

In the next step, an aqueous solution of sodium periodate is added dropwise to a cooled to 0° C. solution of the 3-(2,3-dihydroxypropyl)imidazolidin-2-one (XII) and 20 percent sodium hydroxide in 95 percent ethanol (3 moles of sodium periodate for each mole of XII) and the resulting mixture stirred for several hours at 0° C. to obtain in the reaction mixture the aldehyde intermediate (XIII). The solvent is removed by vaporization and the residue partitioned between water and chloroform, the organic layer separated and dried, and the solvent vaporized to recover the aldehyde intermediate (XIII) which is immediately dissolved in absolute ethanol for use in the reduction step.

In the reduction, a large molar excess of sodium borohydride is added to the ethanolic solution of the aldehyde intermediate and the mixture stirred for about 16 to 24 hours. At the end of this period, the solvent is vaporized and the residue recovered in an organic solvent. The resulting solution is washed and dried, and the solvent vaporized to obtain the desired 2-hydroxyethyl compound of Formula IIB where $R^3$ is H.

When in the compound of Formula IIB, $R^3$ is H and the alkylene chain is greater than ethylene, the compound may be prepared through a similar series of reactions except that $CH_2=CH(CH_2)_{m+1}NH_2$ where m is 1 to 4 is substituted for allylamine.

(C) When the compound of Formula II is represented by:

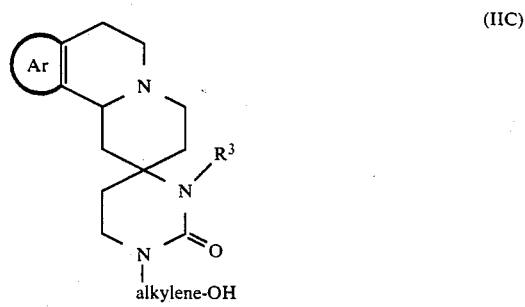

and alkylene is ethylene, it may be prepared through the following series of reactions:

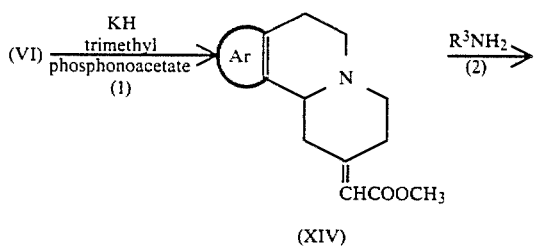

(XIV)

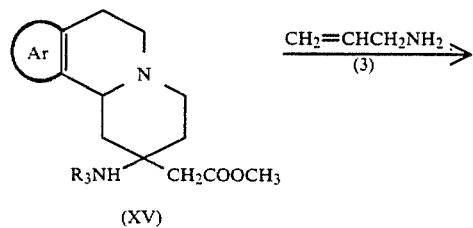

(XV)

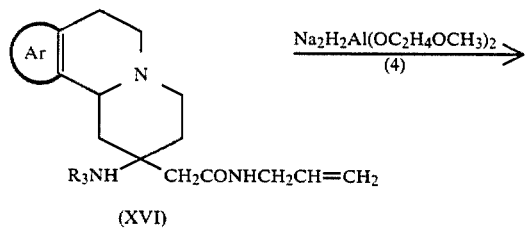

(XVI)

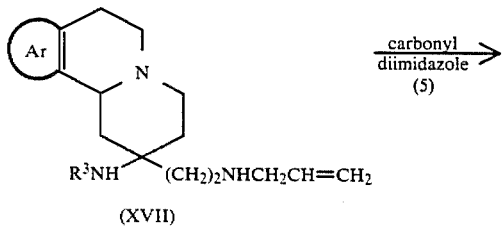

(XVII)

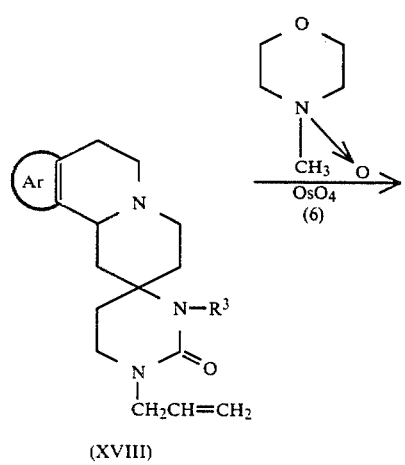

(XVIII)

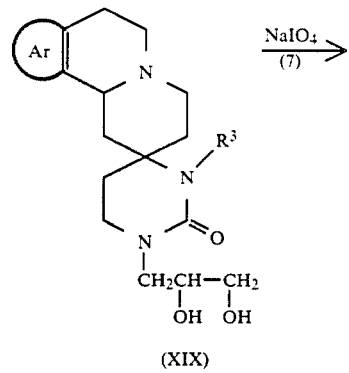

(XIX)

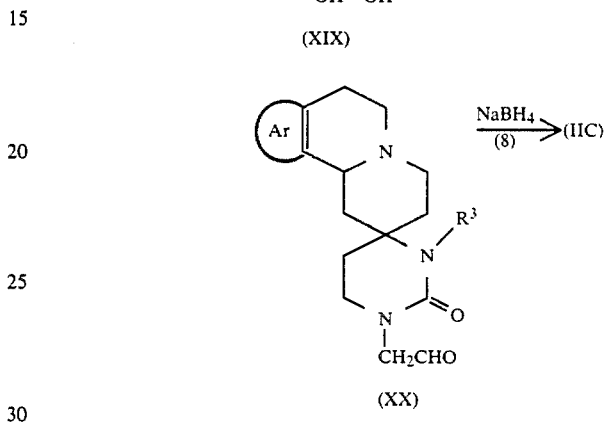

(XX)

As the first step in carrying out the sequence of reactions for the preparation of the compounds of Formula IIC, a solution of a quinolizin-2-one compound of Formula VI in dry tetrahydrofuran is added to a cooled to 0° C. stirred suspension of potassium hydride in tetrahydrofuran under argon to which has been added trimethyl phosphonoacetate and stirred for several minutes to obtain a viscous mixture. The cooling bath is removed and stirring continued for 10 to 20 hours to obtain a carbomethoxymethylidene derivative of quinolizine (XIV) in the reaction mixture. The product may be recovered from the reaction mixture by diluting with water, extracting with ethyl acetate, drying and vaporizing the solvent. The carbomethoxymethylidene intermediate may be purified by chromatographing on silica gel using ethyl acetate/hexane mixture as eluant.

In the second step, a solution of the carbomethoxymethylidene intermediate (XIV) in ethanol at −78° C. and alkylamine are placed in a pressure vessel fitted with stirring means and the mixture stirred at room temperature for several hours to obtain a methyl 2-methylaminoquinolizin-2-ylacetate intermediate (XV) in the reaction mixture. The latter then may be recovered by releasing the pressure and removing the solvent in vacuo.

In the third step, a mixture of the acetate intermediate (XV) and allylamine in absolute ethanol are heated together at reflux temperature for several days to obtain an N-(2-propenyl)acetamide intermediate (XVI) in the reaction mixture. The latter may be recovered by conventional means and purified by pressure column chromatography, preferably, employing ammonia saturated chloroform as eluant.

In the fourth step, a solution of the N-(2-propenyl)acetamide intermediate XVI in tetrahydrofuran is added dropwise to a refluxing mixture of sodium bis(2-methoxyethoxy)aluminum hydride in toluene and dry tetrahydrofuran and the heating continued for several hours to obtain a 2-(propenylamino)ethyl intermediate (XVII) in the reaction mixture. At the end of this period the reaction is quenched by the dropwise addition of a saturated potassium tartrate solution, the solvent then removed and the residue partitioned between water and chlorofrom, and the desired intermediate of Formula XVII recovered by conventional procedures.

In the fifth step, the intermediate of Formula XVII is reacted with 1,1'-carbonyldiimidazole employing conditions similar to that previously described for other ring formation reactions to obtain an alkyl substituted pyrimidine-2-one intermediate of Formula XVIII.

In the next step, the intermediate of Formula XVIII is reacted with 4-methylmorpholine-4-oxide and osmium tetroxide in the manner similar to that described for the preparation of the compound of Formula XII, to obtain a 2,3-dihydroxypropyl substituted pyrimidin-2-one intermediate of Formula XIX.

In the last two steps, the 2,3-dihydroxypropyl intermediate of Formula XIX is reacted with sodium periodate in the manner similar to that previously descrbed to obtain an aldehyde compound XX in the reaction mixture which is recovered and then without purification reacted with sodium borohydride in a manner similar to that previously described, to obtain the desired compound of Formula IIC. The latter may be recovered and purified in a conventional manner.

When in the compound of Formula IIC, the alkylene chain is greater than ethylene, the compound may be prepared by a similar series of reaction except that $CH_2=CH(CH_2)_{m+1}NH_2$ where m is 1 to 4 is substituted for allylamine.

(D) When the compound of Formula II is represented by:

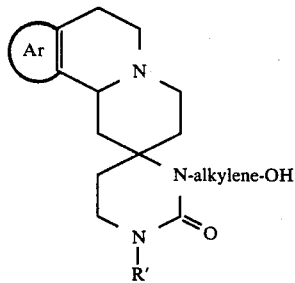

(IID)

wherein R' is lower alkyl and alkylene is ethylene, it may be prepared through the following series of reactions:

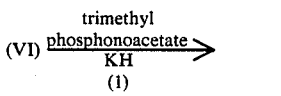

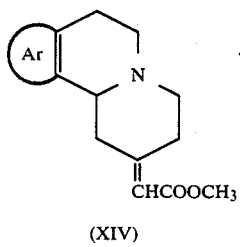

(XIV)

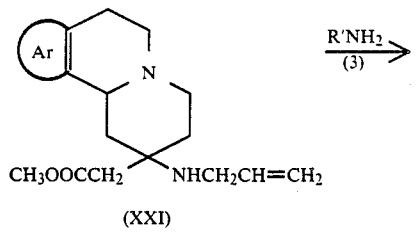

(XXI)

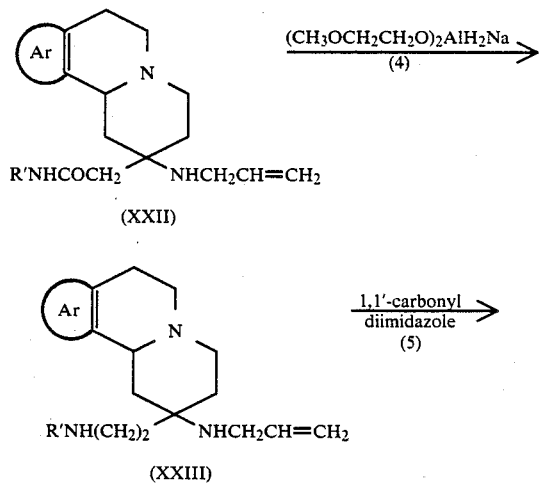

(XXII)

(XXIII)

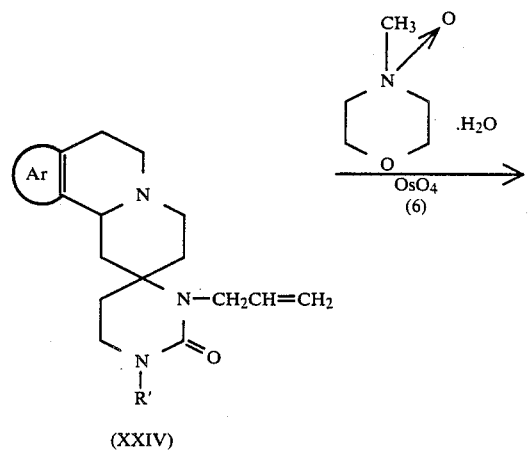

(XXIV)

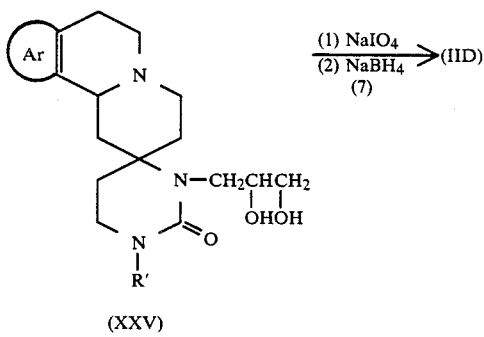

(XXV)

As the first step in carrying out the sequence of reactions for the preparation of the compounds of Formula IID, the quinolizin-2-one compound of Formula VI is reacted with trimethyl phosphonoacetate in the presence of potassium hydride in a manner of the first step in the preparation of the compound of Formula IIC to obtain the carboxymethylidene intermediate (XIV).

In the second step, the carboxymethylidene intermediate (XIV) and allylamine are reacted by refluxing an ethanol solution of the mixture under inert atmosphere for from 15 to 20 hours to obtain a 2-propenylaminoquinolizin-2-yl acetate (XXI) in the reaction mixture. The product may be recovered by vaporizing the solvent and purifying the residue by spinning disc chromatography employing 1:1 hexane/ammonia saturated chloroform as eluant.

In the third step, the 2-propenylaminoquinolizin-2-yl acetate and dry methylamine may be reacted in a pressure vessel cooled to $-78°$ C. in a manner similar to that described for Step 2 in the preparation of the compound of Formula IIC, to obtain an N-alkylacetamide compound of Formula XXII, which may then be recovered as previously described and purified by medium pressure column chromatography employing ammonia saturated chloroform as eluant.

In the fourth step, the N-alkylacetamide compound of Formula XXII is reacted with sodium bis(2-methoxyethoxy)aluminum hydride in a manner similar to that employed in Step 4 in the preparation of the compound of Formula IIC, to N-alkylacetamide group to a alkylaminoethyl group and to obtain the compound of Formula XXIII.

In the fifth step, the compound of Formula XXIII is reacted with 1,1'-carbonyldiimidfazole in the manner previously described to obtain a (2-propenyl)pyrimidin-2-one compound of Formula XXIV which may be recovered and purified by spinning disc chromatography.

In the sixth step, the (2-propenyl)pyrimidin-2-one compound of Formula XXIV and 4-methylmorpholine-4-oxide monohydrate in tetrahydrofuran are reacted with osmium tetroxide in a manner previously described to obtain a 2,3-dihydroxypropyl compound of Formula XXV which after recovery may be purified by flash column chromatography employing ammonia saturated chloroform as eluant.

In the next step, the 2,3-dihydroxypropyl compound of Formula XXV is reacted with sodium periodate in alkaline medium in the manner previously described in Step 5 in the preparation of Compound IIB, to obtain an aldehyde compound which is immediately reacted with a large excess of sodium borohydride in the manner described in Step 6 of the preparation of Compound IIB to obtain the compound of Formula IID.

Compounds of the Formula IB-2, where n=1, may be obtained more directly from quinolizin-2-one (VI) without forming the ester compound by introducing the amide group prior to cyclization with the formation of the imidazolidinone or the diazinone ring. Thus, the synthesis may be carried out through the following sequence of reactions.

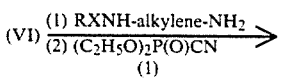

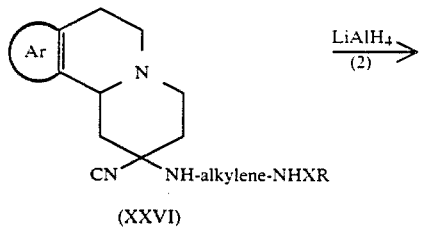

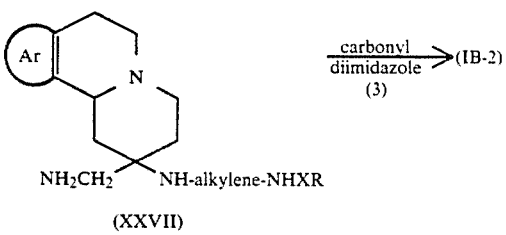

The sequence employs steps very similar to those described for the preparation of Compounds IIA–IID and the conditions are generally very similar. In this method, however, it may be necessary to first prepare various amines, RXNH-alkylene-NH$_2$, which is the source of the RXNH-alkylene- substituent in IB. This amine may be prepared by reacting RXCl with acetylated alkylenediamine in the cold in the presence of tertiary base such as triethylamine and the like to obtain a RXNH-alkylene-NHCOCH$_3$ intermediate which then may be heated with hydrochloric acid solution to obtain the RXNH-alkylene-NH$_2$ compound as the hydrochloride. The latter is converted to the free base and is then employed in the foregoing sequence of reactions.

In the first step, the amine compound is added to a solution of quinolizin-2-one (VI) in methanolic tetrahydrofuran. Then the diethyl cyanophosphonate is added and the component allowed to react by standing at room temperature for several hours to obtain the intermediate Compound XXVI. The latter may be recovered and purified employing conventional procedures.

In the second step, the intermediate Compound XXVI is subjected to a reduction step similar to that previously described in the preparation of Compound VII. In the reduction, a solution of Compound XXVI in an inert ethereal solvent may be contacted with a reducing agent such as lithium aluminum hydride at temperatures of about 0° C. and the mixture allowed to react from 1 to serveral hours to obtain intermediate Compound XXVII which then may be recovered and purified employing conventional procedures.

In the third step of cyclization, carbonyldiimidazole is added to a solution of Compound XXVII in an inert solvent such as methylene chloride and the resulting mixture allowed to react at ambient temperature or up to about 50° C. for several hours to obtain the desired product of Formula IB-2. The latter may be recovered and purified employing conventional procedures.

Compounds of formula IB-2, where n=2, may be prepared through a similar sequence of reaction but substituting diethyl cyanomethylphosphonate for the diethyl cyanophosphonate and employing similar sequence of steps.

The procedure may be modified by employing an unsubstituted alkylene diamine in the first step to obtain

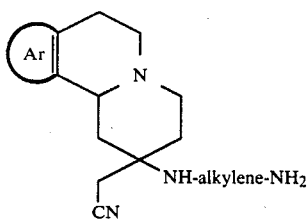

(XXVIII)

and thereafter introducing the alkylsulfonyl group to the terminal amino group.

When the compounds of Formula IB-2 to be prepared are those in which R is amino, a compound of Formula XXVIII is first prepared and then carried through the following sequence of reactions.

In the first above, a solution of tertiary butylsulfamyl chloride in methylene chloride is added under inert atmosphere to a cooled to 0° C. solution of the appropriate quinolizine compound (XXVIII) in methylene chloride and diisopropylethylamine and the mixture stirred at ambient temperature overnight to obtain Compound XXIX. The latter is then recovered using conventional procedures and is preferably purified by chromatographing over silica gel.

In the second step, the intermediate Compound XXIX is subjected to a reduction, preferably employing lithium aluminum hydride in ethereal solution at about 0° C. as above described to obtain Compound XXX which is then recovered in a conventional manner.

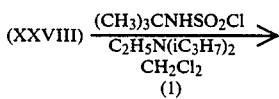

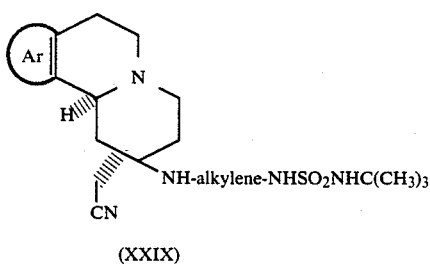

(XXIX)

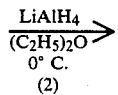

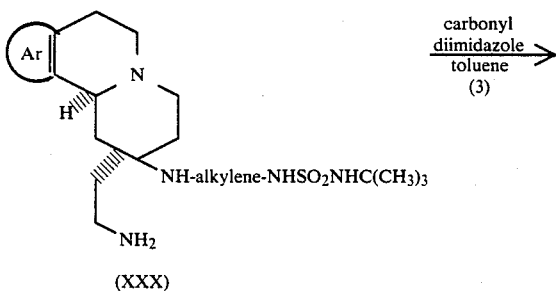

(XXX)

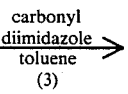

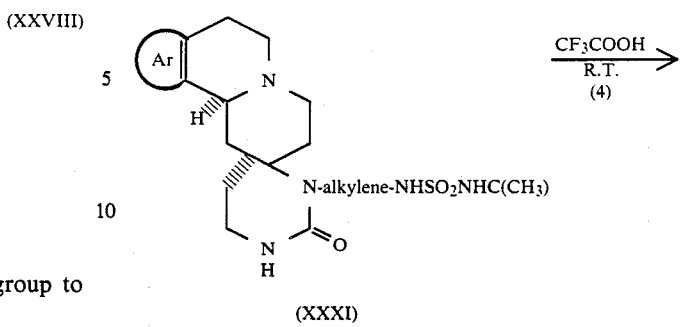

(XXXI)

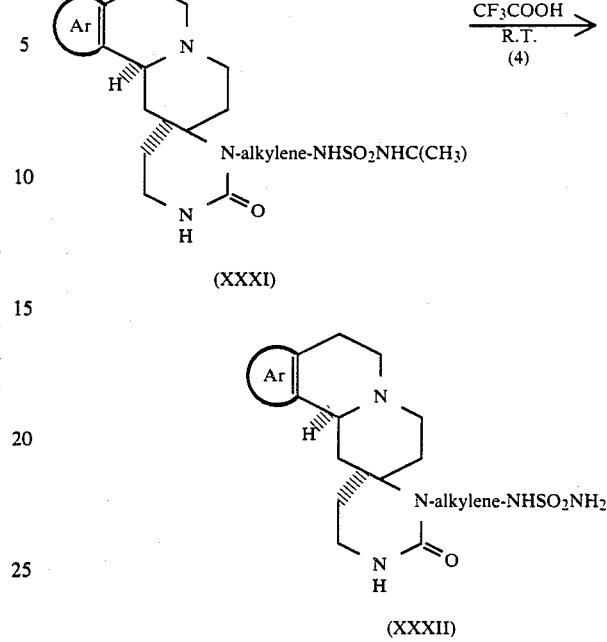

(XXXII)

The third cyclization step is carried out in a manner similar to that above described with Compound XXVII to obtain Compound XXXI.

The tertiary-butyl group may be removed according to step (4) by intimately mixing Compound XXXI and trifluoroacetic acid at room temperature for several hours to obtain Compound XXXII in the reaction mixture. The latter may be recovered first by diluting the reaction mixture with an inert solvent such as chloroform, making the mixture basic then isolating using conventional procedures.

All of the foregoing methods for the preparation of the desired hexahydroquinolizine may be carried out on a resolved enantiomer as well as on a racemic mixture. When a specific enantiomer desired, it is preferably to resolve the starting quinolizin-2-one (VI) rather than the product or intermediate. Preferred resolving agents are acylated L-tartaric acid such as di-para-toluoyl-L-tartaric acid, di-para-toluoyl-D-tartaric acid.

The ultimate starting material in the preparation of the compounds of the present invention is an appropriate aromatic ethylamine $ArCH_2CH_2NH_2$. Thus, when the Ar is a benzofuro group, the starting material would be 3-(2-aminomethyl)benzofuran. The sequence of reactions is as follows:

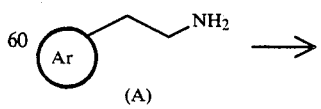

(A)

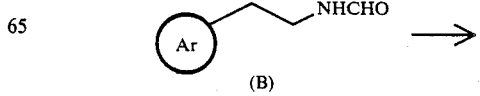

(B)

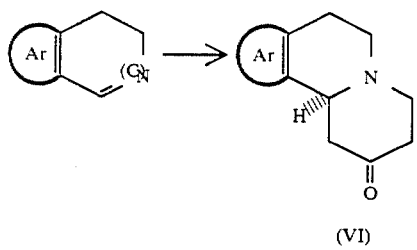

(VI)

In carrying out the foregoing process, the aminomethyl compound (A) is heated with ethyl formate at about 60° C. for several hours, the reaction mixture then poured into dilute hydrochloric acid, the resulting mixture extracted with methylene chloride, the extract purified, dried, and the solvent evaporated to obtain the formamido compound (B). The latter is added to strong acid or dehydrating agent such as polyphosphoric acid, phosphorus pentoxide, or methane sulfonic acid at 100° C. and the mixture heated for 1-2 hours to obtain an Ar-condensed dihydropyridine compound (C) which may be recovered by conventional procedures. Compound C may than be converted to the quinolizin-2-one (VI) by adding 2-trimethylsilyloxy-1,3-butadiene, then zinc chloride, heating the mixture at 60° C. 1-2 hours and thereafter recovering by conventional procedures.

The selective $\alpha_2$-adrenoceptor blocking property was discovered by and may be demonstrated by an in vitro rat vas deferens test and an in vivo test measuring antagonism of clonidine induced mydriasis.

In Vitro Rat Vas Deferens Study

The in vitro rat vas deferens test is a measure of affinity for peripheral $\alpha_2$-adrenoccceptors and is adapted from experimental results reported by Drew, Eur. J. Pharmacol. 42, 123 (1977); Doxy et al., Brit. J. Pharmacol. 60, 91 (1977); and Lotti et al., Life Sci. 29, 633 (1981). In the test, isolated, field-stimulated rat vas deferens is utilized as an in vitro model to determine the potency and selectivity of compounds toward the various $\alpha$-adrenoceptor subtypes. Selective $\alpha_2$-adrenoceptor agonists such as clonidine reduce the magnitude of neurogenic contractions in the peripheral smooth muscle by reducing the stimulated release of norepinephine through the activation of presynaptic $\alpha_2$-adrenoceptors on the noradrenergic nerve terminals. The effect of clonidine is blocked by selective antagonist of $\alpha_2$-adrenoceptor such as yohimbine. The antagonist activity of the compounds of the present invention is compared against the activity exhibited by yohimbine employing (2R,12bS)-3'-(2-methanesulfonamidoethyl)-spiro-[1,3,4,6,7,12b-hexahydrobenzo[b]furo[2,3-a]quinolizin]-2,4'-imidazolidin-2'-one (arylquinolizine Compound A) as a representative compound and using the following procedure:

The vas deferens from rats weighing 250-350 grams were freed of connective and fatty tissue and suspended between two platinum electrodes in an organ bath under 0.5 gram tension. The organ bath contained Tyrode's solution which was bubbled with 5% $CO_2$ and 95% $O_2$ and stimulated with square wave pulses at 0.1 Hz, 0.3 msec in duration and supramaximal voltage (30-50 V). Contractile responses were recorded. $\alpha_2$-Agonist drug (clonidine) was added cumulatively to the bath and $EC_{50}$ values determined by regression analysis. After washout, antagonist was allowed at least 20 minutes contact with the tissues and the $EC_{50}$ of agonist in the presence of antagonist was similarly determined. The concentration of the subject compound necessary to double the $EC_{50}$ of the agonist ($pA_2$) was estimated from regression analysis of Schild plots [Arunlakshana and Schild, 1959] using at least three concentrations of the antagonists and at least four tissues at each concentration. Computation of the $pA_2$ value was performed using the formula: $pA_2 = pA_x + \log(x-1)$, where $pA_x$ is the negative logarithm of the molar concentration of antagonist and x is the dose ratio of $EC_{50}$ values for the agonist before and after addition of the antagonist. The results are seen in Table A.

Antagonism of Chlonidine-Induced Mydriasis

Administration of clonidine to rat produces mydriasis by an $\alpha_2$-adrenergic mechanism in the central nervous system as reported by Koss et al., Naunyl-Schmiedeberg's Arch. Pharmacol. 307, 45 (1979); Koss et al., Invest. Ophthal. 15, 566 (1976); and Berridge et al., Brit. J. Pharmacol. 78, 507 (1983). Antagonism of the mydriatic action of clonidine was used as an in vivo test to examine the ability of the compounds to penetrate the central nervous system and antagonize $\alpha_2$-adrenoceptors in the rat. The antagonistic acitivity of the compounds of the present invention as represented by (2R,12bS)-3'-(2-methanesulfonamidoethyl)spiro-[1,3,4,6,7,12b-hexahydrobenzo[b]-furo[2,3-a]quinolizin]-2,4'-imidazolidin-2'-one was compared with yohimbine using the following procedure:

Adult male Sprague-Dawley rats (250-450 g) were anesthetized with chloral hydrate (120-160 mg/kg i.p.), and a femoral vein was cannulated for drug administration. Body temperature was maintained at 37° C.±0.5. The eye was illuminated using a light with green filters to provide added contrast to aid in visualization of the iris. Pupil diameter was measured using a dissecting microscope containing an ocular micrometer with a resolution of 0.1 mm.

Rats were pretreated with the imidazolidin-2-one compound or with yohimbine at 5 minutes prior to administering increasing doses of clonidine intravenously. Five minutes was allowed to elapse between successive doses of clonidine, and pupil diameter was determined immediately prior to the injection of the next dose of clonidine. The dose of clonidine required to cause 50% of the maximum increase in diameter of the pupil was determined for each rat, using logarithmic linear regression analysis. Geometric mean $ED_{50}$ values (Fleming et al., 1972) were calculated for each treatment group (N=4/group). The potency of antagonists was expressed as $ED_{2x}$ values, i.e. the calculated dose of antagonist required to cause a doubling in the $ED_{50}$ value for clonidine. These results are also seen in Table A.

TABLE A

| Compound | Vas Deferens ($pA_2$) vs Clonidine | Antagonism of Clonidine Induced Mydriasis ($ED_{2x}$ mg/kg i.v.) |
|---|---|---|
| Arylquinolizine Compound A* | 8.52 | 18.0 |
| Yohimbine | 7.65 | 0.136 |

*(2R,12bS)-3'-(2-methanesulfonamidoethyl)spiro-[1,3,4,6,7,12b-hexahydro[b-]furo[2,3-a]quinolizin]-2,4'-imidazolidin-2'-one Arylquinolizine compound A has seven-fold higher affinity for $\alpha_2$-adrenoceptors than yohimbine as seen by the vas deferens data but it is 132 fold less potent in eliciting a response mediated by central α₂-adrenoceptors (mydriasis data). Thus, the compounds of the present invention are highly selective peripheral antagonists and the present active compound (2R,12bS)-3'-(2-methanesulfonamidoethyl)spiro[1,3,4,6,7,12b-hexahydro[b]furo[2,3-a]quinolizin]-2,4'-imidazolidin-2'-one is about 900 times more selective for the periphery than yohimbine, a classical α₂-adrenoceptor antagonist.

The process of the present invention comprises administering to subjects with a pathological condition attributable to undesirable α-adrenoceptor acitivity, a therapeutically effective amount of a composition comprising an arylquinolizine compound or a pharmaceutically acceptable acid addition salt thereof. In general, the daily dose may be that amount to provide between about 0.01 and 20 mg/kg/day, preferably in the range 0.1 and 10 mg/kg/day while considering patients' health, weight, age and other factors which influence response to a drug as well as the particular drug to be employed. Further, since the drug is useful in several pathological conditions, the dose is also dependent on the particular disease to be alleviated. The drug may be administered orally or parenterally or by any other means, and in a single unit or in a number of smaller units given during the period of a day in compositions hereinafter detailed.

The pharmaceutical compositions of the present invention comprises a hexahydroaryliquinolizine compound of Formula I or a pharmaceutically acceptable acid addition salt thereof in intimate admixture with a pharmaceutically acceptable carrier. The optically active products as well as racemic or other mixture may be prepared in a manner suitable for either oral or parenteral administration.

The carrier may take a wide variety of forms depending on the form of preparation desired for administration, e.g., oral or parenteral. In compositions for oral administration, any of the usual pharmaceutical media may be employed. Thus, for liquid oral preparations, such as, for example, suspensions, elixirs and solutions, suitable carriers and additives include water, glycols, oils, alccohols, flavoring agents, preservatives, coloring agents and the like; for solid oral preparation such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed.

It is especially advantageous to formulate the pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit form are tablets, capsules, pills, powder packets, wafers, teaspoonfuls, tablespoonfuls and the like, and segregated multiples thereof. The amount of active ingredient per dosage unit will be from about 1 mg. to about 500 mg. Preferably, the amount of active ingredient would be from about 5 to about 100 mg.

The following examples illustrate the invention but are not to be construed as limiting.

EXAMPLE I (2RS,12bSR)-1'-(2-Methanesulfonyloxyethyl)-3'-methyl-spiro[1,3,4,6,7,12b-hexahydrobenzo[b]furo[2,3-a]-quinolizin]-2,4'-imidazolidin-2'-one

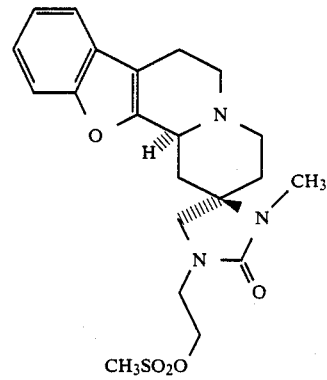

Step A: Preparation of (2RS,12bSR)-2-aminomethyl-2-methylamino-1,3,4,6,7,12b-hexahydrobenzo[b]furo[2,3-a]quinolizine Into a 1000 milliliter flask was placed 7 grams (29 mmol) of 1,3,4,6,7,12b-hexahydrobenzo-[b]furo[2,3-a]quinolizin-2-one in 500 milliliters of dry tetrahydrofuran which had previously been saturated with dry methylamine at 0° C. To this mixture was added 10.44 grams (64 mmol) of diethyl cyanophosphonate. After stirring for 18 hours, the solvent was removed and the resultant crude aminonitrile was dissolved in 300 ml dry tetrahydrofuran and treated with 145 ml 1M borane in THF. This mixture was refluxed for 18 hours, cooled and quenched by the slow addition of methanol until ebullition ceased, after which 400 ml 6N HCl was added and the reaction mixture was refluxed for an additional 2 hours. After cooling, the solvent was removed and the residue was basified by the addition of 400 ml saturated Na₂CO₃ solution. This was extracted with 5×100 ml CHCl₃. The combined organic extracts were dried (Na₂SO₄) and the solvent was evaporated. Medium pressure column chromatography on silica gel (chloroform saturated with ammonia) yielded 0.552 g. (7%) (2SR,12bSR)-2-aminomethyl-2-methylamino-1,3,4,6,7,12b-hexahydrobenzo[b]furo[2,3-a]quinolizine as a yellow oil, followed by 4.9 g of the desired product (62%) (2RS,12bSR)-2-aminomethyl-2-methylamino-1,3,4,6,7,12b-hexahydrobenzo[b]furo[2,3-a]quinolizine, also as a yellow oil.

Similarly prepared are the (2R,12bS)- and (2S,12bR) enantiomers by starting with the enantiomeric quinolizin-2-ones.

Step B: Preparation of (2RS,12bSR)-3'-methyl-spiro(1,3,4,6,7,12b-hexahydrobenzo[b]furo-[2,3-a]quinolizin)-2,4'-imidazolidin-2'-one Into a 400 ml flask was placed 4.4 g (15.8 mmol) of (2RS,12bSR)-2-aminomethyl-2-methylamino-1,3,4,6,7,12b-hexahydrobenzo[b]furo[2,3-a]-quinolizine from Step A in 200 ml toluene. To this was added 5 g (32 mmol) of 1,1'-carbonyldiimidazole and the reaction was stirred for 5 hours, after which the toluene was washed with 3×50 ml H$_2$O, 50 ml brine, dried (Na$_2$SO$_4$) and the solvent evaporated to obtain a yellow solid. This material was dissolved in hot ethyl acetate, decolorized, filtered and treated with ethanolic HCl to give 3.53 g (72%) of (2RS,12bSR)-3'-methyl-spiro(1,3,4,6,7,12b-hexahydrobenzo[b]furo[2,3-a]quinolizin)-2,4'-imidazolidin-2'-one as a white crystalline hydrochloride salt which was recrystallized from methanol/ethyl acetate: m.p. 220° C. (dec).

Similarly prepared are the (2RS,12bs)- and (2S,12bR)-enantiomers of the 3'-methylimidazolidin-2'-one by starting with the enantiomeric diamines described in Step A hereof.

Step C: Preparation of 2-methoxy-2-(2-iodoethoxy)propane

To 6 mls of cold (0° C.) methoxypropene was added 3 mls of 2-iodoethanol and 1 drop of phosphorous oxychloride (POCl$_3$). The reaction was stirred for 1 hour and then solid potassium carbonate was added. After 10 minutes the liquid was decanted and was concentrated to obtain the product as an oil.

Step D: Preparation of (2RS,12bSR)-1'-(2-hydroxyethyl-3'-methyl-spiro[1,3,4,6,7,12b-hexahydrobenzo[b]furo[2,3-a]quinolizin]-2,4'-imidazolidin-2'-one HCl, 0.25 H$_2$O To a solution of the 3'-methylimidazolidin-2'-one (0.04 g, 0.16 mmol) from Step B of Example I in 20 ml of toluene was added tetrabutylammonium hydrogen sulfate (0.082 g, 0.24 mmol), 20 mls of 40% sodium hydroxide solution, and, with vigorous stirring, 2-methoxy-2-(2-iodoethoxy)propane (0.053 g, 0.209 mmol). This was stirred for 45 hours and then the toluene layer was poured into 20 mls of 5% HCl solution, stirred for 15 minutes and then made basic. The toluene layer was separated and washed with 3×30 ml of water, 30 ml of brine, dried (Na$_2$SO$_4$) filtered and concentrated to obtain an oil which was chromatographed (silica, NH$_3$/saturated CHCl$_3$) to recover the product as the HCl, (0.25 H$_2$O; m.p. 172-176° C.).

Step E: Preparation of (2RS,12bSR)-1'-(2-methanesulfonyloxyethyl)-3'-methyl-spiro[1,3,4,6,7,12b-hexahydrobenzo[b]furo[2,3-a]quinolizin]-2,4'-imidazolidin-2'-one A mixture of 0.073 gram (0.21 mmol) of (2RS,12bSR)-1'-(2-hydroxyethyl)-3'-methyl-spiro[1,3,4,6,7,12b-hexahydro-benzo[b]furo[2,3-a]quinolizin]-2,4'-imidazolidin-2'-one and 0.08 gram (0.108 ml, 0.63 mmol) of diisopropylethylamine in 20 milliliters of methylene chloride was cooled to 0° C. To this solution was added dropwise 0.07 gram (0.048 ml, 0.63 mmol) of methanesulfonyl chloride in 5 milliliters of methylene chloride. A thin layer chromatographic (TLC) analysis (ammonia saturated chloroform as eluant) after completion of the addition showed that the reaction was incomplete. Another 3 equivalents of diisopropylethylamine and methanesulfonyl chloride were added in the same manner to complete the formation of the ester compound. The reaction mixture was then poured into 50 milliliters of water and the organic portion was separated from the aqueous portion and washed with three 50 milliliter portions of water, two 50 milliliter portions of saturated sodium carbonate solution, and then dried over sodium sulfate. The solvent was then removed from the dried solution to obtain (2RS,12bSR)-1'-(2-methanesulfonyloxyethyl)-3'-methyl-spiro[1,3,4,6,7,12b-hexahydrobenzo[b]furo[2,3-a]quinolizin]-2,4'-imidazolidin-2'-one as a yellow oil in a substantially quantitative yield.

EXAMPLE IA

Employing the procedure substantially as described in Steps A and B of Example I but substituting for 1,3,4,6,7,12b-hexahydrobenzo[b]furo[2,3-a]quinolizin-2-one, a quinolizin-2-one of Formula VI with various Ar substituents, and for the methylamine, an amine of the formula, R$^3$NH$_2$ there are prepared the spiro-imidazolidin-2-ones of Formula VIII wherein the Ar is as designated in Table I.

Then employing substantially the same procedure as described in Step C of Example I but substituting other ω-iodo alkanols for 2-iodoethanol there are prepared the following 2-methoxy-2-(ω-iodoalkoxy) propanes: 2-methoxy-2-(3-iodopropoxy)propane, 2-methoxy-2-(1-iodo-2-propoxy)propane, 2-methoxy-2-(5-iodopentyloxy)propane, and 2-methoxy-2-(2-iodocyclopentyloxy)propane.

Thereafter, in separate operations, 2-methoxy-2-(ω-iodoalkoxy)propane is reacted with a spiro-imidazolidin-2-one as described in Step D of Example I to obtain 2-hydroxyethyl-imidazolin-2-ones of Formula IIA which then is reacted with RXCl instead of methanesulfonyl chloride as described in Step E of Example I to obtain the compounds of Formula IA-1, listed on Table I.

TABLE I

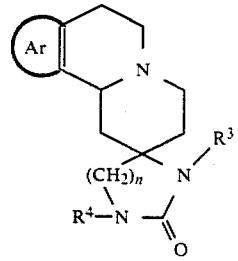

| Ar | R$^3$ | R$^4$ (RXOalkylene) | n |
|---|---|---|---|
| 10-chlorobenzo-[b]furo- | CH$_3$— | CH$_3$COOCH$_2$CH$_2$— | 1 |
| thieno | H— | C$_2$H$_5$SO$_2$OCH$_2$CH$_2$— | " |
| furo | C$_2$H$_5$— | (n-C$_3$H$_7$O)$_2$P(O)OCH$_2$CH$_2$— | " |
| 11-hydroxy-benzo[b]furo | C$_3$H$_7$— | (C$_6$H$_5$O)$_2$P(O)OCH$_2$CH$_2$— | " |
| 10,11-dimethyl-benzo[b]furo- | CH$_3$— | C$_6$H$_5$CH$_2$NHCOOCH$_2$CH$_2$— | " |
| pyridino- | CH$_3$— | CF$_3$COOCH$_2$CH$_2$— | " |
| imidazo | CH$_3$— | H$_2$NSO$_2$OCH$_2$CH$_2$— | " |
| benzo | CH$_3$— | (CH$_3$)$_2$NCOOCH$_2$CH$_2$— | " |
| benzo[b]thieno- | CH$_3$— | CH$_3$COOCH$_2$CH$_2$— | 1 |
| 10-methylbenzo-[b]thieno- | CH$_3$— | n-C$_3$H$_7$SO$_2$OCH$_2$CH$_2$— | " |
| 9-methoxybenzo-[b]thieno | H— | (C$_2$H$_5$O)$_2$P(O)OCH$_2$CH$_2$— | " |

TABLE I-continued

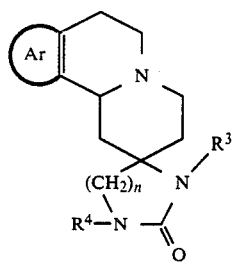

| Ar | R³ | R⁴ (RXOalkylene) | n |
|---|---|---|---|
| 11-fluorobenzo-[b]furo- | H— | C₆H₅CH₂NHCOOCH₂CH₂— | " |
| 9-bromobenzo-[b]furo- | PhCH₂— | CF₃COOCH₂CH₂— | " |
| 11-methoxybenzo-[b]furo | H— | H₂NSO₂OCH₂CH₂— | " |
| thiazolo- | CH₃— | C₂H₅COOCH₂CH₂— | " |
| pyrazolo- | CH₃— | C₂H₅SO₂OCH₂CH₂— | " |
| benzo[b]furo- | H— | CH₃SO₂OCH₂CH₂CH₂— | " |
| 9-methoxybenzo-benzo[b]furo | H— | H₂NSO₂OCH(CH₃)CH₂— | " |
| | CH₃— | CH₃SO₂O(CH₂)₅— | " |
| benzothieno | CH₃— |  CH₃SO₂O—⟨pentyl⟩ | " |
| 9-methoxybenzo | H— | 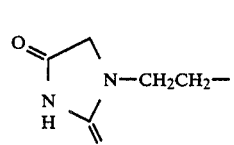 (imidazolidinone-N-CH₂CH₂—) | " |

EXAMPLE II (2RS,12bSR)-1'-(2-Methanesulfonamidoethyl)-3'-methyl-spiro[1,3,4,6,7,12b-hexahydrobenzo[b]furo[2,3-a]quinolizin]-2,4'-imidazolidin-2'-one

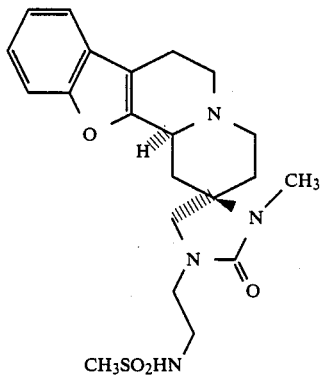

Step A: Preparation of (2RS,12bSR)-1'-(2-azidoethyl)-3'-methyl-spiro[1,3,4,6,7,12b-hexahydrobenzo[b]furo[2,3-a]quinolizin]-2,4'-imidazolidin-2'-one To a solution of 0.432 gram (1.0 mmol) of (2RS,12bSR)-1'-(2-methanesulfonyloxyethyl)-3'-methyl-spiro[1,3,4,6,7,12b-hexahydrobenzo[b]furo[2,3-a]quinolizin]-2,4'-imidazolidin-2'-one, prepared as described in Example I, in 50 milliliters of N,N-dimethylformamide is added 0.2 gram of sodium azide and the mixture is heated at 90°-100° C. for 4 hours. The mixture is cooled to ambient temperature, then added to ice-water and extracted with methylene chloride. The organic layers are then combined, washed with saturated NaCl and dried (Na₂SO₄). The drying agent is filtered and the solvent evaporated to obtain (2RS,12bSR)-1'-(2-azidoethyl-3'-methyl-spiro[1,3,4,6,7,12b-hexahydrobenzo[b]furo[2,3-a]quinolizin]-2,4'-imidazolidin-2'-one.

Step B: Preparation of (2RS,12bSR)-1'-(2-aminoethyl)-3'-methyl-spiro[1,3,4,6,7,12b-hexahydrobenzo[b]furo[2,3-a]quinolizin]-2,4'-imidazolidin-2'-one A solution of 0.38 gram (1 millimole) of (2RS,12bSR)-1'-(2-azidoethyl)-3'-methyl-spiro[1,3,4,6,7,12b-hexahydrobenzo[b]furo[2,3-a]quinolizin]-2,4'-imidazolidin-2'-one in 100 milliliters of ethanol is hydrogenated in a Parr apparatus in the presence of 10 mol% of 5% Pd on carbon for 4 hours. The catalyst is then filtered off and the solvent evaporated off to obtain (2RS,12bSR)-1'-(2-aminoethyl)-3'-methyl-spiro-[1,3,4,6,7,12b-hexahydrobenzo[b]furo[2,3-a]quinolizin]-2,4'-imidazolidin-2'-one.

Step C: Preparation of (2RS,12bSR)-1'-(2-methanesulfonamidoethyl)-3'-methyl-spiro[1,3,4,6,7,12b-hexahydrobenzo[b]furo[2,3-a]quinolizin]-2,4'-imidazolidin-2'-one A mixture of 0.354 grams (1 mmol) (2RS,12bSR)-1'-(2-aminoethyl)-3'-methyl-spiro[1,3,4,6,7,12b-hexahydrobenzo[b]furo[2,3-a]quinolizin]-2,4'-imidazolidin-2'-one and 1.5 mmols triethylamine in methylene chloride is treated with 0.17 gram (1.5 mmols) methanesulfonyl chloride at 0° C. and left to warm to ambient temperature over 2 hours. The mixture is partitioned between water and methylene chloride, the organic layer separated, washed with brine, and dried (Na₂SO₄). The drying agent is filtered and the solvent evaporated from the filtrate to obtain (2RS,12bSR)-1'-(2-methanesulfonamidoethyl)-3'-methyl-spiro[1,3,4,6,7,12b-hexahydrobenzo[b]furo-[2,3-a]quinolizin]-2,4'-imiadazolidin-2'-one.

Employing the procedure substantially as described in Example II, Step C, but substituting for the racemic amine from Step B equal amounts of the substantially enantiomerically pure amines there are produced the (2R,12bS)-1'-(2-methanesulfonamidoethyl)-3'-methyl-spiro[1,3,4,6,7,12b-hexahydrobenzo[b]furo[2,3-a]quinolizin]-2,4'-imidazolidin-2'-one and the (2S,12bR)-1'-(2-methanesulfonamidoethyl)---methyl-spiro[1,3,4,6,7,12b-hexahydrobenzo[b]furo[2,3-a]-quinolizin]-2,4'-imidazolidin-2'-one and the (2S,12bR)-1'-(2-methanesulfonamidoethyl)-3'-methyl-spiro[1,3,4,6,7,12b-hexahydrobenzo[b]furo[2,3-a]quinolizin]-2,4'-imidazolidin-2'-one.

EXAMPLE IIA (2RS,12bSR)-1'-(2-Methanesulfonamidoethyl)-3'-methyl-spiro[1,3,4,6,7,12b-hexahydrobenzo[b]furo[2,3-a]-quinolizin]-2,4'-imidazolidin-2'-one The title compound, identical to that of Example II, also may be prepared by the following method:

Potassium hydride (0.077 gram of a 25 percent dispersion in oil, 0.048 mmol) was washed twice with hexane and then slurried in 20 milliliters of 1:1 tetrahydrofuran/dimethylsulfoxide. To the resulting slurry was added with stirring 0.068 gram (0.72 mmol) of methanesulfonamide and the stirring continued for 30 minutes. At this time, 0.01 gram of 18-Crown-6 (1,4,7,10,13,16-hexaoxacyclooctadecane) was added to the mixture followed by 0.090 gram (0.24 mmol) of (2RS, 12bSR)-1'-(2-methanesulfonyloxyethyl)-3'-methyl-spiro[1,3,4,6,7,12b-hexahydrobenzo[b]furo[2,3-a]quinolizin]-2,4'-imidazolidin-2'-one prepared as described in Example I, and the resulting mixture heated to and maintained at 80° C. for 5 hours to obtain the desired sulfonamide product in the reaction mixture. The mixture is cooled, diluted with water, and then extracted with ethyl acetate and the extract purified by spinning disc chromatography employing ammonia saturated chloroform as eluant to obtain 0.028 gram (27 percent yield) of the desired (2RS,12bSR)-1'-(2-methanesulfonamidoethyl)-3'-methyl-spiro[1,3,4,6,7,12b-hexahydrobenzo[b]furo[2,3-a]quinolizin-2,4'-imidazolidin-2'-one] product. The product was reacted with HCl to obtain the hydrochloride monohydrate salt, m.p. 176°–178° C.

EXAMPLE IIB

Employing the procedure substantially as described in Example II, but substituting RXCl for the methanesulfonyl chloride and the appropriate compound of Formula IA-1 where n=1, there may be produced the imidazolidin-2-ones of Formula IB-1 and described in Table II.

Alternatively, employing the procedure substantially as described in Example IIA, but substituting RXNH$_2$ for the methanesulfonamide and the appropriate compound of formula IA-1 where n=1, there may be produced the imidazolidin-2-ones of Formula IB-1 described in Table II.

TABLE II

| Ar | R$^3$ | R$^4$ (RXNHalkylene) | n |
|---|---|---|---|
| 10-chlorobenzo[b]furo- | CH$_3$— | CH$_3$SO$_2$NHCH$_2$CH$_2$— | 1 |
| thieno | H— | CH$_3$CONHCH$_2$CH$_2$— | " |
| furo | C$_2$H$_5$— | C$_2$H$_5$NHCONHCH$_2$CH$_2$— | " |
| 11-hydroxybenzo[b]furo | n-C$_3$H$_7$— | NH$_2$CONHCH$_2$CH$_2$— | " |
| 10,11-dimethylbenzo[b]furo | CH$_3$— | N(CH$_3$)$_2$CSNHCH$_2$CH$_2$— | " |
| pyridino | H— | NH$_2$SO$_2$NHCH$_2$CH$_2$— | " |
| imidazo | C$_2$H$_5$— | CH$_3$OCONHCH$_2$CH$_2$— | " |
| benzo | i-C$_3$H$_7$— | CF$_3$SO$_2$NHCH$_2$CH$_2$— | " |
| benzo[b]thieno | CH$_3$— | CF$_3$CONHCH$_2$CH$_2$— | " |
| 9-methoxybenzo[b]thieno | H— | (CH$_3$O)$_2$P(O)NHCH$_2$CH$_2$— | " |
| 9-bromobenzo[b]furo | C$_2$H$_5$— | (NH$_2$)$_2$P(O)NHCH$_2$CH$_2$— | " |
| thiazolo | n-C$_3$H$_7$— | C$_6$H$_5$CH$_2$CONHCH$_2$CH$_2$— | " |
| pyrazolo | CH$_3$— | C$_6$H$_5$CONHCH$_2$CH$_2$— | " |
| benzo[b]furo | H— | CH$_3$SO$_2$NHCH$_2$CH$_2$CH$_2$— | " |
| 9-methoxybenzo | H— | H$_2$NSO$_2$NHCH(CH$_3$)CH$_2$— | " |
| benzo[b]furo | CH$_3$— | CH$_3$SO$_2$NH(CH$_2$)$_5$— | " |
| benzo[b]thieno | CH$_3$— | 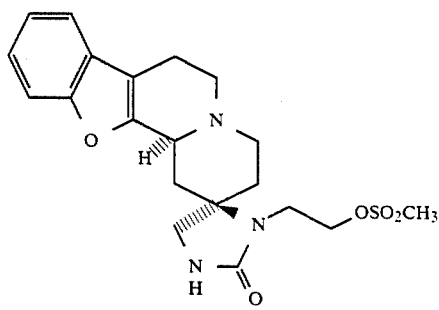 | " |

EXAMPLE III (2RS,12bSR)-3'-(2-Methanesulfonyloxyethyl)-spiro[1,3,4,6,7,12b-hexahydrobenzo[b]furo[2,3-a]quinolizin]-2,4'-imidazolidin-2'-one Step A: Preparation of (2RS,12bSR)-2-cyano-2-(2-propenylamino)-1,3,4,6,7,12b-hexahydro-2H-benzofuro[2,3-a]quinolizine To a solution of 350 milligrams (1.45 millimoles) of (12bSR)-1,3,4,6,7,12b-hexahydro-2H-benzo[b]furo[2,3-a]quinolizin-2-one in 50 milliliters of tetrahydrofuran is added (3.02 mmol) of allylamine followed by 370 milligrams (2.28 mmol) of diethyl cyanophosphonate. After 3 hours at room temperature, the reaction mixture is concentrated and the residue is chromatographed to obtain (2RS,12bSR)-2-cyano-2-(2-propenylamino)-1,3,4,6,7-12b-hexahydro-2H-benzofuro[2,3-a]quinolizine-2,4'-imidazolidin-2'-one.

Step B: Preparation of (2RS,12bSR)-2-aminomethyl-2-(2-propenylamino)-1,3,4,6,7,12b-hexahydro-2H-benzofuro[2,3-a]quinolizine A solution of 0.325 grams (1.11 mmol) of (2RS,12bSR)-2-cyano-2-(2-propenylamino)-1,3,4,6,7,12b-hexahydro-2H-benzofuro[ 2,3-a]quinolizine in 7 milliliters of tetrahydrofuran is added to a solution of 0.084 gram (2.22 mmol) of lithium aluminium hydride in 60 milliliters of ether which has been cooled to 0° C. The reaction mixture is stirred for 1.5 hours and then quenched with water. The resulting mixture is filtered through a pad of celite and the pad then washed with methanol and methylene chloride. The filtrate is dried over sodium sulfate, then filtered and concentrated to obtain (2RS,12bSR)-2-aminomethyl-2-(2-propenylamino)-1,3,4,6,7,12b-hexohydro-2H-benzofuro[2,3-a]quinolizine.

Step C: Preparation of (2RS,12bSR)-3'-(2-propenyl)-spiro(1,3,4,6,7,12b-hexahydro-2H-benzofuro(2,3-a)quinolizine-2,4'-imidazolidin-2'-one To a solution of 0.231 gram (0.778 mmol) of (2RS,12bSR)-2-aminomethyl-2-(2-propenylamino)-1,3,4,6,7,12b-hexahydro-2H-benzofuro(2,3-a)quinolizine in methylene chloride is added 0.13 gram (0.80 mmol) of carbonyldiimidazole. The mixture is allowed to stand 5 hours at room temperature, then washed with water, the organic layer recovered and dried, filtered and concentrated to obtain (2RS,12bSR)-3'-(2-propenyl)-spiro(1,3,4,6,7,12b-hexahydro-2H-benzofuro(2,3-a)quinolizine)-2,4'-imidazolidin-2'-one.

Step D: Preparation of (2RS,12bSR)-3'-(2,3-dihydroxypropyl)-spiro(1,3,4,6,7,12b-hexahydro-2H-benzofuro(2,3-a)quinolizine)-2,4'-imidazolidin-2'-one A mixture of 0.226 gram (0.7 mmol) of (2RS,12bSR)-3'-(2-propenyl)-spiro(1,3,4,6,7,12b-hexahydro-2H-benzofuro(2,3-a)quinolizine)-2,4'-imidazolidin-2'-one and 0.143 gram (1.4 mmol) of 4-methylmorpholine-4-oxide monohydrate is dissolved in 125 milliliters of tetrahydrofuran and to the resulting solution is added 6 drops of a 0.4M solution of osmium tetroxide in tetrahydrofuran. The reaction is stirred 18 hours after which time it is poured into water and extracted into chloroform. The organic layer is dried, filtered and concentrated to obtain (2RS,12bSR)-3'-(2,3-dihydroxypropyl)-spiro-(1,3,4,6,7,12b-hexahydro-2H-benzofuro(2,3-a)quinolizine)-2,4'-imidazolidin-2'-one.

Step E: Preparation of (2RS,12bSR)-3'-(2-hydroxyethyl)-spiro(1,3,4,6,7,12b-hexohydro-2H-benzofuro(2,3-a)quinolizine)-2,4'-imidazolidin-2'-one A mixture of 44 milligrams (0.12 mmol) of (2RS,12bSR)-3'-(2,3-dihydroxypropyl)-spiro-(1,3,4,6,7,12b-hexahydro-2H-benzofuro(2,3-a)quinolizine)-2,4'-imidazolidin-2'-one, and 0.05 ml of 20% NaOH is dissolved in 5 milliliters of 95% ethanol and cooled to 0° C. To this solution is added dropwise, 77 milligrams (0.36 mmol) of sodium periodate in 1.5 milliliters of water. The reaction is stirred for 2 hours at 0° C., then the solvent is removed and the residue is partitioned between water/chloroform. The layers are separated, the organic solutions combined and dried ($Na_2SO_4$) and the solvent removed to obtain the crude aldehyde which is immediately dissolved in 5 milliliters of absolute ethanol and to the resulting solution is added a large excess (0.075 g) of sodium borohydride. The reaction mixture is stirred for 18 hours, the solvent is removed and the residue worked up to obtain (2RS,12bSR)-3'-(2hydroxyethyl)-spiro(1,3,4,6,7,12b-hexahydro-2H-benzofuro(2,3-a) quinolizine)-2,4'-imidazolidin-2'-one.

Step F: Preparation of (2RS,12bSR)-3'-(2-methanesulfonyloxyethyl)-spiro[1,3,4,6,7,12b-hexahydrobenzo[b]furo[2,3-a]quinolizin]-2,4'-imidazolidin-2'-one In a process carried out in the manner described in Example I, Step E, 0.34 gram (1 mmol) of (2RS,12bSR)-3'-(2-hydroxyethyl)-3'-methyl-spiro[1,3,4,6,7,12b-hexahydrobenzo[b]furo[2,3-a]quinolizin]-2,4'-imidazolidin-2'-one and 0.13 gram (1.1 mmol) of methanesulfonyl chloride are reacted together in dry pyridine and thereafter recovered from the reaction mixture to obtain (2RS,12bSR)-3'-(2-methanesulfonyloxyethyl)-spiro[1,3,4,6,7,12b-hexahydrobenzo[[b]furo[2,3-a]quinolizidin[2,4'-imidazolidin-2'-one.

EXAMPLE IIIA

In further operations, employing procedures similar to that described in Example III but employing initially a quinolizin-2-one of Formula VI, an appropriate alkenylamine and the appropriate RXCl in Step F, the compounds of Formula IA-2 and listed in Table III may be prepared.

TABLE III

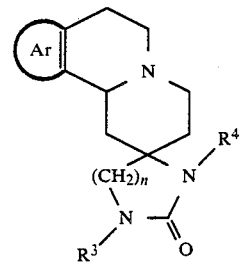

| Ar | $R^3$ | $R^4$ (RXOalkylene) | n |
|---|---|---|---|
| 10-chlorobenzo-[b]furo- | H— | $CH_3SO_2OCH_2CH_2$— | 1 |
| thieno- | H— | $CH_3COOCH_2CH_2$— | " |
| furo- | H— | $C_2H_5NHCOOCH_2CH_2$— | " |
| 11-hydroxybenzo-[b]]furo- | H— | $NH_2COOCH_2CH_2$— | " |
| 10,11-dimethyl-benzo[b]furo | H— | $N(CH_3)_2CSOCH_2CH_2$— | " |
| pyridino | H— | $NH_2SO_2OCH_2CH_2$— | " |
| imidazo | H— | $CH_3OCOOCH_2CH_2$— | " |
| benzo | H— | $CF_3SO_2OCH_2CH_2$— | " |
| benzo[b]thieno | H— | $CF_3COOCH_2CH_2$— | " |
| 10-methylbenzo-[b]thieno | H— | $(CH_3O)_2P(O)OCH_2CH_2$— | " |
| 9-methoxybenzo-[b]thieno | H— | $(NH_2)_2P(O)OCH_2CH_2$— | " |
| 11-fluorobenz-[b]furo | H— | $C_6H_5CH_2SO_2OCH_2CH_2$— | " |

TABLE III-continued

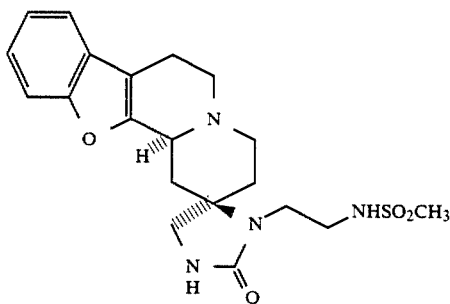

| Ar | R³ | R⁴ (RXOalkylene) | n |
|---|---|---|---|
| 9-bromobenzo-[b]furo₂- | H— | $C_6H_5COOCH_2CH_2$— | 1 |
| 11-methoxybenzo-[b]furo- | H— | $C_2H_5COOCH_2CH_2$— | " |
| benzo[b]furo- | H— | $CH_3SO_2OCH_2CH_2CH_2$ | " |
| benzo[b]thieno- | H— | $CH_3SO_2O(CH_2)_5$— | " |
| 9-methoxybenzo- | H— | $H_2NSO_2OCH(CH_3)CH_2$ | " |
| 4,5-dichlorothieno | H— | $CH_3SO_2OCH_2CH(CH_3)CH_2$— | " |

EXAMPLE IV (2RS,12bSR)-3'-(2-Methanesulfonamidoethyl)-spiro[1,3,4,6,7,12b-hexahydrobenzo[b]furo[2,3-a]quinolizin]-2,4'-imidazolidin-2'-one.

In reactions carried out in a manner similar to that described in Example II, Steps A, B and C, (2RS,12bSR)-3'-(2-methanesulfonyloxyethyl)-spiro[1,3,4,6,7,12b-hexahydrobenzo[b]furo[2,3-a]quinolizin]2,4'-imidazolidin-2'-one is reacted with sodium azide to obtain (2RS,12bSR)-3'-(2azidoethyl)-spiro-[1,3,4,6,7,12b-hexahydrobenzo[b]furo [2,3-a]quinolizin]-2,4'-imidazolidin-2'-one which is then hydrogenated over Pd/C to obtain (2RS,12bSR)-3'-(2-aminoethyl)-spiro[1,3,4,6,7,12 b-hexahydrobenzo[b-]furo[2,3-a]quinolizin]-2,4'-imidazolidin-2'-one which then is reacted with methanesulfonyl chloride in the presence of triethylamine to obtain (2RS,12bSR)-3'-(2-methanesulfonamidoethyl)-spiro[1,3,4,6,7,12b-hexahydrobenzo[b]furo[2,3-a]quinolizin[-2,4'-imidazolidin-2'-one.

EXAMPLE IVA (2R,12bS)-3'-(2-Methanesulfonamidoethyl)-spiro[1,3,4,6,7,12b-hexahydrobenzo[b]furo[2,3-a]quinolizin]-2,4'-imidazolidin-2'-one The title compound chemically identical to that of Example IV, amy also be prepared by the following method:

Step A: Preparation of 2-methanesulfonylaminoethylacetamide 11.86 grams (104 mmol) of methanesulfonyl chloride was added to a solution of 10.2 grams (100 mmol) of acetylethylenediamine and 10.5 grams (104 mmol) of triethylamine in cold (0° C.) methylene chloride and the mixture was stirred for 3 hours. At the end of this period, the mixture was concentrated to obtain a residue. To the residue was added 500 milliliters of ammonia saturated chloroform, the resulting mixture was filtered to removed undesired by-product and the filtrate was concentrated to obtain 14.5 grams (80 percent yield) of 2-methanesulfonylaminoethylacetamide.

Step B: Preparation of 2-(aminoethyl)methanesulfonamide 14.5 grams (80.55 mmol) of 2-methanesulfonylaminoethylacetamide was heated in 200 milliliters of 6N hydrochloric acid solution at 110° C. for three hours. At the end of this period, the reaction mixture was concentrated to obtain a residue. The latter was dissolved in 500 milliliters of methanol and to the solution was added a sufficient amount of Amberlite IRA 400 basic resin to render the solution basic. The mixture was filtered and the filtrate concentrated to obtain 11.1 grams (98%) of the desired 2-(aminoethyl)methanesulfonamide intermediate as a viscous oil.

Step C: Preparation of (2R,12bS)-2-cyano-2-(2-methanesulfonamidoethyl-)amino-1,3,4,6,7,12b-hexahydrobenzo[b]furo[2,3-a]quinolizine 420 milligrams (3.04 mmol) of 2-aminoethylmethanesulfonamide was added to a solution of 350 milligrams (1.45 mmol) of (12bS)-1,3,4,6,7,12b-hexahydrobenzo[b]furo[2,3-a]quinolizin-2-one in 10 milliliters of methanol and 50 milliliters of tetrahydrofuran. Then, 370 milligrams (2.28 mmol) of diethyl cyanophosphonate was added and the resulting mixture allowed to stand at room temperature for three hours to form (2R,12bS)-2-cyano-2-(2-methanesulfonamidoethyl-)amino-1,3,4,6,7,12b-hexahydrobenzo[b]furo[2,3-a]quinolizine intermediate in the reaction mixture. The mixture was concentrated and the residue chromatographed on silica gel employing 10 percent methanol in ethyl acetate as eluant to obtain 453 milligrams of the purified product. [α]=−41° (MeOH, C=0.001)

Step D: Preparation of (2R,12bS)-2-aminomethyl-2-(2-methanesulfonamidoethyl)amino-1,3,4, 6,7,12b-hexahydrobenzo[b]furo[2,3-a]quinolizine A solution of 430 milligrams (1.11 mmol) of (2R,12bS)-2-cyano-2-(2-methanesulfonamidoethyl-)amino-1,3,4,6,7,12b-hexahydro[b]furo[2,3-a]quinolizine in 7 milliliters of tetrahydrofuran was added to a cooled to 0° C. solution of 85 milligrams (2.22 mmol) of lithium aluminum hydride in 60 milliliters of ether. The resulting mixture was stirred for 1.5 hours, then quenched with water, filtered through a pad of celite, the pad washed with methanol and methylene chloride. The filtrate was dried over sodium sulfate, then filtered and the filtrate concentrated to obtain crude intermediate product which was chromatographed on silica gel and eluted with 10 percent methanol/ammonia saturated chloroform to obtain 315 milligrams of the desired (2R,12bS)-2-aminoethyl-2-(2-methanesulfonamidoethyl)amino-1,3,4,6,7,12b-hexahydrobenzo[b]furo[2,3-a]quinolizine intermediate. [α]=−60° (MeOH, C=0.001)

Step E: Preparation of (2R,12bS)-3'-(2-methanesulfonamidoethyl)-spiro-[1,3,4,6,7,12b-hexahydrobenzo[b]furo[2,3-a]quinolizin]-2,4'-imidazolidin-2'-one 130 milligrams (0.80 mmol) of carbonyldiimidazole was added to a solution of 305 milligrams (0.778 mmol) of (2R,12bS)-2-aminoethyl-2-(2-methanesulfonamidoethyl)amino-1,3,4,6,7,12b-hexahydrobenzo[b]furo[2,3-a]quinolizine in 10 milliliters of methylene chloride. The reaction mixture was allowed to stand for 5 hours at room temperature to complete the reaction with the formation of (2R,12bS)-3'-(2-methanesulfonamidoethyl)-spiro-[1,3,4,6,7,12b-hexahydrobenzo[b]furo[2,3-a]quinolizin]-2,4'-imidazolidin-2'-one product in the reaction mixture. The product was recovered by washing the mixture with water, drying the organic solution, filtering drying agent, and concentrating to obtain a residue of crude product. The latter was chromatographed on silica gel employing 10 percent methanol/ethyl acetate as eluant to obtain 268 milligrams of purified product. The hydrochloride salt was prepared and had a melting point of 290°-292° C. [α]=−42° (MeOH, C=0.001)

EXAMPLE IV-B

In further operations, employing the compounds of Table I in Example I as starting materials and a procedure similar to that described in Example II, Steps A, B and C, but substituting R-X-Cl for methanesulfonyl chloride in Step C, there are prepared the imidazolidin-2-ones of Formula Ib-2 as seen in Table IV.

The compounds of Formula IB-2 in Table IV may also be prepared in accordance with Examples IVA by preparing RXNalkyleneNH₂ instead of 2-aminoethyl-methanesulfonamide prepared in Steps A and B, and thereafter carrying out the reactions as described in Steps C, D, and E.

TABLE IV

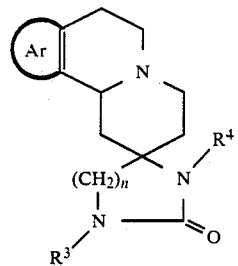

| Ar | $R^3$ | $R^4$ (RXNalkylene) | n |
|---|---|---|---|
| 10-chlorobenzo[b]furo- | H— | CH₃SO₂NCH₂CH₂— | 1 |
| thieno- | H— | CH₃CONCH₂CH₂— | " |
| furo- | H— | C₂H₅NHCONCH₂CH₂— | " |
| 11-hydroxybenzo[b]furo- | H— | NH₂CONCH₂CH₂— | " |
| pyridino | H— | C₂H₅CONCH₂CH₂— | " |
| imidazo | H— | C₂H₅SO₂NHCH₂CH₂— | " |
| benzo | H— | C₆H₅CONHCH₂CH₂ | " |
| 9-methoxybenzo[b]thieno | H— | (CH₃)₂NCSNHCH₂CH₂— | " |
| thiazolo | H— | NH₂SO₂NHCH₂CH₂— | " |
| pyrazolo | H— | CF₃SO₂NHCH₂CH₂— | " |
| benzo[b]thieno | H— | C₆H₅SO₂NHCH₂CH₂— | " |
| 10-methylbenzo- | H— | (CH₃O)₂P(O)NHCH₂CH₂— | " |

TABLE IV-continued

| Ar | $R^3$ | $R^4$ (RXNalkylene) | n |
|---|---|---|---|
| [b]thieno | | | |
| 9-bromobenzo-[b]furo) | H— | (NH₂)₂P(O)NHCH₂CH₂— | " |
| benzo[b]furo- | H— | CH₃SO₂NHCH₂CH₂CH₂— | " |
| benzo[b]thieno- | H— | H₂NSO₂NH(CH₂)₅— | " |
| 9-methoxybenzo- | H— | CH₃SO₂NHCH(CH₃)CH₂— | " |
| 4,5-dichlorothieno- | H— | CH₃SO₂NHCH₂CH(CH₃)CH₂— | " |

EXAMPLE V (2SR,12bSR)-1,3,4,5',6,6',7,12n-Octahydro-3'-methyl-1'-(2-methanesulfonyloxyethyl)-spiro(2H-benzofuro-[2,3-a]quinolizine-2,4'-(1'H-pyrimidin-2'(3'H)-one)

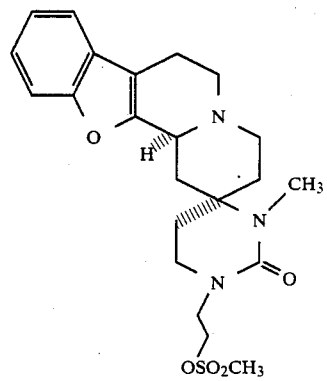

Step A: Preparation of (E,Z)-2-Carbomethoxymethylidine-1,3,4,6,7,12b-hexahydrobenzo[b]furo[2,3-a]quinolizine to a 200 milliliter round bottomed flask was added with stirring and cooling under argon, 2.84 grams of a 35% suspension of potassium hydride in mineral oil. The oil was removed with two washings of a mixture of hexanes and then 15 milliliters of dry tetrahydrofuran was added. The stirring suspension was cooled to 0° C. and trimethylphosphonoacetate (4.53 g) was added, neat, dropwise. After this viscous mixture had stirred for 10 minutes a solution of 2.00 g of 1,3,4,6,7,12b-hexahydrobenzo[b]furo[2,3-a]quinolizin-2-one in 15 milliliters of dry tetrahydrofuran was added with a syringe and the resulting mixture was stirred overnight at room temperature. The reaction mixture was diluted with 200 milliliters of water and extracted with ethyl acetate (3×100 ml). The combines ethyl acetate extracts were washed with water and brine, dried over magnesium sulfate, filtered, and concentrated in vacuo. The crude product was chromatographed on 150 grams of silica gel with 25% ethyl acetate in hexane mixture as eluant.

This procedure provided 1.25 grams of the faster eluting E isomer and 1.12 grams of the slower eluting Z isomer. The free bases were converted to their HCl salts by the usual method: E-isomer; m.p. 218°–129° C.: Z-isomer; m.p. 220°–221° C.

The (12bR)- and (12bS)-enantiomers of the title compound were prepated by starting with the enantiomers of the quinolizin-2-one.

Step B: Preparation of (2RS,12bSR)-N-methyl(2-methylamino-1,3,4,6,7,12b-hexahydrobenzo[b]furo[2,3-a]quinolizin-2-yl)acetate 3 Grams (10 millimoles) of (E,Z)-2-carbomethoxymethylidene-1,3,4,6,7,12b-hexahydrobenzo[b]furo[2,3-a]quinolizine in 20 milliliters of ethanol was placed in a pressure bottle and the solution was cooled to −78° C. with a dry ice/acetone bath. Methylamine (20 ml) was condensed into the vessel which was then sealed and allowed to stir at room temperature for 4 hours. The pressure was released and the solvent removed in vacuo to yield 2.7 g (85%) (2RS,12bSR)-N-methyl-(2-methylamino-1,3,4,6,7, 12b-hexahydrobenzo[b]furo[2,3-a]quinolizin-2-yl)acetate as a yellow oil.

The (12bR)- and (12bS)-enantiomers of the (2RS,12bSR)- title compounds were prepared by starting with the enantiomers of the carbomethoxymethylidene compound described in Step B. Step C: Preparation of (2RS,12bSR)-N-(2-propenyl)-2-(2-methylamino-1,3,4,6,7,12b-hexahydrobenzo[b]furo[2,3-a]quinolozin-2-yl)acetamide A mixture of 2.6 grams (8 mmol) of (2RS,12bSR)-methyl-2-(2-methylamino-1,3,4,6,7,12b-hexahydrobenzo[b]furo[2,3-a]quinolizin -2-yl)acetate, 50 ml allylamine and 50 ml absolute ethanol were refluxed for 3 days. The reaction was cooled and the solvent removed in vacuo to give 1.8 grams (63.7%) of (2RS,12bSR)-N-(2-propenyl)-2-(2-methylamino-1,3,4,6,7,12b-hexahydrobenzo[b]furo[2,3-a]quinolizin-2-yl)acetamide as a yellow oil after medium pressure column chromatography using ammonia/saturated chloroform as eluant.

Step D: Preparation of (2SR,12bSR)-2-methylamino-2-(2-(2-propenylamino)ethyl)-1,3,4,6,7,12b-hexahydrobenzo[b]furo[2,3-a]quinolizine Employing the procedure substantially as described in Example III, Step B, 1.8 grams (5 mmol) of (2RS,12bSR)-N-(2-propenyl)-2-(2-methylamino-1,3,4,6,7,12b-hexahydrobenzo[b]furo[2,3-a]quinolizin-2-yl)acetamide and 6 ml(20 mmol) of 3.4M sodium bis (2-methoxyethoxy)aluminum hydride were reacted to obtain 1.2 g (70.7%) of (2RS,12bSR)-2-methylamino-2-(2-(2-propenylamino)ethyl)-1,3,4,6,7,12b-hexahydrobenzo[b]furo[2,3-a]quinolizine as a yellow oil after medium pressure column chromatography (ammonia/-saturated chloroform eluant).

Step E. Preparation of (2SR,12bSR)-1,3,4,5′,6,6′,7,-12b-octahydro-1′-(2-propenyl)-3′-methyl-spiro(2H-benzofuro[2,3-a]quinolizin)-2,4′-(1′H-pyrimidin-2′(3′H)-one)

Employing the procedure substantially as described in Example III, Step C, 1.2 grams (3.5 mmol) of (2RS,12bSR)-2-methylamino-2-(2-(2-propenyl amino)ethyl)-1,3,4,6,7,12b-hexahydrobenzo[b]furo[2,3-a]quinolizine and 1.14 grams (7 mmol) of 1,1′-carbonyldiimidazole were reacted to obtain 0.8 gram (63%) of (2SR,12bSR)-1,3,4,5′,6,6′,7,12b-octahydro-1′-(2propenyl)-3′-methyl-spiro (2H-benzofuro[2,3-a]quinolizin)-2,4′-(1′H-pyrimidin-2′(3′H)-one) as a yellow waxy solid after purification by flash column chromatography, from which was made the hydrochloride dihydrate salt, m.p. 174°–176° C.

Step F: Preparation of (2SR,12bSR)-1,3,4,5′, 6,6′,7,12b-octahydro-3′-methyl-1′-(2,3-dihydroxypropyl)-spiro(2H-benzofuro[2,3-a]quinolizine)-2,4′(1′H-pyrimidin-2′(3′H)-one)

Employing the procedure substantially as described in Example III, Step D, a mixture of 0.1 g (0.27 mmol) of (2SR,12bSR)-1,3,4,5′, 6,6′, 7,12b-octahydro-1′-(2propenyl)-3′-methyl-spiro(2H-benzofuro[2,3a]-quinolizin)-2,4′(1′H-pyrimidin-2′(3′H)-one), 0.07 3 g (0.54 mmol) of 4-methylmorpholine-4-oxide monohydrate and 2 drops of osmium tetroxide (0.4M solution in tetrahydrofuran) were reacted to give 0.06 g (55%) of (2SR,12bSR)-1,3,4,5′,6,6′,7,12b-octahydro -3′-methyl1′-(2,3-dihydroxypropyl)-spiro (2H-benzofuro[2,3-a]quinolizine)-2,4′(1′H-pyrimidin-2′(3′H)-one) as a waxy solid after purification by flash column chromatography (ammonia saturated chloroform), from which was made the hydrochloride dihydrate salt, m.p. 175°–177° C. (dec).

Step G: Preparation of (2SR,12bSR)-1,3,4,5′, 6,6′,7,12b-octahydro-3′-methyl-1′-(2-hydroxyethyl)-spiro(2H-benzofuro[2,3-a]quinolizine) -2,4′-(1′H-pyrimidin-2′(3′H)-one)

A mixture of 0.125 g (0.31 mmol) of (2SR, 12bSR)-1,3,4,5′,6,6′,7,12b-octahydro-3′-methyl-1′-(2,3-dihydroxypropyl)-spiro(2H-benzofuro[2,3-a]quinolizine)-2,4′(1′H-pyrimidin-2′(3′H)-one) and 0.125 milliliter 20% NaOH were dissolved in 10 ml 95% ethanol and cooled to 0° C. To this.solution was added 0.2 gram (0.93 mmol) of sodium periodate dropwise in 5 milliliters H₂O. The reaction was allowed to stir for 2 hours at 0° C., then the solvent was removed and the residue was partitioned between water/chloroform. The layers were separated, the organics dried (MgSO₄) and the solvent removed to give the crude aldehyde which was immediately dissolved in 10 milliliters absolute ethanol and treated with a large excess (0.15 g) of sodium borohydride. After stirring 18 hours, the solvent was removed and the residue worked up to obtain 0.048 gram (42%) of (2SR,12bSR)-1,3,4,5′,6,6′,7,12b-octahydro-3′-methyl-1′-(2-hydroxyethyl)-spiro(2H-benzofuro[2,3-a]quinolizine)-2,4′(1′H-pyrimidin-2′-(3′H)-one) as a white crystalline solid m.p. 174°–176° C.

Step H: Preparation of (2SR,12bSR)-1,3,4,5′,6,6′,7,12b-octahydro-3′-methyl-1′-(2-methanesulfonyloxtethyl)-spiro(2H-benzofuro[2,3-a]quinolizine-2,4′-(1′H-pyrimidin-2′-(3′H)-one)

A mixture of 0.036 gram (0.096 mmol) of (2SR,12bSR)-1,3,4,5′,7,12b-octahydro-3′-methyl-1′-(2-hydroxyethyl)-spiro(2H-benzofuro[2,3-a]quinolizine)-2,4′-(1′H-pyrimidin-2′-(3′H)-one) and methanesulfonyl chloride (0.022 g, 0.015 mmol) in dry pyridine (10 ml) were stirred 24 hours, after which time the solvent was removed in vacuo and the residue partitioned between water/chloroform. The organic layer was separated, washed with water and dried over NaSO₄ and the dried solution concentrated and then purified by spinning disc chromatography with 5% methanol/chloroform eluant to obatin 0.033 gram (82% yield) of (2SR,12bSR)-1,3,4,5′,6,6′,7,12b-octahydro-3′-methyl-1′-(2- methanesulfonyloxyethyl)-spiro(2H-benzofuro[2,3-a]quinolizine-2,4'-(1'H-pyrimidin-2'-(3'H)-one) product.

EXAMPLE V-A

In preparation carried out in a similar manner but substituting for 1,3,4,6,7,12b-hexahydrobenzo[b]furo[2,3-a]quinolizin-2-one an appropriate quinolizin-2-one of Formula VI, and by substituting an appropriate $R^3NH_2$ in Step B and an appropriate alkenylamine in Step C and an appropriate R-X-Cl in Step H, the compounds of the following Table V may be prepared.

(2-methanesulfonyloxyethyl)-spiro(2H-benzofuran[2,3-a]quinolizine-2,4'-(1'H-pyrimidin-2'-(3'H)one) obtained as described in Example V is reacted with sodium azide in N,N-dimethylformamide to obtain (2RS,12bSR)-1'-(2-azidoethyl)-3'-methyl-spiro[ 1,3,4,6,7,12b-hexahydrobenzo[b]furo[2,3-a]quinolizin-2,4'-(1'H-pyrimidin-2'-(3'H)-one which is then hydrogenated in the presence of Pd on C catalyst to obtain (2RS,12bSR)-1'-(2-aminoethyl)-3'-methyl-spiro[1,3,4,6,7,12b-hexahydrobenzo[b]furo[2,3-a]quinolizin-2,4'-(1'H-pyrimidin-2'-(3'H)-one which is then reacted with methanesulfonyl chloride to

TABLE V

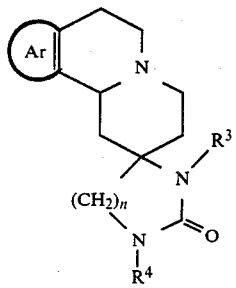

| Ar | $R^3$ | $R^4$ (RXOalkylene) | n |
|---|---|---|---|
| 10-chlorobenzo[b]furo- | $CH_3$— | $CH_3SO_2OCH_2CH_2$— | 2 |
| thieno- | H— | $C_2H_5COOCH_2CH_2$— | " |
| furo- | $C_2H_5$— | n-$C_3H_7NHCOOCH_2CH_2$— | " |
| 11-hydroxybenzo[b]]furo- | $C_3H_7$— | $C_6H_5COOCH_2CH_2$— | " |
| 10,11-dimethylbenzo[b]furo- | $CH_3$— | $C_6H_5CH_2SO_2OCH_2CH_2$— | " |
| pyridino- | $CH_3$— | $CF_3SO_2OCH_2CH_2$— | " |
| imidazo | $CH_3$— | $NH_2SO_2OCH_2CH_2$— | " |
| benzo | $CH_3$— | $(CH_3)_2NCSOCH_2CH_2$— | " |
| benzo[b]-thieno- | $CH_3$— | $CF_3COOCH_2CH_2$— | " |
| 10-methylbenzo[b]thieno- | $CH_3$— | $(CH_3O)_2P(O)OCH_2CH_2$— | " |
| 9-methoxybenzo[b]thieno- | H— | $(NH_2)_2P(O)OCH_2CH_2$— | " |
| 11-fluorobenzo[b]furo- | H— | $NH_2COOCH_2CH_2$— | " |
| 9-bromobenzo[b]furo-2 | $C_6H_5CH_2$— | $CH_3COOCH_2CH_2$— | " |
| 11-methoxybenzo[b]furo- | H— | $C_2H_5COOCH_2CH_2$— | 2 |
| thiazolo- | $CH_3$— | $CF_3COOCH_2CH_2$— | " |
| pyrazolo- | $CH_3$— | $C_3H_7COOCH_2CH_2$— | " |
| benzo[b]furo- | $CH_3$— | $CH_3SO_2OCH_2CH_2CH_2$— | " |
| benzo[b]thieno- | H— | $CH_3SO_2OCH(CH_3)CH_2$— | " |
| 9-methoxybenzo- | $CH_3$— | $H_2NSO_2O(CH_2)_5$— | " |
| 4,5-dichlorothieno- | $CH_3$— | $CH_3SO_2CH_2CH(CH_3)CH_2$— | " |

EXAMPLE VI (2SR,12bSR)-1,3,4,5',7,12b-Octahydro-3'-methyl-1'-(2-methanesulfonamidoethyl)-spiro(2H-benzofuro[2,3-a]quinolizine-2,4'-(1'H-pyrimidin-2'-(3'H)-one)

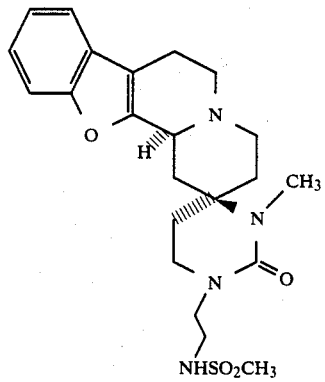

In reactions carried out in substantially the same manner described in Example II, Steps A, B and C, (2SR,12bSR)-1,3,4,5',6,6',7,12b-octahydro-3'-methyl-1'- obtain (2SR,12bSR)-1,3,4,5',7,12b-octahydro-3'-methyl-1'-(2-methanesulfonamidoethyl)-spiro(2H-benzofuro[2,3-a]quinolizine-2,4'-(1'H-pyrimidin-2'-(3'H)-one).

EXAMPLE VIA

Employing procedures substantially as above-described but substituting for (2RS,12bSR)-1'-(2-aminoethyl)-3'-methyl-spiro-[1,3,4,6,7,12b-hexahydrobenzo[b]furo[2,3-a]quinolizin-2,4'-(1'H-pyrimidin-2'-(3'H)-one, the amine compounds of Formula V produced from the methanesulfonyl esters as obtained in Example V and substituting for methane sulfonyl chloride, the appropriate R-X-Cl, the compounds of the following Table VI may be prepared.

TABLE VI

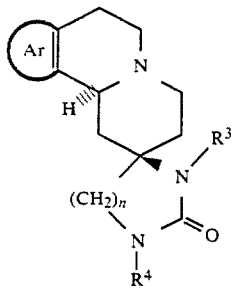

| Ar | R³ | R⁴ (RXNHalkylene) | n |
|---|---|---|---|
| 10-chlorobenzo[b]furo- | $CH_3-$ | $CH_2SO_2NHCH_2CH_2-$ | 2 |
| thieno- | $H-$ | $C_2H_5CONHCH_2CH_2-$ | " |
| furo- | $C_2H_5-$ | $n\text{-}C_3H_7NCONHCH_2CH_2-$ | " |
| 11-hydroxybenzo[b]]furo- | $C_3H_7-$ | $C_6H_5CONHCH_2CH_2-$ | " |
| 10,11-dimethylbenzo[b]furo- | $CH_3-$ | $C_6H_5CH_2SO_2NHCH_2CH_2-$ | " |
| pyridino- | $CH_3-$ | $CF_3SO_2NHCH_2CH_2-$ | " |
| imidazo | $CH_3-$ | $NH_2SO_2NHCH_2CH_2-$ | " |
| benzo | $CH_3-$ | $(CH_3)_2NCSNHCH_2CH_2-$ | " |
| benzo[b]-thieno- | $CH_3-$ | $CF_3CONHCH_2CH_2-$ | " |
| 10-methylbenzo[b]thieno- | $CH_3-$ | $(CH_3O)_2P(O)NHCH_2CH_2-$ | " |
| 9-methoxybenzo[b]thieno- | $H-$ | $(NH_2)_2P(O)NHCH_2CH_2-$ | " |
| 11-fluorobenzo[b]furo- | $H-$ | $NH_2CONHCH_2CH_2-$ | " |
| 9-bromobenzo[b]furo- | $C_6H_5CH_2-$ | $CH_3CONHCH_2CH_2-$ | 2 |
| 11-methoxybenzo[b]furo- | $H-$ | $C_2H_5CONHCH_2CH_2-$ | " |
| thiazolo- | $CH_3-$ | $CF_3CONHCH_2CH_2-$ | " |
| pyrazolo- | $CH_3-$ | $C_3H_7CONHCH_2CH_2-$ | " |
| benzo[b]furo- | $CH_3-$ | $CH_3SO_2NHCH_2CH_2CH_2-$ | " |
| benzo[b]thieno- | $CH_3-$ | $CH_3SO_2NH(CH_2)_5-$ | " |
| 9-methoxybenzo- | $CH_3-$ | $H_2NSO_2NHCH(CH_3)CH_2-$ | " |
| 4,5-dichlorothieno | $H-$ | $CF_3CONHCH_2CH(CH_3)CH_2-$ | " |

EXAMPLE VII (2SR,12bSR)-1,3,4,5',6,6'7,12b-Octahydro-1'-methyl-3'-(2-methanesulfonyloxyethyl)-spiro(2H-benzofuro[2,3-a]quinolizine-2,4'(1'-H-pyrimidin)-2'(3'H)-one)

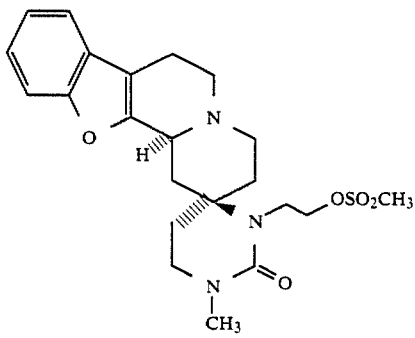

Step A: Preparation of (2RS,12bSR)Methyl 2-(2-(2-propenylamino)-1,3,4,6,7,12b-hexahydrobenzo[b]furo[2,3-a]quinolizin-2-yl)acetate A mixture of 0.148 gram (0.5 mmol) of (E,Z)-2-carbomethoxymethylidene-1,3,4,6,7,12b-hexahydrobenzo[b]furo[2,3-a]quinolizine, 5 ml of allylamine and 5 ml absolute ethanol were refluxed under a nitrogen atmosphere for 18 hours, after which the solvent was removed and the resulting residue purified by spinning disc chromatography (1:1 hexane/ammonia saturated chloroform) to obtain 0.063 gram (36%) of (2SR,12bSR)methyl(2-(2-propenylamino)-1,3,4,6,7,12b-hexahydrobenzo[b]furo[2,3-a]quinolizin-2-yl) acetate as a yellow oil.

Step B: Preparation of (2RS,12bSR)-N-methyl-2-(2-(2-propenyl amino)-1,3,4,6,7,12b-hexahydrobenzo[b]furo[2,3-a]quinolizin-2-yl)acetamide A mixture of 0.86 g (2.4 mmol) of (2RS,12bSR-methyl-2-(2-(2-propenylamino)-1,3,4,6,7,12b-hexahydrobenzo[b]furo[2,3-a]quinolizin-2-yl)acetate and dry methylamine where reacted employing the procedure substantially as described in Example V, Step B to obtain (2RS,12bSR)-N-methyl-2-(2-(2-propenylamino)-1,3,4,6,7,12b-hexahydrobenzo[b]furo[2,3-a]-quinolizin-2-yl)acetamide (0.5 g, 58%) as a yellow oil after purification by medium pressure column chromatography (ammonia saturated chloroform).

Step C: Preparation of (2RS,12bSR)-2-(2-propenylamino)-2-(2-methylaminoethyl)-1,3,4,6,7,12b-hexahydrobenzo[b]furo[2,3-a]quinolizine A mixture of 1.66 ml (5.6 mmol) of 3.4M sodium bis (2-methoxyethoxy)aluminum hydride and 0.5 g (1.4 mmol) of (2RS,12bSR)-N-methyl-2-(2-(2-propenylamino)-1,3,4,6,7,12b-hexahydrobenzo[b-]furo[2,3-a]quinolizin-2-yl)acetamide were reacted employing the procedure substantially as described in Example V, Step D to yield 0.116 g (24%) of (2RS,12bSR)-2-( 2-propenylamino)-2-(2-methylaminoethyl)-1,3,4,6,7,12b-hexahydrobenzo[b]furo[2,3-a]quinolizine as a yellow oil after purification by spinning disc chromatography (3% methanol/ammonia saturated chloroform).

Step D: Preparation of (2SR,12bSR)-1,3,4,5',6,6',7-12b-octahydro-1'-methyl-3'-(2-propenyl)spiro(2H-benzofuro[2,3-a]quinolizin)-2,4'-(1'H-pyrimidin-2'(3'H)-one)

A mixture of 0.116 g (0.34 mmol) of (2RS,12bSR)-2-(2-propenylamino)-2-(2-methylaminoethyl)1,3,4,6,7,12b-hexahydrobenzo[b]furo[2,3-a]quinolizine and 0.11 g (0.68 mmol) 1,1'-carbonyldiimidazole in 20 ml was reacted employing the procedure substantially as described in Example V, Step E to obtain 0.063 g (51%) of (2RS,12bSR)-1,3,4,5',6,6',7,12b-octahydro-1'-methyl-3'-(2-propenyl)-spiro(2H-benzofuro[2,3-a]quinolizin)-2,4'(1'H-pyrimidin-2'(3'H)-one) after purification by spinning disc chromatography (ammonia saturated chloroform), from which was made the hydrochloride dihydrate salt, m.p. 173°–175° C. (dec).

Step E: Preparation of (2SR,12bSR)-1,3,4,5',6,6',7,12b-octahydro-1'-methyl-3'-(2,3-dihydroxypropyl)-spiro-(2H-benzofuro[2,3-a]quinolizine)-2,4'(1'H-pyrimidin-2'(3'H)-one)

A mixture of 0.1 g (0.27 mmol) of (2RS,12bSR)-1,3,4,5',6,6',7,12b-octahydro-1'-methyl-3'-(2-propenyl)-spiro(2H-benzofuro[2,3-a]quinolizine)-2,4'(1'-pyrimidin-2'(3'H)-one) and 0.73 g (0.54 mmol) 4-methylmorpholine-4-oxide monohydrate were dissolved in 25 ml THF, and to this was added 2 drops of a 0.4M solution of osmium tetroxide in THF. The reaction was stirred 18 hours after which time it was poured into 50 ml water and extracted with 3×25 ml chloroform. The organic layer was dried (MgSO4) and the solvent removed to give 0.08 g (74.4%) of (2SR,12bSR-1,3,4,-5',6,6',7,12b-octahydro-1'-methyl-3'-(2,3-dihydroxypropyl)spiro(2H-benzofuro[2,3-a]quinolizine)-2,4'(1'H-pyrimidin-2'(3'H)-one) after flash column chromatography (ammonia saturated chloroform), from which was made the hydrochloride dihydrate salt. m.p. 175°–178° C.

Step F: Preparation of (2SR,12bSR)-1,3,4,5'6,6',7,12b-octahydro-3'-(2-hydroxyethyl)-1'-methylspiro(2H-benzofuro[2,3-a]quinolizine)-2,4'-(1'H-pyrimidin-2'(3'H)-one)

A mixture of 0.05 g (0.12 mmol) of (2SR,12bSR)-1,3,4,5',6,6'7,12b-octahydro-1'-methyl-3'-(2,3-dihydroxypropyl)-spiro(2H-benzofuro[2,3-a]quinolizin)-2,4'-(1'H-pyrimidin-2'(3'H)-one), 0.079 g (0.36 mmol) of sodium periodate and 0.05 ml 20% NaOH are reacted followed by a large excess of sodium borohydride employing the procedure substantially as described in Example V, Step G to obtain 0.026 g (58.6%) of (2SR,12bSR)-1,3,4,5',6,6',7,12b-octahydro-3'-(2-hydroxyethyl)-1'-methyl-spiro(2H-benzofuro[2,3-a]quinolizine)-2,4'(1'H-pyrimidin-2'(3'H)-one) as a white crystalline solid, m.p. 212°–213° C.

Step G: Preparation of (2SR,12bRS)-1,3,4,5',6,6',7,12b-octahydro-3'-(2-methanesulfonyloxyethyl)1'-methyl-spiro(2H-benzofuro[2,3-a]quinolizin)2,4'-(1H'-pyrimidin-2'-(3H')-one)

Following substantially the same procedure described in Example V, Step H, (2SR,12bSR)1,3,4,5',6,6',7,12b-octahydro-3'-(2-hydroxyethyl)1'-methyl-spiro(2H-benzofuro[2,3-a]quinolizine)2,4'-(1H'-pyrimidin-2'-(3H')-one) and methanesulfonyl chloride are reacted in dry pyridine to obtain (2SR,12bSR)-1,3,4,5',6,6',7,12b-octahydro-1'-methyl3'-methanesulfonyloxyethyl)-spiro(2H-benzofuro[2,3-a]quinolizine-2,4'-(1'H-pyrimidin)-2'-(3'H)-one.

EXAMPLE VII-A

In operations carried out in a manner similar to that described above in Example VII but employing the appropriate intermediate of Formula V and the appropriate alkenylamine, $R^3NH_2$, and R-X-Cl, the compounds of Table VII may be prepared.

TABLE VII

| Ar | $R^3$ | $R^4$ (RXOalkylene) | n |
|---|---|---|---|
| 10-chlorobenzo[b]furo- | $CH_3-$ | $CH_3SO_2OCH_2CH_2-$ | 2 |
| thieno- | $H-$ | $CF_3COOCH_2CH_2-$ | " |
| furo- | $C_2H_5-$ | $C_6H_5COOCH_2CH_2-$ | " |
| 11-hydroxybenzo[b]]furo- | $C_3H_7-$ | $C_6H_5SO_2OCH_2CH_2-$ | " |
| 10,11-dimethylbenzo[b]furo- | $CH_3-$ | $NH_2SO_2OCH_2CH_2-$ | " |
| pyridino- | $CH_3-$ | $(CH_3)_2NCSOCH_2CH_2-$ | " |
| imidazo | $CH_3-$ | $CF_3COOCH_2CH_2-$ | " |
| benzo | $CH_3-$ | $C_6H_5CH_2COOCH_2CH_2-$ | " |
| benzo[b]-thieno- | $CH_3-$ | $C_6H_5COOCH_2CH_2-$ | " |
| 10-methylbenzo[b]thieno- | $CH_3-$ | $C_2H_5COOCH_2CH_2-$ | " |
| 9-methoxybenzo[b]thieno- | $H-$ | $CH_3COOCH_2CH_2-$ | " |
| 11-fluorobenzo[b]furo- | $H-$ | $CF_3COOCH_2CH_2-$ | " |
| 9-bromobenzo[b]furo- | $C_6H_5CH_2-$ | $C_6H_5COOCH_2CH_2-$ | " |
| 11-methoxybenzo[b]furo- | $H-$ | $CF_3COOCH_2CH_2-$ | " |
| thiazolo- | $CH_3-$ | $C_6H_5COOCH_2CH_2-$ | " |
| pyrazolo- | $CH_3-$ | $C_6H_5SO_2OCH_2CH_2-$ | " |

TABLE VII-continued

| Ar | R³ | R⁴ (RXOalkylene) | n |
|---|---|---|---|
| benzo[b]furo- | CH₃— | CH₃SO₂OCH₂CH₂CH₂— | " |
| benzo[b]thieno- | CH₃— | CH₃SO₂O(CH₂)₅— | " |
| 9-methoxybenzo- | CH₃— | H₂NSO₂OCH(CH₃)CH₂— | " |
| 4,5-dichlorothieno | CH₃— | CF₃COOCH₂CH(CH₃)CH₂— | " |

EXAMPLE VIII (2SR,12bSR)-1,3,4,5',6,6',7,12b-Octahydro-3'-(2-methanesulfonamidoethyl)-1'-methyl-spiro(2H-benzofuro[2,3-a]quinolizine)-2,4'-(1H'-pyrimidin-2'-(3H')one)

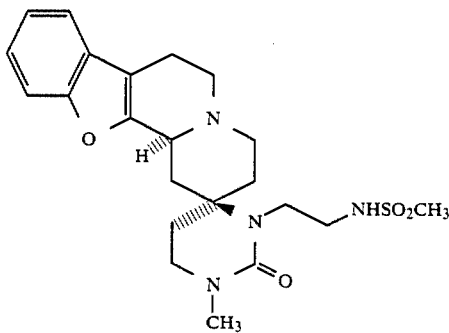

In operations carried out substantially as described in Example II, Steps A, B and C, (2SR,12bSR)-1,3,4,5',6,6',7,12b-octahydro-3'-(2-methanesulfonyloxyethyl)-1'-methyl-spiro(2H-benzofuro[2,3-a]quinolizine)-2,4'-(1H'-pyrimidine-2'(3H)-one) obtained as described in Example VII is reacted with sodium azide in dimethylformamide to obtain (2SR,12bSR)-1,3,4,5,6,6',7,12b-octahydro-3'-(2-azidoethyl)-1'-methyl-spiro[1,3,4,6,7,12b-hexahydrobenzo[b]furo[2,3-a]quinolizin]-2,4'-(1H'-pyrimidine-2'(3H)-one) which is then hydrogenated in the presence of Pd on C catalyst to obtain (2RS,12bSR)-3'-(2-aminoethyl)-1'-methyl-spiro-[1,3,4,6,7,12b-hexahydrobenzo[b]furo[2,3-a]quinolizin-2,4'-(1'H-pyrimidin-2'(3'H)-one which is then reacted with methanesulfonyl chloride to obtain (2SR,12bSR)-1,3,4,5',6,6',7,12b-octahydro-3'-(2-methanesulfonamidoethyl)-1'-methyl-spiro(2H-benzofuro[2,3-a]quinolizine-2,4'-(1'H-pyrimidin-2'(3'H)-one.

EXAMPLE VIII-A

Employing procedures substantially as above-described but substituting for the amine, the amines produced from the methanesulfonyl esters as obtained in Example VII and substituting the appropriate R³NH₂ and R-X-Cl, the compounds of the following Table VIII may be prepared.

TABLE VIII

| Ar | R³ | R⁴ (RXOalkylene) | n |
|---|---|---|---|
| 10-chlorobenzo[b]furo- | CH₃— | CH₃SO₂NHCH₂CH₂— | 2 |
| thieno- | H— | CF₃CONHCH₂CH₂— | " |
| furo- | C₂H₅— | C₆H₅CONHCH₂CH₂— | " |
| 11-hydroxybenzo[b]]furo- | C₃H₇— | C₆H₅SO₂NHCH₂CH₂— | " |
| 10,11-dimethylbenzo[b]furo- | CH₃— | NH₂SO₂NHCH₂CH₂— | " |
| pyridino- | CH₃— | (CH₃)₂NCSNHCH₂CH₂— | " |
| imidazo | CH₃— | CF₃CONHCH₂CH₂— | " |
| benzo | CH₃— | C₆H₅CH₂CONHCH₂CH₂— | " |
| benzo[b]-thieno- | CH₃— | C₆H₅CONHCH₂CH₂— | " |
| 10-methylbenzo[b]thieno- | CH₃— | C₂H₅CONHCH₂CH₂— | 2 |
| 9-methoxybenzo[b]thieno- | H— | CH₃CONHCH₂CH₂— | " |

TABLE VIII-continued

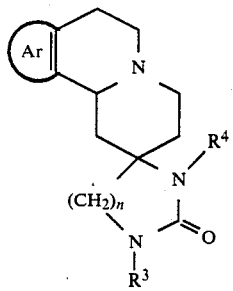

| Ar | R³ | R⁴ (RXOalkylene) | n |
|---|---|---|---|
| 11-fluorobenzo[b]furo- | H— | $CF_3CONHCH_2CH_2$— | " |
| 9-bromobenzo[b]furo- | $C_6H_5$— | $C_6H_5COOCH_2CH_2$— | " |
| 11-methoxybenzo[b]furo- | H— | $CF_3CONHCH_2CH_2$— | " |
| thiazolo- | $CH_3$— | $C_6H_5CONHCH_2CH_2$— | " |
| pyrazolo- | $CH_3$— | $C_6H_5SO_2NHCH_2CH_2$— | " |
| benzo[b]furo- | H— | $CH_3SO_2NHCH_2CH_2CH_2$— | " |
| benzo[b]thieno- | $CH_3$— | $H_2NSO_2NH(CH_2)_5$— | " |
| 9-methoxybenzo- | $CH_3$— | $CH_3SO_2NHCH(CH_3)CH_2$— | " |
| 4,5-dichlorothieno | H— | $CF_3SO_2NHCH_2CH(CH_3)CH_2$— | " |

EXAMPLE IX (2RS,12bSR)-3'-(2-Methanesulfonamidoethyl)-1'-methylspiro-[1,3,4,6,7,12b-hexahydrobenzo[b]furo[2,3-a] quinolizin-2,4'-imidazolidin-2'-one hydrochloride

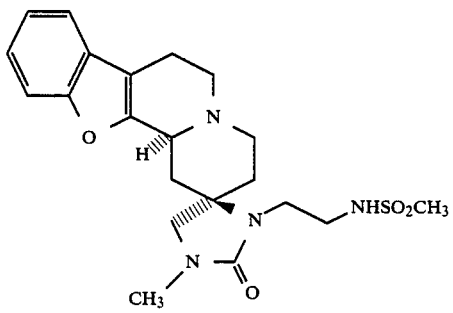

Step A: Preparation of (2RS,12bSR)-3'-(2-(N-benzyloxymethyl)methanesulfonamidoethyl)-spiro-[1,3,4,6,7,12b-hexahydrobenzo[b]furo[2,3-a]quinolizin]-2,4'-imidazolidin-2'-one 0.36 milliliter of a 2.36M solution of n-butyllithium (0.84 mmol) was added to a cold (0° C.) solution of 320 milligrams (0.766 mmol) of (2RS,12bSR) 3'-2-(methanesulfonamidoethyl)-spiro-[1,3,4,6,7,12b-hexahydrobenzo[b]furo[2,3-a]quinolizin]-2,4'-imidazolidin-2-one in 50 milliliters of tetrahydrofuran. After about 10 minutes, 131 milligrams (0.843 mmol) of chloromethyl benzyl ether was added and the reaction stirred at 0° C. for about 1 hour and at ambient temperature for about 18 hours to obtain an N-benzyloxymethyl derivative in the reaction mixture. The reaction mixture was then diluted with water, concentrated and washed with methylene chloride. The methylene chloride solution was dried, filtered and concentrated to obtain a residue which was purified by chromatographing on silica gel employing 10% methanol/ammonia saturated chloroform as eluant to obtain 172 milligrams of (2RS,12bSR)-3'-(2-methanesulfonamidoethyl)-1'-methyl-spiro-[1,3,4,6,7,12b-hexahydrobenzo[b]furo[2,3-a]quinolizin]-2,4'-imidazolidin-2'-one intermediate product.

Step B: Preparation of (2RS,12bSR)-3'-(2-(N-benzyloxymethyl)methanesulfonamidoethyl)-1'-methylspiro-[1,3,4,6,7,12b-hexahydrobenzo[b]furo[2,3-a]quinolizin]-2,4'-imidazolidin-2'-one To a solution of 170 milligrams (0.316 mmol) of (2RS,12bSR)-3'-(2-(N-benzyloxymethyl)methanesulfonamidoethyl)spiro-[1,3,4,6,7,12b-hexahydrobenzo[b]furo-[2,3-a]quinolizin]-2,4'-imidazolidin-2'-one in 50 milliliters of toluene and 50 milliliters of 40 percent sodium hydroxide solution was added first 140 milligrams (0.413 mmol) of tetra N-butylammonium hydrogen sulfonate and then 70 milligrams (0.498 mmol) of methyl iodide. The resulting two phase reaction mixture was stirred vigorously for 20 hours. At the end of this period, the aqueous layer was withdrawn and the organic layer was diluted with 150 milliliters of ethyl acetate and washed with three 100 milliliter portions of water. The organic solution was dried, filtered and concentrated to obtain a residue which was purified by chromatographing on silica gel employing 5 percent methanol/ammonia saturated chloroform as eluant to obtain 105 milligrams of (2RS,12bSR)-3'-(2-(N-benzyloxymethyl)methanesulfonamidoethyl)-1'-methyl-spiro-[1,3,4,6,7,12b-hexahydrobenzo[b]furo[2,3-a]quinolizin]-2,4'imidazolidin-2'-one intermediate product.

Step C: Preparation of (2RS,12bSR)-3'-(2-methanesulfonamidoethyl)-1'-methylspiro-[1,3,4,6,7,12b-hexahydrobenzo[b]-furo[2,3-a]quinolizin]-2,4'-imidazolidin-2'-one monohydrochloride 3 milliliters of 6N hydrochloric acid solution was added to a solution of 105 milligrams (0.195 mmol) of (2RS,12bSR)-1'-methyl-3'-(2-(N-benzyloxymethyl)methanesulfonamidoethyl)-spiro-[1,3,4,6,7,12b-hexahydrobenzo[b]furo[2,3-a]quinolizin]-2,4'-imidazolidin-2-one in 4 milliliters of dimethoxyethane and caused to react at room temperature. After about three hours, the reaction mixture was made basic and the product extracted into ethyl acetate. The ethyl acetate solution was dried, then filtered and concentrated to obtain a residue which was purified by chromatographing on silica gel employing 5 percent methanol/ammonia saturated chloroform as eluant to obtain 40 milligrams of (2RS,12bSR)-3'-(2-methanesulfonamidoethyl)-1'-methylspiro-[1,3,4,6,7,12b-hexahydrobenzo[b]-furo[2,3-a]quinolizin]-2,4'-imindazolidin-2'-one hydrochloride, m.p. 240°-243° C. (dec.).

EXAMPLE X (2RS,11bSR)-9-Methoxy-3'-(2methanesulfonamidoethyl)-spiro-(1,3,4,6,7,11b-hexahydrobenzo[a]quinolizin)-2,4'-imidazolidin-2'-one

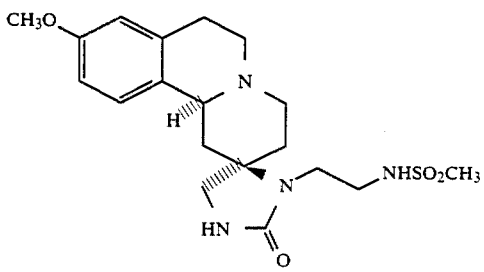

Step A: Preparation of (2RS,11bSR)-9-methoxy-2-((2-methanesulfonamidoylethyl)amino)-2-aminomethyl-1,3,4,6,7,11b-hexahydrobenzo[a]quinolizine 2.44 grams (17.68 mmol) of N-methanesulfonylethylenediamine, 30 millilters of methanol, 3.27 grams (14.14 millimoles) of (+/−) 9-methoxy-1,3,4,6,7,11b-hexahyrobenzo[a]quinolizine-2-one and 2.88 grams (17.68 mmol) of diethyl cyanophosphonate were stirred together at room temperature for 3 hours. The mixture was concentrated in vacuo to a syrup which was dissolved in 300 milliliters of chloroform and washed with one 200 milliliter portion of water. The chloroform solution was then dried over sodium sulfate, filtered and concentrated in vacuo to obtain a cyanoamine intermediate as residue. The latter was dissolved in 50 milliliters of tetrahydrofuran and added dropwise to a cooled to 0° C., well-stirred solution of 2.14 grams (56.56 mmol) of lithium aluminum hydride in 250 milliliters of ether over one-half hour period. The mixture was stirred for an additional hour at 0° C. and then quenched by the n,n,3n method. (A method described on page 584 of Fieser & Fieser, "Reagents for Organic Synthesis", John Wiley & Sons, Inc. N.Y. 1967, for quenching a lithium aluminum hydride reduction mixture). The suspension was filtered and the salts extracted with ammonia saturated chloroform. The organic portions were combined, concentrated in vacuo and chromatographed on 150 grams of silica gel using 5 percent methanol in ammonia saturated chloroform as eluant to obtain 2.39 grams (44 percent yield) of (2RS,11bSR)-9-methoxy-2-((2-methanesulfonamidoylethyl)amino)-2-aminomethyl-1,3,4,6,7,11b-hexahydrobenzo[a]quinolizine as a 9:1 mixture of c-2 diastereomers.

Step B: Preparation of (2RS,11bSR)-9-methoxy-3'-(2-methanesulfonamidoylethyl)-spiro-(1,3,4,6,7,11b-hexahydrobenzo[a]quinolizin)-2,4'imidazolin-2'-one 2.39 grams (6.25 mmol) of (2RS,11bSR)-9-methoxy-2-((2-methanesulfonamidoylethyl)amino)-2-aminometh-yl-1,3,4,6,7,11b-hexahydrobenzo[a]quinolizine, 75 milliliters of methylene chloride and 1.27 grams (7.81 mmol) was stirred under argon atmosphere at room temperature for 24 hours, thereafter diluted with 200 milliliters of methylene chloride and washed with two 100 milliliter portions of water and 100 milliliters of brine. The solution was dried (MgSO₄) and solvent vaporized from the dried solution in vacuo to obtain a tan solid which was purified by chromatographing on silica gel using 4 percent methanol in ammonia saturated chloroform as eluant to obtain 1.08 grams of (2RS,11bSR)-9-methoxy-3'-(2-methanesulfonamidoethyl)-spiro-(1,3,4,6,7,11b)hexahydrobenzo[a]quinolizin-2,4'-imidazolidin-2'-one as the base.

The base mixed with methanolic hydrogen chloride to obtain the hydrochloride salt which when recrystallized from methanol/ethyl acetate had a melting point of 284°-286° C. (dec.).

EXAMPLE XI (2RS,11bSR)-9-Hydroxy-8-carboxy-3'-(2-methanesulfonamidoethyl)-spiro-(1,3,4,6,7,11b-hexahydrobenzo[a]quinolizin)-2,4'-imidazolidin-2'-one

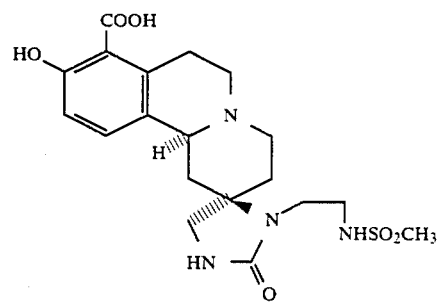

Step A: Preparation of (2RS,11bSR)-9-hydroxy-3'-(2-methanesulfonamidoethyl)-spiro-(1,3,4,6,7,11b-hexahydrobenzo[a]quinolizin)-2,4'-imidazolidin-2'-one A solution of 0.79 gram (1.93 mmol) of (2RS,11bSR)-9-methoxy-3'-(2-methanesulfonamidoethyl)-spiro-(1,3,4,6,7,11b-hexahydrobenzo[a]quinolizine)-2,4'-imidazolidin-2'-one prepared as described in Example X in 50 millilters of methylene chloride was cooled to 0° C. in an atomsphere of argon and 5.80 millilters of a 1.0M solution in methylene chloride of boron tribromide (1.45 g, 5.8 mmol) was added dropwise thereto. The mixture was warmed to room temperature and stirred overnight. At the end of this time the reaction was quenched with saturated sodium bicarbonate solution. The layers were separated and the organic phase dried and the dried solution concentrated in vacuo. The crude product was chromatographed on 75 g of silica gel using 1:9 methanol-chloroform as eluant. There was obtained 226 mg of (2RS,11bSR)-9-hydroxy-3'-(2-methanesulfonamidoethyl)-spiro-(1,3,4,6,7,11b-hexahydrobenzo[a]quinolizin)-2,4'-imidazolidin-2'-one as a white solid. The HCl salt had melting point >270° C.

Step B: Preparation of (2RS,11bSR)-9-diethylcarbamoyloxy-3'-(2-methanesulfonamidoethyl)-spiro-(1,3,4,6,7,11b-hexahydrobenzo[a]quinolizin)-2,4'-imidazolidin-2'-one 1.0 millimole of (2RS,11bSR)-9-hydroxy-3'-(2-methanesulfonamidoethyl)-spiro-(1,3,4,6,7,11b-hexahydrobenzo[a]quinolizin)-2,4'-imidazolidin-2'-one, 50 milliliters of methylene chloride, 1.5 millimole of N,N-diisopropylethylamine and 1.1 millimole of diethylcarbamoyl chloride are stirred together at room temperature for 24 hours, and the organic mixture washed with water, and brine, dried and concentrated in vacuo to obtain a crude intermediate product. The crude product is chromatographed on silica gel using methanol-ammonia-chloroform as eluant to obtain purified (2RS,11bSR)-9-diethylcarbamoyloxy-3'-(2-methanesulfonamidoethyl)-spiro-(1,3,4,6,7,11b-hexahydrobenzo[a]quinolizin)-2,4'-imidazolidin-2'-one intermediate product.

Step C: Preparation of (2RS,11bSR)-9-hydroxy-8-diethylaminocarbonyl-3'-(2-methanesulfonamidoethyl)-spiro-(1,3,4,6,7,11b-hexahydrobenzo[a]quinolizin)-2,4'-imidazolidin-2'-one 1.0 millimole of (2RS,11bSR)-9-diethylcarbamoyloxy-3'-(2-methanesulfonamidoethyl)-spiro-(1,3,4,6,7,11b-hexahydrobenzo[a]quinolizin)-2,4'-imidazolidin-2'-one, 25 milliliters dry THF, 1.1 millimole of tetramethyl ethylenediamine and the resulting solution cooled to −78° C. To this cold solution is added dropwise over a period of 30 minutes, 3.3 milliliters of a 1.0M solution of secondary butyl lithium in pentane. The mixture is then allowed to warm to room temperature and stirred for 12 hours. Aqueous sodium bicarbonate is then added to quench the reaction and the layers then separated. The aqueous phase is extracted with chloroform. The organic solutions are combined, dried and the solvent vaporized in vacuo to obtain (2RS,11bSR)-9-hydroxy-8-diethylaminocarbonyl-3'-(2-methanesulfonamidoethyl)-spiro-(1,3,4,6,7,11b-hexahydrobenzo[a]quinolizin)-2,4'-imdazolindin-2'-one

Step D: Preparation of (2RS,11bSR)-9-hydroxy-8-carboxy-3'-(2-methanesulfonamidoethyl)-spiro-(1,3,4,6,7,11b-hexahydrobenzo[a]quinolizin)-,4'-imidazolidin-2'-one 1.0 millimole of (2RS,11bSR)-9-hydroxy-8-diethylaminocarbonyl-3'-(2-methanesulfonamidoethyl)-spiro-(1,3,4,6,7,11b-hexahydrobenzo[a]quinolizin)-2,4'-imidazolidin-2'-one, 50 milliliters of methanol and 10.0 millimoles of lithium hydroxide are heated together with stirring at reflux temperature in an argon atmosphere for 24 hours. The solution is cooled to room temperature and methanol removed in vacuo. The residue is dissolved in 20 milliliters of water and the pH is adjusted to 7.5 by careful addition of 1.0 N HCl. The aqueous mixture is extracted repeatedly with 10 milliliter portions of chloroform. The combined chloroform extracts are dried and concentrated in vacuo. The residue is chromatographed on silica gel using methanol-chloroform as eluant to obtain (2RS,11bSR)-9-hydroxy-8-carboxy-3'-(2-methanesulfonamidoethyl)-spiro-(1,3,4,6,7,11b-hexahydrobenzo[a]quinolizin)-2,4'-imidazolidin-2'-one.

EXAMPLE XII (2R,11bS)-9-methoxy-1,3,4,5',6,6',7,11b-octahydro-3'-(2-methanesulfonamidoethyl)-spirobenzo[a]quinolizin-2,4'-(1'H-pyrimidin-2'-(3'H)-one)

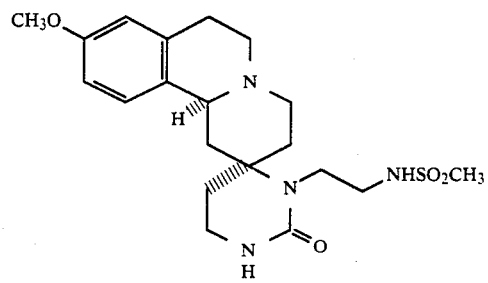

Step A: Resolution of 9-methoxy-1,3,4,6,11b-hexahydrobenzo[a]quinolizine-2-one A solution of 55 grams (238 mmol) of racemic 9-methoxy-1,3,4,6,7,11b-hexahydrobenzo[a]quinolizin-2-one in 3 liters of ethyl acetate and solution of 96.2 grams (238 mmol) of (−) di-para-toluoyl-L-tartaric acid monohydrate in 3 liters of ethyl acetate were mixed together at room temperature and stirred overnight whereupon finely precipitated crystals of tartrate salt formed. These were collected on a frit and subsequently converted into the free base with aqueous sodium carbonate solution and chloroform. There was obtained 28.7 grams of free base ketone having a specific rotation=−63.6°, c=0.0069 g/ml. The crystallization process was repeated an additional three times to obtain optically pure ketone having a specific rotation of −120°, c=0.007 g/ml in chloroform.

Step B: Preparation of E,Z (11bS)-9-methoxy-2-cyanomethylidine-1,3,4,6,7,11b-hexahydrobenzo[a]quinolizine 20.8 grams (129.71 mmol) of a 25% W/W suspension of potassium hydride in mineral oil under argon was washed twice with hexane to remove the mineral oil. The oil free potassium hydride was suspended in 200 ml of dry THF and the suspension was cooled at 0° C. To this mixture, while stirring was added dropwise over 30 minutes a solution of 22.98 grams (129.7 mmol) diethyl cyanomethylphosphonate in 100 milliliters of THF. When the addition was complete, the mixture was stirred an addition 15 minutes; then a solution of 10.0 grams (43.24 mmol) of optically pure (−)9-methoxy-1,3,4,6,7,11b-hexahydrobenzo[a]quinolizin-2-one in 200 milliliters of THF was added dropwise over 45 minutes. The cooling bath was allowed to expire and the mixture was stirred at room temperature overnight. The reaction mixture was diluted with water and ethyl acetate. The layers were separated and the organic phase was washed with water (3 times) and with brine. The organic phase was dried over Na2SO4, then filtered to remove Na2SO4, and the solvent removed in vacuo to obtain a brown oil. This material was chromatographed on 300 grams of silical gel using ethyl acetate as eluant. There was obtained 10.77 grams of pure E,Z (11bS)-9-methoxy-2-cyanomethylidine-1,3,4,6,11b-hexahydrobenzo[a]quinolizine.

Step C: Preparation of (2R,11bS) 2-(2-aminoethylamino)-2-cyanomethyl-9-methoxybenzo[a]quinolizine 10.77 grams (42.35 mmol) of E,Z (11bS)-9-methoxy-2-cyanomethylidine-1,3,4,6,7,11b-hexahydrobenzo[a]quinolizine, 30 milliliters of absolute ethanol and 60 milliliters (897.5 mmol) of ethylenediamine were stirred together under an atomosphere of argon at 50° C. for 21 days. The reaction mixture was cooled to room temperature and concentrated in vacuo. The residue was chromatographed on 400 grams of silica gel using 1:9 methanol-chloroform saturated with ammonia as eluant to obtain 9.28 grams of (2R,11bS) 2-(2-aminoethylamino)-2-cyanomethyl-9-methoxy-1,3,4,6,7,11b-hexahydrobenzo[a]quinolizine as a viscous oil.

Step D: Preparation of (2R,11bS) 2-(2-methanesulfonamidoethylamino)-2-cyanomethyl-9-methoxy-1,3,4,6,7,11b-hexahydrobenzo-[a]quinolizine 6.46 grams (20.55 mmol) of (2R,11bS) 2-(2-aminoethylamino)-2-cyanomethyl-9-methoxy-1,3,4,6,7,11b-hexahydrobenzo[a]quinolizine, 100 millliters of chloroform, 100 milliliters of water, 8.50 grams (61.64 mmol) of potassium carbonate and 7.15 grams (41.09 mmol) of methanesulfonic anhydride were stirred vigorously for one hour under and atmosphere of argon at room temperature. The layers were separated and the organic phase was washed with water and brine. The mixture was dried, filtered, and then subjected to reduced pressure to obtain 6.06 grams of pure (2R,11bS) 2-(2-methanesulfonamidoethylamino)-2-cyanomethyl-9-methoxy-1,3,4,6,7,11b-hexahydrobenzo[a]quinolizine as a foam.

Step E: Preparation of (2R,11bS) 2(2-methanesulfonamidoethylamino)-2(2-aminoethyl)-9-methoxy-1,3,4,6,7,11,b-hexahydrobenzo[a]quinolizine A solution of 2.93 grams (77.20 mmol) of lithium alluminum hydride in 350 milliliters of ethyl ether was cooled to 0° C. and a solution of 6.06 grams (15.44 mmol) of (2R,11bS) 2-(2-methanesulfonamidoethylamino)-2-cyanomethyl-9-methoxy-1,3,4,6,7,11b-hexahydrobenzo[a]quinolizine in 100 milliliters of THF was added dropwise over 30 minutes. The cooling bath was allowed to expire and the mixture was stirred overnight at room temperature. The reaction mixture was recooled to 0° C. and then quenched by the addition of 200 milliliters of saturated aqueous sodium potassium tartrate solution. The resulting mixture was stirred at room temperature for 4 hours. The layers were separated and the aqueous phase was extracted with chloroform. The organic solutions were combined, dried over Na2SO4, and then filtered. Thereafter, the filtrate was subjected to reduced pressure to obtain 5.51 grams of (2R,11bS) 2-(2-methanesulfonamidoethylamino)-2-cyanomethyl-9-methoxy-1,3,4,6,7,11b-hexahydrobenzo[a]-quinolizine.

Step F: Preparation of (2R,11bS) 9-methoxy-1,3,4,5',6,6',7,11b-octahydro-3'(2-methanesulfonamodiethyl)-spiro-benzo[a]-quinolizin-2,4,'-(1'H-pyrimidin-2'-(3'H)-one 4.50 grams (11.35 mmol) of (2R,11bS) 2-(2-methanesulfonamidoethylamino)-2-(2-aminoethyl)-9-methoxy-1,3,4,6,7,11b-hexahydrobenzo[a]quinolizine and 600 milliliters of methylene chloride containing 6.02 milliliters (25.01 mmol) of dry pyridine was cooled to 0° C. and 6.02 milliliters (11.91 mmol) of a 1.98M solution of phosgene in toluene was added dropwise over two hours. The mixture was stirred overnight at room temperature, washed with saturated aqueous NaHCO3 and brine, dried, filtered and concentraed in vacuo. The residue was chromatographed on 80 grams of silica gel using 1:4 methanolethyl acetate as eluant to obtain 1 gram of (2R,11bS) 9-methoxy-1,3,4,5',6,6',7,11b-octahydro-3'-(2-methanesulfonamidoethyl)-spiro-benzo[a]quinolizine-2,4'-(1'H-pyrimidin-2'-(3'H)-one as the free base. The HCl salt was prepared from 2-propanol and concentrated HCl. The HCl salt has a melting point 170°-174° C. with decomposition. The specific rotation for the HCl salt was −32.2°, c=0.012 g/ml, methanol.

EXAMPLE XIII (2R,11bS) 9-methoxy-1,3,4,5',6,6',7,11b-octahydro-3'-(2-sulfamidoethyl)-spiro-benzo[a]quinolizin-2,4'(1'H-pyrimidin-2'-(3'H)-one

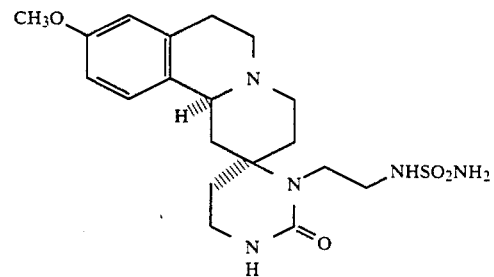

Step A: Preparation of (2R,11bS) 2-(2-tert-butylsulfamidoethylamino)-2cyanomethyl-9-methoxybenzo[a]quinolizine 4.57 grams (14.53 mmol) of (2R,11bS) 2-(2-aminoethylamino)-2-cyanomethyl-9-methoxy-1,3,4,6,7,11b-hexahydrobenzo[a]-quinolizine (prepared as described in Example XII, Step C), 130 milliliters of dry methylene chloride and 2.78 milliliters (15.99 mmol) of diisopropylethylamine were cooled at 0° C. and a solution of 2.62 grams (15.26 mmol) of tert-butylsulfamyl chloride in 20 milliliters of methylene chloride was added dropwise over 15 minutes. This mixture was stirred at room temperature overnight. The reaction mixuture was diluted with chloroform and was washed with aqueous NaHCO3 solution and brine. The solution was dried, filtered and the solvent removed in vacuo to obtain 6.70 gram of a foam. This material was chromatographed on 175 gram of silica gel using 2% methanol in ammonia saturated chloroform as eluant to obtain 4.57 gram of (2R,11bS) 2-(2-tert-butylsulfamidoethylamino)-2-cyanomethyl-9-methoxy-1,3,4,6,7,11b-hexahydrobenzo[a]quinolizine as a coloress oil.

Step B: Preparation of (2R,11bS) 2-(2tert-butylsulfamidoethylamino-2-(2-aminoethyl)-9-methoxy-1,3,4,6,7,11b-hexahydrobenzo[a]quinolizine 200 milliliters of dry ethyl ether and 1.63 grams (42.83 mmol) of lithium aluminum hydride under an atmosphere of nitrogen was cooled to 0° C. and a soltion of 3.21 grams (7.14 mmol) of (2R,11bS) 2-(2-tert-butylsulfamidoethylamino)-2-cyanomethyl-9-methoxy-1,3,4,6,7,11b-hexahydrobenzo[a]quinolizine in 40 milliliters of THF was added dropwise over 30 minutes. The cooling bath was allowed to expire and the mixture was stirred overnight at room temperature. The mixture was recooled to 0° C. and the reaction was quenched by addition of 100 milliliters of saturated aqueous sodium potassium tartrate solution. The layers were separated and the aqueous layer was extracted with chloroform. The organic solutions were combined, dred over Na$_2$SO$_4$, filtered and concentrated in vacuo to obtain 3.15 grams of (2R,11bS) 2-(2-tert-butylsulfamidoethylamino)-2(2-aminoethyl)-9-methoxy-1,3,4,6,7,11b-hexahydrobenzo[a]quinolizine.

Step C: (2R,11bS) 9-methoxy-1,3,4,5',6,6',7,11b-octahydro-3'-(2-(N'-tert-butylsulfamidoethyl-spiro-benzo[a]quinolizin-2,4'-(1'H-pyrimidin-2'-(3'H)-one)

3.15 grams (6.94 mmol) of (2R,11bS) 2-(2-tert-butylsulfamidoethylamino)-2-(2-aminoethyl)-9-methoxy-1,3,4,6,7,11b-hexahyrobenzo[a]quinolizine and 50 milliliters of dry toluene were heated to 50° C. and 1.41 grams (8.68 mmol) of 1,1'-carbonyldiimidazole was added portionwise with vigorous stirring. This mixture was maintained at 50° C. under nitrogen for three hours. The cooled reaction mixture was diluted with ethyl acetate and was washed with water and brine, the solution dried over Na$_2$SO$_4$, then the latter filtered and the filtrate subjected to reduced pressure to obtain 3.19 grams of 9-methoxy-1,3,4,5',6,6',7,11b-octahydro-3'-(2-(N'-tert-butylsulfamidoethyl-spiro-benzo[a]quinolizin-2,4'-(1'H-pyrimidin-2'-(3'H)-one.

Step D: (2R,11bS)-9-methoxy-1,3,4,5',6,6',7,11b-octahydro-3'-(2-sulfamidoethyl)-spiro-benzo[a]quinolizin-2,4'-(1'H-pyrimidin-2'-(3'H)-one 2.99 grams (6.23 mmol) of (2R,11bS)-9-methoxy-1,3,4,5',6,6',7,11b-octahydro-3'-(2-(N'-tert-butylsulfamidoethyl)-spiro-benzo[a]quinolizin-2,4'-(1'H-pyrimidin-2'-(3'H)-one), and 25 milliliter of trifluoroacetic acid were stirred together at room temperature for two hours. The mixture was diluted with 200 milliliters of chloroform and was made basic with aqueous sodium carbonate solution. The layers were separated and the organic layer was washed with water and brine. Drying (Na$_2$CO$_4$), filtration and removal of the solvent in vacuo followed by chromatography on 85 grams of silica gel using 1:9 methanolchloroform as eluant produced 1.76 grams of (2R,11bS) 9-methoxy-1,3,4,5',6,6',7,11b-octahydro-3'-(2-sulfamidoethyl)-spiro-benzo[a]quinolizin-2,4'-(1'H-pyrimidin-2'-(3'H)-one) as the free base. The HCl salt was prepared from methanol and concentrated HCl and had a melting point of 239°-240° C. The specific rotation of the HCl salt was −30.24°, c=0.0033 g/ml, MeOH.

EXAMPLE XIV (2R,13bSR) 1,3,4,6,7,13b-hexahydro-3'-(2-methanesulfonamidoethyl)-spiro-(naphthaleno[2,1-a]quinolizin)-2,4'-(imidazolidin-2'-one)

Step A: Preparation of 3,4-dihydrobenzo[f]isoquinoline

A solution of 18.15 grams (91 mmol) of 2-formamidoylethyl-1naphthalene in 120 milliliters of chloroform was added dropwise over one hour to a well stirred refluxing mixture of 34 grams of celite, 68 grams (479 mmol) of phosphorous pentoxide and 360 milliliters of dry benzene.

The mixture was maintained at reflux for 24 hours, cooled to room temperature and poured into 1 liter of water. This mixture was stirred for 4 hours and was then filtered through a pad of celite. The filtrate was washed with 500 milliliters of chloroform and the aqueous phase was made basic with concentrated ammonium hydroxide. This solution was extracted with three 250 milliliter portions of chloroform and the combined chloroform extracts were dried over sodium sulfate. The dried solution was filtered, the filtrate subjected to reduced pressure and the residue chromatographed on 100 grams of silica gel using ethyl acetate as eluant to obtain 5.6 grams of 3,4-dihydrobenzo[f]isoquinoline. The HCl salt was prepared from ethanolic hydrogen chloride and had a m.p. of 190°-191° C.

Step B: Preparation of (13bSR) 1,3,4,6,7,13b-hexahydronaphthaleno[2,1-a]quinolizin-2-one 4.00 grams (18.37 mmol) of 3,4-dihydrobenzo[f]isoquinoline hydrochloride and 55 ml (660 mmol) of methyl vinyl ketone was stirred and heated at reflux temperature for 4 hours, then cooled to room temperature and filtered. The filter cake was washed with ethyl ether and then suspended in chloroform. The solution was made basic with aqueous sodium carbonate and the layers were separated. The chloroform solution was washed with brine, dried (Na$_2$SO$_4$), filtered and concentrated in vacuo. The residue was chromatographed on 90 grams of silica gel using 1:1 ethyl acetate-hexanes as eluant. There was obtained 2.87 grams of (13bSR) 1,3,4,6,7,13b-hexahydronaphthaleno[2,1-a]quinolizin-2-one as a white crystalline solid.

Step C: Preparation of (2RS,13bSR) 2-(2-methanesulfonamidoethyl)-2-cyano-1,3,4,6,7,13b-hexahydronaphthaleno[2,1-a]quinolizine To 1.91 grams (7.60 mmol) of (13bSR) 1,3,4,6,7,13b-hexahydronaphthaleno[2,1-a]quinolizin-2-one was added 80 milliliters of tetrahydrofuran, a solution of 1.31 grams (9.50 mmol) of methanesulfonamidoethylenediamine in 30 milliliters of methanol and 1.44 milliliters (9.50 mmol) of diethyl cyanophosphonate. This mixture was stirred for 4 hours at room temperature and was concentrated in vacuo. The residue was partitioned between water and chloroform. The chloroform layer was dried (Na$_2$SO$_4$), filtered and concentrated in vacuo to give 3.0 grams of (2RS,13bSR) 2-(2-methanesulfonamidoethylamino)-2-cyano-1,3,4,6,7,13b-hexahydronaphthaleno[2,1-a]quinolizin Step D: Preparation of (2RS,13bSR) 2-(2-methanesulfonamidoethylamino)-2-aminomethyl-1,3,4,6,7,13b-hexahydronaphthaleno[2,1-a]quinolizine To a cooled to 0° C. solution of 150 milliliters of ethyl ether and 1.15 grams (30.4 mmol) of lithium aluminum hydride was added a solution of 3.2 grams (7.60 mmol) of (2RS,13bSR) 2-(2-methanesulfonamidoethylamino)-2-cyano-1,3,4,6,7,13b-hexahydronaphthaleno[2,1-a]quinolizine in 30 milliliters of tetrahydrofuran was added dropwise over 30 minutes. The cooling bath was allowed to expire and the mixture was stirred at room temperature overnight. The reaction mixture was recooled to 0° C. and the reaction was quenched by slow addition of saturated aqueous sodium potassium tartrate solution. This mixture was stirred at room temperature for 4 hours. The layers were separated and the aqueous phase was extracted with chloroform. The organic phases were combined, dried (Na$_2$SO$_4$), filtered, concentrated and chromatographed on 65 grams of silica gel using 1:4 methanol-ammonia saturated chloroform as eluant. The solvent was vaporized from the eluate to obtain 0.64 gram of (2RS,13bSR) 2-(2-methanesulfonamidoethylamino)-2-aminomethyl-1,3,4,6,7,13b-hexahydronaphthaleno[2,1-a]quinolizine as an oil.

Step E: (2RS,13bSR) 1,3,4,6,7,13b-hexahydro-3'-(2-methanesulfonamidoethyl)-spiro-(naphthaleno[2,1-a]quinolizin)-2,4'-(imidazolidin-2'-one)

640 milligrams (1.59 mmol) of (2RS,13bSR) 2-(2-methanesulfonamidoethylamino)-2-aminomethyl-1,3,4,6,7,13b-hexahydronaphthaleno[2,1-a]quinolizine, 25 milliliters of toluene and 384 milligrams (2.38 mmol) of 1,1'-carbonyldiimidazole were stirred and heated at 50° C. for 24 hours under argon. The reaction mixture was diluted with 300 milliliters of chloroform and was washed with water and brine. The washed solution washed, dried (Na$_2$SO$_4$), filtered, concentrated in vacuo and chromatographed on 50 grams of silica gel using 15:85 methanol-ethyl acetate as eluant to obtain from the eluate 600 milligrams of (2RS,13bSR) 1,3,4,6,7,13b-hexahydro-3'-(2-methanesulfonamidoethyl)-spiro-(naphthaleno[2,1-a]quinolizin)-2,4'-(imidazolidin-2'-one) free base. The HCl salt was prepared from ethanolic hydrogen chloride and was recrystallized from methanol-ethyl acetate, m.p., 227°–229° C. with decomposition.

EXAMPLE XV (2R,12bS) 1,3,4,5',6,6',7,12b-octahydro-3'-(2-methanesulfonamidoethyl)-spiro(2H-benzo[b]furo[2,3-a]quinolizin)-2,4'-(1'H-pyrimidin-2'-(3'H)-one)

Step A: Preparation of E,Z (12bS)-2-cyanomethylidene-1,3,4,5,7,12b-hexahydro-2H-benzo[b]furo [2,3-a]quinolizine (124.33 mmol) of a 25% w/w suspension of potassium hydride in mineral oil was washed under argon atmosphere with two hexane washings and the oil free potassium hydride then was suspended in 125 milliliters of dry tetrahydrofuran, stirred and cooled to 0° C. A solution of 22.02 grams (124.33 mmol) of diethyl cyanomethylphosphonate in 60 milliliters of THF was added dropwise over 30 minutes. The mixture was stirred an additional 30 minutes and a solution of 10.00 grams (41.44 mmol) of (12bS) 1,3,4,6,7,12b-hexahydro-2H-benzo[b]furo[2,3-a]quinolizin-2-one in 65 milliliters of THF was added dropwise over 30 minutes. The cooling bath was allowed to expire and the mixture was stirred overnight at room temperature. 200 milliliters of water was added to quench the reaction and the mixture was diluted with ethyl acetate. The layers were separated and the organic phase was washed with water and brine. The solution was dried (MgSO$_4$), filtered and the solvent removed in vacuo to obtain 10.95 grams of E,Z (12bS)-2-cyanomethylidene-1,3,4,6,7,12b-hexahydro-2H-benzo[b]furo[2,3-a]quinolizine as an oil.

Step B: Preparation of (2R,12bS) 2-cyanomethyl-2-(2-aminoethylamino)-1,3,4,6,7,12b-hexahydro-2H-benzo[b]furo[2,3-a]quinolizine 10.95 grams (41.55 mmol) of E,Z (12bS)-2-cyanomethylidene-1,3,4,6,7,12b-hexahydro-2H-benzo[b]furo[2,3-a]quinolizine, 60 milliliters of absolute ethanol and 60 milliliters (898 mmol) of ethylenediamine were stirred and heated under argon atmosphere at 40° C. for six days. The reaction mixture was concentrated in vacuo and the residue was chromatographed on 400 grams of silica gel using 5% methanol in ammonia saturated chloroform as eluant. The eluate was concentrated in vacuo to obtain 6.30 grams of (2R,12bS)-2-cyanomethyl-2-(2-aminoethylamino)-1,3,4,6,7,12b-hexahydro-2H-benzo[b]furo[2,3-a]quinolizine as an oil.

Step C: Preparation of (2R,12bS)-2-cyanomethyl-2-(2-methanesulfonamidoethylamino)-1,3,4,6,7,12b-hexahydro-2H-benzo[b]furo[2,3-a]quinolizine 6.30 grams (19.42 mmol) of (2R,12bS)-2-cyanomethyl-2-(2aminoethylamino)-1,3,4,6,7,12b-hexahydro-2H-benzo[b]furo[2,3-a]quinolizine, 150 milliliters of chloroform, 150 milliliters of water, 5.36 grams (38.84 mmol) of finely powdered potassium carbonate, and 5.07 grams (29.13 mmol) of methanesulfonic anhydride were stirred vigorously at room temperature for one hour. The mixture was diluted with chloroform and the layers were separated. The organic phase was washed with water (2X 500 ml) and brine. The washed solution was dried, filtered and the solvent removed in vacuo to obtain 7.80 grams of (2R,12bS)-2-cyanomethyl-2-(2-methanesulfonamidoethylamino)-1,3,4,6,7,12b-hexahydro-2H-benzo[b]furo[2,3-a]quinolizine as an oil.

Step D: Preparation of (2R,12bS) 2-(2-aminoethyl)-2-(2-methanesulfonamidoethylamino)-1,3,4,6,7,12b-hexahydro-2H-benzo[b]furo[2,3-a]quinolizine 500 milliliters of ethyl ether and 1.47 grams (38.84 mmol) of lithium aluminum hydride were stirred and cooled to 0° C., and a solution of 7.80 grams (19.4 mmol) of (2R,12bS) 2-cyanomethyl-2-(2-methanesulfonamidoethylamino)-1,3,4,6,7,12b-hexahydro-2H-benzo[b]furo[2,3-a]quinolizine in 100 ml of dry tetrahydrofuran was added dropwise over one hour. An additional 1 gram of lithium aluminum hydride was added after one hour and the mixture was stirred overnight at room temperature. The reaction mixture was recooled to 0° C. and the reaction was quenched by addition of 200 milliliters of saturated aqueous sodium potassium tartrate solution. The resulting mixture was stirred at room temperature for 4 hours. The layers were separated and the aqueous phase was extracted with chloroform. The organic phases were combined, dried (Na$_2$SO$_4$), filtered and concentrated in vacuo to obtain 7.9 grams of (2R,12bS)-2-(2-aminoethyl)-2-(2-methanesulfonamidoethylamino)-1,3,4,6,7,12b-hexahydro-2H-benzo[b]furo[2,3-a]quinolizine as a foam.

Step E: Preparation of (2R,12bS) 1,3,4,5',6,6',7,12b-octahydro-3'-(2-methanesulfonamidoethyl)-spiro(2H-benzo[b]furo]2,3-a]quinolizin)-2,4'-(1'H-pyrimidin-2'-(3'H)-one)

7.90 grams (19.42 mmol) of (2R,12bS) 2-(2-aminoethyl)-2-(2-methanesulfonamidoethylamino)-1,3,4,6,7,12b-hexahydro-2H-benzo[b]furo[2,3-a]quinolizine, 100 milliliters of dry methylene chloride, and 6.06 milliliters (75.00 mmol) of pyridine were mixed together and cooled to 0° C. and 20.3 ml (22.33 mmol) of a 1.10 M solution of phosgene in benzene was added dropwise over 15 minutes. This mixture was stirred for an additional 30 minutes and was then partitioned between aqueous sodium bicarbonate and chloroform. The organic phase was washed with brine, dried (Na₂SO₄), filtered, the solvent removed in vacuo and chromatographed on 200 grams of silica gel using 3% methanol in ammonia saturated chloroform as eluant to obtain 0.95 gram of (2R,12bS) 1,3,4,5',6,6', 7,12b-octahydro-3'-(2-methanesulfonamidoethyl)-spiro-(2H-benzo[b]furo[2,3-a]quinolizin)-2,4'-(1'H-pyrimidin-2'-(3'H)-one) free base. The HCl salt was prepared from 2-propanol and methanolic HCl, m.p. 160°–167° C. with decomposition.

EXAMPLE XVI (2SR,12bSR)-1,3,4,5',6,6',7,12b-octahydro-1'-(2-methanesulfonamidoethyl)-3'-methyl-spiro(2H-benzo[b]furo[2,3-a]quinolizin)-2,4'-(1-'H-pyrimidin-2'-(3'H)-one)

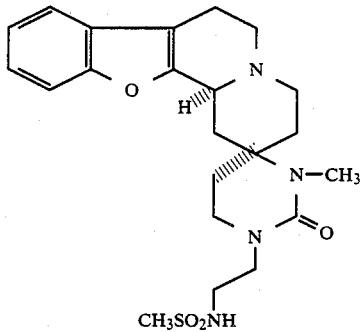

Step A: Preparation of (2RS,12bSR) N-(2-aminoethyl)-(2-methylamino-1,3,4,6,7,12b-hexahydro-2H-benzo[b]furo[2,3-a]quinolizin-2-yl)acetamide 8.0 grams (24.36 mmol) of (2RS,12bSR) methyl (2methylamino-1,3,4,6,7,12b-hexahydro-2H-benzo[b]furo[2,3-a]quinolizin-2-yl) acetate, 400 milliliters of absolute ethanol, 24.4 milliliters (365 mmol) of ethylenediamine, and 1.44 milliliters (24.36 mmol) of glacial acetic acid were stirred under argon and heated at reflux for 8 hours, then overnight at room temperature. The mixture was concentrated in vacuo and the residue was taken up in chloroform and washed with sodium bicarbonate solution and brine. The solution was dried (Na₂SO₄), filtered, concentrated in vacuo and chromatographed on 300 grams of silica gel using 1% methanol in ammonia saturated chloroform to obtain 2.70 grams of (2RS,12bSR) N-(2-aminoethyl)-(2-methylamino-1,3,4,6,7,12b-hexahydro-2H-benzo[b]furo[2,3-a]quinolizin-2-yl)acetamide.

Step B: Preparation of (2RS,12bSR) N-(2-methanesulfonamidoethyl)-(2-methylamino-1,3,4,6,7,12b-hexahydro-2H-benzo[b]furo[2,3-a]quinolizin-2-yl)acetamide 2.30 grams (6.45 mmol) of (2RS,12bSR)-N-(2-aminoethyl)-(2-methylamino-1,3,4,6,7,12b-hexahydro-2H-benzo[b]furo[2,3-a]quinolizin-2-yl)acetamide, 100 milliliters of chloroform, 50 milliliters of water 0.89 gram (6.45 mmol) of finely powdered potassium carbonate, and 1.24 grams (7.10 mmol) of methanesulfonic anhydride were stirred vigorously for two hours at room temperature. The layers were separated and the organic phase was dried (Na₂SO₄), filtered, concentrated and chromatographed on 150 grams of silica gel using 2% methanol in ammonia saturated chloroform as eluant. There was obtained from the eluate 1.33 grams of (2RS,12bSR) N-(2-methanesulfonamidoethyl)-(2-methylamino-1,3,4,6,7,12b-hexahydro-2H-benzo[b]furo[2,3-a]quinolizin-2-yl)acetamide as a foam.

Step C: Preparation of (2RS,12bSR)-2-(N-(2-methanesulfonamidoethyl)-2-aminoethyl)-2-methylamino-1,3,4,6,7,12b-hexahydro-2H-benzo[b]furo[2,3-a]quinolizine 50 milliliters of dry tetrahydrofuran and 7.20 milliliters (4.94 mmol) of a 3.4M solution of Red-Al in toluene were heated at reflux under an argon atmosphere and a solution of 1.33 grams (3.06 mmol) of (2RS,12bSR) N-(2-methanesulfonamidoethyl)-(2-methylamino-1,3,4,6,7,12b-hexahydro-2H-benzo[b]furo[2,3-a]quinolizin-2-yl)acetamide in 50 ml of THF was added dropwise over 15 minutes. The mixture was maintained at reflux for 2 hours, then cooled to room temperature and the reaction quenched by slow addition of saturated aqueous sodium potassium tartrate solution. This mixture was diluted with ethyl acetate and the layers were separated. The organic phase was washed with brine, dried (Na₂SO₄), filtered and concentrated in vacuo to obtain 1.54 grams of (2RS,12bSR) 2-(N-(2-methanesulfonamidoethyl)-2-aminoethyl)-2-methylamino-1,3,4,6,7,12b-hexahydro-2H-benzo[b]furo[2,3-a]quinolizine.

Step D: Preparation of (2SR,12bSR) 1,3,4,5,6,6', 7,12b-octahydro-1'-(2methanesulfonamidoethyl)-3'-methyl-spiro(2H-benzo[b]furo[2,3-a]quinolizin)-2,4'-(1'H-pyrimidin-2'-(3'H)-one)

1.20 grams (2.85 mmol) of (2RS,12bSR) 2-(N-(2-methanesulfonamidoethyl)-2-aminoethyl)-2-methylamino-1,3,4,6,7,12b-hexahydro-2H-benzo[b]furo[2,3-a]quinolizine, 100 milliliters of dry methylene chloride, and 4.0 milliliters (49.46 mmol) of pyridine were stirred together then cooled to 0° C. and 3.49 ml (4.28 mmol) of a 12% w/w solution of phosgene in toluene was added dropwise over 15 minutes. The reaction mixture was stirred at 0° C. for an additional 30 minutes and was then quenched by addition of aqueous sodium bicarbonate solution. The layers were separated and the aqueous phase was extracted with chloroform. The organic fractions were combined and dried over Na₂SO₄. The dried solution was filtered, the solvent removed in vacuo and the residue chromatographed on 60 grams of silica gel using 1% methanol in ammonia saturated chloroform as eluant to obtain 306 mg of (2SR,12bSR) 1,3,4,5',6,6', 7,12b-octahydro-1'-(2-methanesulfonamidoethyl)-3'-methyl-spiro-(2H-benzo[b]furo[2,3-a]quinolizin-2,4'-(1'H-pyrimidin-2'-(3'H)-one) free base. The HCl salt was prepared from ethanolic hydrogen chloride and was recrystallized from boiling ethyl acetate-methanol, m.p.: 210°–215° C. with decomposition.

EXAMPLE XVII (2RS,13bSR) 1,3,4,5',6,6',7,13b-octahydro-3'-(2-methanesulfonamidoethyl)-spiro-(2H-naphthaleno[2,1-a]quinolizin)-2,4'-(1'H-pyrimidin-2'-(3'H)-one In a manner similar to that described for Example XII, 4.24 grams (16.87 mmol) of (13bSR) 1,3,4,6,7,13b-hexahydronaphthaleno[2,1-a]quinolizin-2-one was converted into 0.40 gram of (2RS,13bSR) 1,3,4,5',6,6',7,13b-octahydro-3'-(2-methanesulfonamidoethyl)-spiro-(2H-naphthaleno[2,1-a]quinolizin)-2,4'-

(1'H-pyrimidin-2'-(3'H)-one hydrochloride, m.p. 190° C.

EXAMPLE XVIII (2RS,1,3,4,5',6,6',7,13b-octahydro-3'-(2-sulfamidoethyl)-spiro-(2H-naphthaleno[2,1-a]quinolizin)-2,4'-(1'H-pyrimidin-2'-(3'H)-one)

In a manner similar to that described for Example XIII, 4.24 grams (16.87 mmol) of (13bSR) 1,3,4,6,7,13b-hexahydronaphthaleno[2,1-a]quinolizin-2-one was converted into 1.30 grams of (2RS,13bSR) 1,2,4,5',6,6',7,13b-octahydro-3'-(2-sulfamidoethyl)-spiro-(2H-naphthaleno[2,1-a]quinolizin)-2,4'-(1'H-pyrimidin-2'-(3'H)-one) free base, m.p. 241° C. with decomposition.

EXAMPLE XIX (2RS,12bSR) 1,3,4,5',6,6',7,12b-octahydro-3'-(2-sulfamidoethyl)-spiro-(2H-benzo[b]thieno[2,3-a]quiniolizin)-2,4'-(1'H-pyrimidin-2'-(3'H)-one In a manner similar to that described for Example XIII, 463 grams (19.03 mmol) of (12bSR) 1,3,4,6,7,12b-hexahydrobenzo[b]thieno[2,3-a]quinolizin-2-one was converted into 0.23 gram of (2RS,12bSR) 1,3,4,5',6,6',7,12b-octahydro-3'-(2-sulfamidoethyl)-spiro-(2H-benzo[b]thieno[2,3-a]quinolizin)-2,4'-(1'H-pyrimidin-2'-(3'H)-one)hydrochloride, m.p. 235°–237° C.

EXAMPLE XX (2RS,12bSR) 1,3,4,5',6,6',7,12b-octahydro-3'-(2-methanesulfonamidoethyl)-spiro-(2H-benzo[b]thieno [2,3-a]quinolizin)-2,4'-(1'H-pyrimidin-2'-(3'H)-one)

In a manner similar to that described for Example XII 1.69 grams (6.96 mmol) of (12bSR) 1,3,4,6,7,12b-hexahydrobenzo[b]thieno[2,3-a]quinolizin-2-one was converted into 0.16 gram of (2RS,12bSR) 1,3,4,5',6,6',7,12b-octahydro-3'-(2-methanesulfonamidoethyl)spiro-(2H-benzo[b]thieno[2,3-a]quinolizin)-2,4'-(1'H-pyrimidin-2'-(3'H)-one) hydrochloride, m.p. 171°–174° C.

EXAMPLE XXI (2R,12bS) 1,3,4,5',6,6',7,12b-octahydro-3'-(2-sulfamidoethyl)-spiro-(2H-benzo[b]furo[2,3-a]quinolizin-2,4'-(1'H-pyrimidin-2'-(3'H)-one)

In a manner similar to that described for Example XIII, 2.10 grams (8.71 mmol) of (12bS) 1,3,4,6,7,12b-hexahydrobenzo[b]furo[2,3-a]quinolizin-2-one was converted into 1.25 gram of (2R,12bS) 1,3,4,5',6,6',7,12b-octahydro-3'-(2-sulfamidoethyl)-spiro-(2H-benzo[b]furo[2,3-a] quinolizin)-2,4'-(1'H-pyrimidin-2'-(3'H)-one) hydrochloride, m.p. 193°–195° C. with decomposition.

EXAMPLE XXII (2R,12bS)-1,3,4,5',6,6',7,12b-octahydro-3'-(N'-methyl-2-sulfamidoethyl-spiro-(2H-benzo[b]furo[2,3-a]quinolizin)-2,4'-(1'H-pyrimidin-2'-(3'H)-one)

Step A: Preparation of (2R,12bS) 1,3,4,5', 6,6',7,12b-octahydro-3'-(N-tert-butyl-2-sulfamidoethyl)-spiro-(2H-benzo[b]furo[2,3-a]quinolizin)-2,4'-(1'H-pyrimidin-2'-(3'H)-one)

In a manner similar to that described for Example XIII, 6.20 grams (25.70 mmol) of (12bS) 1,3,4,6,7,12b-hexahydrobenzo[b]furo[2,3-a]quinolizin-2-one was converted into 5.9 grams of (2R,12bS) 1,3,4,5',6,6',7,12b-octahydro-3'-(N'-tert-butyl-2-sulfamidoethyl)-spiro-(2H-benzo[b]furo[2,3-a]quinolizin)-2,4'-(1'H-pyrimidin-2'-(3'H)-one).

Step B: Preparation of (2R,12bS) 1,3,4,5',6, 6',7,12b-octahydro-3'-(N'-tert-butyl-N-benzyloxy methyl-2-sulfamidoethyl)-spiro-(2H-benzo[b]furo[2,3-a]quinolizin)-2,4'-(1'H-pyrimidin-2'-(3'H)-one)

1.35 milliliters (3.37 mmol) of a 2.5 M solution of n-butyllithium in hexane was added under nitrogen to a stirred and cooled to 0° C. solution of 1.13 grams (2.31 mmol) of (2R,12bS) 1,3,4,5',6,6',7,12b-octahydro-3'(N'-tert-butyl-2-sulfamidoethyl)-spiro-(2H-benzo[b]furo[2,3-a]quinolizin)-2,4'-(1'H-pyrimidin-2'-(3'H)-one on 50 milliliters of dry tetrahydrofuran. After stirring for 10 minutes, 0.576 gram (3.68 mmol) of chloromethyl benzyl ether in 5 milliliters of dry tetrahydrofuran was added dropwise over 3 minutes. The resulting mixture was stirred for 1 hour at 0° C. followed by 1 hour at 25° C. and then was quenched by the addition of ice. The tetrahydrofuran was removed in vacuo and the aqueous residue was extracted with methylene chloride. The organic fractions were combined, washed with brine, dried ($Na_2SO_4$), filtered and concentrated in vacuo. The residue was chromatographed on silica gel using 3% methanol in ammonia saturated chloroform as eluant to obtain from the eluate 0.80 gram of (2R,12bS) 1,3,4,5',6,6',7,12b-octahydro-3'-(N'-tert-butyl-N-benzyloxy methyl-2-sulfamidoethyl)-spiro-(2H-benzo[b]furo[2,3-a]quinolizin)-2,4'-(1'H-pyrimidin-2'-(3'H)-one) free base.

Step C: Preparation of (2R,12bS) 1,3,4,5',6, 6',7,12b-octahydro-3'-(N'-methyl-N'-tertbutyl-N-benzyloxymethyl-2-sulfamidoethyl)-spiro-(2H-benzo[b]furo[2,3a]quinolizin)-2,4'-(1'H-pyrimidin-2'-(3'H-one)

0.336 gram (0.551 mmol) of (2R,12bS) 1,3,4,5,6,6',7,12b-octahydro-3'-(N'-tert-butyl-N-benzyloxy methyl-2-sulfamidoethyl)-spiro-(2H-benzo[b]furo[2,3-a]quinolizin)-2,4'-(1'H-pyrimidin-2'-(3'H)-one) and 10 milliliters of dry THF was cooled to 0° C. and 0.330 milliliters (0.826 mmol) of a 2.5 M solution of n-butyllithium in hexane was added thereto. After 15 minutes stirring 0.195 gram (1.38 mmol) of iodomethane was added. The ice bath then was allowed to expire and the mixture stirred overnight. The reaction was quenched by the addition of ice. The THF was removed in vacuo and the aqueous residue was extracted with methylene chloride. The organic fractions were combined, washed with brine, dried ($Na_2SO_4$), filtered and concentrated in vacuo. The residue was chromatographed on silica gel using 4% methanol in chloroform as eluant and to obtain from the eluate 0.168 gram of (2R,12bS) 1,3,4,5',6,6',7, 12b-octahydro-3'-(N'-methyl- N'-tert-butyl-N-benzyloxymethyl-2-sulfamidoethyl)-spiro-(2H-benzo[b]furo[2,3-a]quinolizin)-2,4'-(1'-H-pyrimidin-2'-(3'H-one) free base.

Step D: Preparation of (2R,12bS) 1,3,4,5',6,6',7,12b-octahydro-3'-(N'-methyl-2-sulfamidoethyl)-spiro-(2H-benzo[b]furo[2,3-a]quinolizin)-2,4'-(1'H-pyrimidin-2'-(3'H)-one 0.168 gram (0.269 mmol) of (2R,12bS) 1,3,4,5',6,6',7,12b-octahydro-3'-(N'-methyl-N'-tert-butyl-(N-benzyloxymethyl)-2-sulfamidoethyl)-spiro-(2H-benzo[b]furo[2,3-a]quinolizin)-2,4'-(1'-H-pyrimidin-2'-(3'H-one), 9 milliliters of ethylene glycol dimethyl ether and 6 milliliters of 6 N HCl. After stirring 18 hours at 25° C. the reaction mixture was poured into ice. The aqueous solution was made basic with concentrated ammonium hydroxide and was extracted into methylene chloride. The organic fractions were combined, washed with brine, dried (Na₂SO₄), filtered and concentrated in vacuo. The residue was chromatographed on silica gel using 4% methanol in ammonia saturated chloroform as eluant to obtain from the eluate as residue, 0.0844 gram of (2R,12bS) 1,3,4,5',6,6',7,12b-octahydro-3'-(N'-methyl-2-sulfamidoethyl)spiro-(2H-benzo[b]furo[2,3-a]quinolizin)-2,4'-(1'H-pyrimidin-2'-(3'H)-one free base. The HCl salt was prepared from ethanolic HCl and methylene chloride. The HCl salt had a melting point of 175°–178° C. with decomposition. The specific rotation for the HCl salt was −28.3°, c=.00090 g/ml, methanol.

EXAMPLE XXIII (2R,12bS) 1,3,4,5',6,6',7,12b-octahydro-3'-(N-methyl-2-sulfamidoethyl)-spiro-(2H-benzo[b]furo[2,3-a]quindizin)-2,4'-(1'H-pyrimidin-2'-(3'H)-one) and (2R,12bS) 1,3,4,5',6,6',7,12b-octahydro-3'-(N',N-dimethyl)-2-sulfamidoethyl)-spiro-(2H-benzo[b]furo[2,3-a]quinolizin)-2,4'-(1'H-pyrimidin-2'-(3'H)-one)

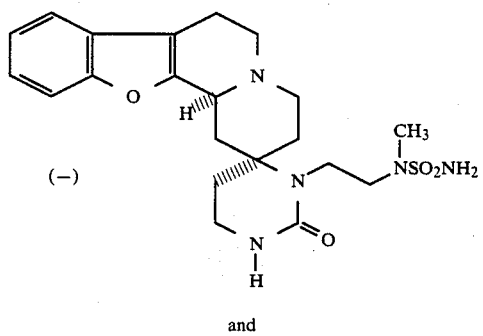

and

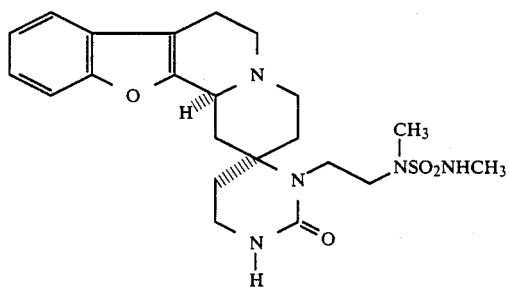

Step A: Preparation of (2R,12bS) 1,3,4,5',6,6',7,12b-octahydro-3'-(N'-tert-butyl-N-methyl-2-sulfamidoethyl)-spiro-(2H-benzo[b]furo[2,3-a]quinolizin)-2,4'-(1'-H-pyrimidin-2'-(3'-H)-one) and (2R,12bS) 1,3,4,5',6,6',7,12b-octahydro-3'-(N'-methyl-N'-tert-butyl-N-methyl-2-sulfamidoethyl)-spiro-(2H-benzo[b]furo[2,3-a]quinolizin)-2,4'-(1'-H-pyrimidin-2'-(3'-H)-one)

A solution of 1.24 grams (2.53 mmol) of (2R,12bS) 1,3,4,5',6,6',7,12b-octahydro-3'-(N'-tertbutyl-2-sulfamidoethyl-spiro-(2H-benzo[b]furo[2,3-a]quinolizin-2-4'-(1'-H-pyrinidin-2'-(3'H)-one) in 70 milliliters of dry tetrahydrofuran under nitrogen was cooled to 0° C. and 1.67 milliliters (4.18 mmol) of a 2.5M solution of n-butyllithium in hexane was added while stirring. After 10 minutes of stirring after completion of the addition, 0.718 gram (5.06 mmol) of iodomethane was added, the ice bath was allowed to expire and the mixture was stirred for 4 hours. Then, an additional 0.718 gram (5.06 mmol) of iodomethane was added and the stirring continued for 18 hours at 25° C. The reaction was quenched by the addition of ice. The tetrahydrofuran was removed in vacuo and the aqueous reside was extracted with methylene chloride. The organic fractions were combined, washed with brine, dried (Na₂SO₄), filtered, and concentrated in vacuo. The residue was chromatographed on silica gel using ammonia saturated chloroform as eluant to recover from the eluate 0.25 gram of (2R,12bS) 1,3,4-5',6,6',7,12b-octahydro-3'-(N-methyl-N'-tert-butyl-2-sulfamindoethyl)-spiro-(2H-benzo[b]furo[2,3-a]quinolizin) -2,4'-(1'-H-pyrimidin-2'-(3'H)-one) and 0.60 gram of (2R,12bS) 1,3,4,5',6,6',7,12b-octahydro-3'-(N,N-dimethyl-N'-tert-butyl-(2-sulfamidoethyl)-spiro-(2H-benzo[b]furo[2,3-a]quinolizin)-2,4'-(1'-H-pyrimidin-2'-(3'-H-one), both as free bases.

Step B: Preparation of (2R,12bS) 1,3,4,5',6,6',7,12b-octahydro-3'-(N-methyl-2-sulfamidoethyl)spiro-(2H-benzo[b]furo[2,3-a]quinolizin)-2,4'-(1'-H-pyrimidin-2'-(3'H)-one)

A solution of 0.250 grams (.495 mmol) of (2R,12bS) 1,3,4,5',6,6',7,12b-octahydro-3'-(N'-tertbutyl-N-methyl-2-sulfamidoethyl)-spiro-(2H-benzo[b]furo[2,3-a]quinolizin)-2-4'-(1'-H-pyrimidin-2'-(3'-H)-one and 8 milliliters of trifluoroacetic acid were stirred together under nitrogen for 18 hours at 25° C. The reaction mixture then was poured into ice and the aqueous solution made basic with concentrated ammonium hydroxide. The basic solution was extracted into methylene chloride. The organic fractions were combined, washed with brine, dried (Na₂SO₄), filtered and concentrated in vacuo. The residue was chromatographed on silica gel using 5% methanol in ammonia saturated chloroform as eluant to obtain in the eluate 0.121 gram of (2R,12bS) 1,3,4,5',6,6',7,12b-octahydro-3'-(N-methyl-2-sulfamidoethyl)-spiro-(2H-benzo[b]furo[2,3-a]quinolizin)-2,4'-(1'-H-pyrimidin-2'-(3'H)-one free base. The HCl salt was prepared by contacting the base with ethanolic HCl in methylene chloride. The HCl salt had m.p. of 241°–243° C. The specific rotation for the HCl salt was −43.3°, c=.00090 g/ml, methanol.

Step C: Preparation of (2R,12bS) 1,3,4,5',6,6',7,12b-octahydro-3'-(N',N-dimethyl-2-sulfamidoethyl)-spiro-(2H-benzo[b]furo[2,3-a]quinolizin)-2,4'-(1'-H-pyrmidin-2'-(3'H)-one)

0.500 gram (0.966 mmol) of (2R,12bS) 1,3,4,5',6,6',7,12b-octahydro-3'-(N',N-dimethyl-N'-tert-butyl)-2-sulfamidoethyl)-spiro-(2H-benzo[b]furo[2,3-a]quinolizin)-2,4'-(1'-H-pyrimidin-2'-(3'H)-one and 10 milliliters of trifluoroacetic acid were stirred together for 1.5 hours at 25° C. and then poured onto ice. The aqueous solution was made basic with concentrated ammonium hydroxide and was extracted into methylene chloride. The organic fractions were combined, washed with brine, dried (Na2SO4), filtered and concentrated in vacuo. The residue was chromatographed on silica gel using 5% methanol in ammonia saturated choroform as eluant to obtain in the eluate 0.42 gram of (2R,12bS) 1,3,4,5',6,6',7,12b-octahydro-3'-(N',N-dimethyl-2-sulfamidoethyl)-spiro-(2H-benzo[b]furo[2,3-a]quinolizin)-2,4'-(1'-H-pyrimidin-2'(3'H)-one) free base. The HCl salt was prepared by mixing the base with ethanolic hydrogen chloride in methylene chloride. The salt had a melting point of 150°-153° C. with decomposition. The specific rotation for the HCl salt was —43.6°, c=.00275 g/ml. methanol.

EXAMPLE XXIV (2R,12bS)-1,3,4,6,7,12b-hexahydro-3'-(2-(N-methylmethanesulfamidoethyl)-spiro-(2H-benzo[b]furo(2,3-a)quinolizine)-2,4'-(imidazolidin-2'-one) monohydrochloride

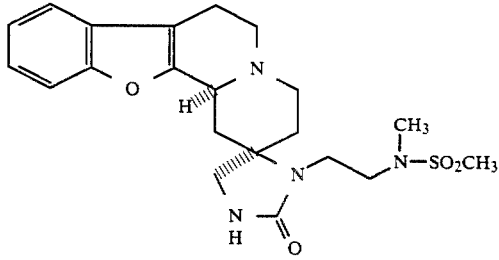

A solution of 2.36M n-butyllithium (0.36 ml, 0.84 mmol) was added to a cold (0° C.) solution of 320 mg (0.776 mmol) of (2R,12bS)-1,3,4,6,7,12b-hexahydro-3'-(2-methanesulfonamidoethyl)-spiro-(2H-benzo[b]furo-(2,3-a)quinolizine-2,4'-imidazolidin-2'-one) in 50 milliliters of tetrahydrofuran. After 10 minutes, idomethane (120 mg, 0.766 mmol) was added and the reaction stirred at 0° C. for 1 hour and at room temperature for an additional 18 hours. At the end of this time, it was diluted with water, concentrated and washed with methylene chloride. The organic layer was dried, filtered and concentrated to obtain a crude product which was chromatographed (SiO2, 2% MeOH/NH3 saturated chloroform) to yield 172 milligrams of product from which an hydrochloride salt mp=>300° C. (dec.) was generated in a manner similar to that previously described.

EXAMPLE XXV (2RS,12bSR) 1,3,4,6,7,12b-hexahydro-1'-(2-(N-methylmethanesulfonamido)ethyl)-3'-methyl-spiro(2H-benzo[b]furo[2,3-a]quinolizin)-2,4'-(imidazolidin-2'-one)

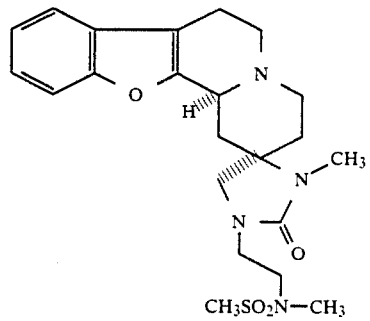

Step A: Preparation of (2S,12bSR)-1,3,4,6,7,12b-hexahydro-1'-(2-(N-methyl-methanesulfonamidoethyl)-3'-methyl-spiro(2H-benzo[b]furo[2,3-a]quinolizin)-2,4'-(imidazolidine-2'-one)

To a heterogeneous mixture of 20 milliliters of toluene and 20 milliliters of 40% sodium hydroxide was added 0.05 gram (0.116 mmol) of (2RS,12bSR)-1,3,4,6,7,12b-hexahydro-1'-(2-methanesulfomamidoethyl)-3'-methyl-spiro(2H-benzo[b]furo[2,3-a]quinolizin-2,4'-(imidazolidine-2'-one), 0.025 gram (0.17 mmol) of methyl iodide and 0.06 gram (0.17 mmol) of tetrabutylammonium hydrogen sulfate. The resulting mixture was stirred very reapidly for 18 hours after which time the layers were separated and the aqueous layer extracted twice with 10 milliliters of toluene. The organic solutions were combined and washed with three 10 milliliter portions of water and one 15 milliliter portion of saturated sodium chloride solution. The washed solution was dried (Na2SO4) and the solvent vaporized to obtain crude (2RS,12bSR)-1,3,4,6,7,12b-hexahydro-1'-(2-(N-methyl-methanesulfonamido)ethyl)-3'-methyl-spiro(2H-benzo[b]furo[2,3-a]quinolizin)-2,4'-(imidazolidine-2'-one) as a yellow oil. This was purified by spinning disc chromatography (chloroform saturated with ammonia) to obtain 0.036 gram (0.08 mmol, 70%) of the product which was dissolved in ethyl acetate and ethanolic HCl added thereto to obtain 0.023 gram (2RS,12bSR)-1,3,4,5,6,7,12b-hexahydro-1'-(2-(N-methyl-methanesulfonamido)ethyl)-3'-methylspiro(2H-benzo-[b]furo[2,3-a]quinolizin)-2,4'-(imidazolidine-2'-one)-hydrochloride as a white crystalline solid, m.p. 164°-167° C. (from ethyl acetate/methanol).

EXAMPLE XXVI (2R,12bS)-1,3,4,5',6,6',7,12b-octanhydro-3'-(2-methanesulfonamidoethyl)-spiro-(2H-benzo[b]-thieno[2,3-a]quinolizin)-2,4'-(1'-H-pyrimidin-2'(3'H)-one)

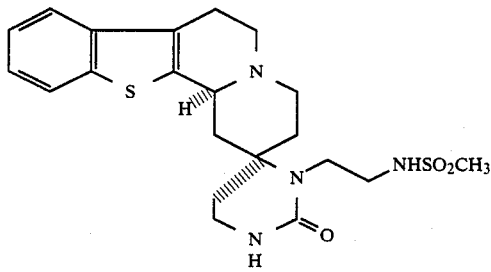

Step A. Resolution of (12bSR)-1,3,4,6,7,12b-hexahydrobenzo[b]thieno[2,3-a]quinolizin-2-one A solution of 7.9 grams of (−)-di-p-toluoyl-L-tartaric acid monohydrate in 44 ml of ethyl acetate was mixed with a solution of 5.0 grams of (12bSR)-1,3,4,6,7,12b-hexahydrobenzo[b]thieno[2,3-a]quinolizin-2-one (prepared as described in Tetrahedron Letters, 1985, 26, 1277) in 265 ml of ethyl acetate and the mixture stirred for 18 hours. The mixture was filtered to obtain 4.7 g of the di-p-toluoyl-L-tartrate salt of the amine. This salt was stirred in 280 milliliters of boiling ethyl acetate (one-half of which being ethyl acetate previously saturated with water) for two hours then stirred for 12 hours at ambient temperature to obtain a solid precipitate. The latter was collected by suction filtration and then partitioned between ethyl acetate and saturated aqueous $Na_2CO_3$. The ethyl acetate solution was separated, washed with brine, dried ($Na_2SO_4$) and treated with charcoal. The mixture was filtered and concentrated to dryness to obtain 0.7 gram (14%) of (12bS)-1,3,4,6,7,12b-hexahydrobenzo[b]thieno[2,3-a]quinolizin-2-one, m.p. 111°–113° C.; $[\alpha]_D$ −99.8°, (c=8.8 mg/ml, $CHCl_3$).

Anal. for $C_{15}H_{15}NOS$: Calc'd: C, 70.01; H, 5.88; N, 5.44; Found: C, 69.84; H, 5.85; N, 5.36.

Step B: Preparation of (E,Z)-2-Cyanomethylidene-1,3,4,6,7,12b-hexahydrobenzo[b]thieno[2,3-a]quinolizine A NaH dispersion in mineral oil (0.336 g, 8.16 mmol) under argon was washed twice with hexane to remove the oil and replaced with 20 ml of dry tetrahydrofuran (THF). The resulting suspension was stirred and cooled to 0° C. and 1.32 ml (8.16 mmol) of diethylcyanomethylphosphonate in 5 ml of THF was added dropwise therein. After this solution had been stirred at 0° C. for 0.5 hour, a solution of (12bS)-1,3,4,6,7,12b-hexahydrobenzo[b]thieno[2,3-a]quinolizin-2-one (0.7 g, 2.72 mmol) in THF (20 ml) was added dropwise. After stirring for 2 hours at 25° C., ice water was added to the reaction mixture, and the mixture extracted with two 100 ml portions of ethyl acetate. The organic layers were combined, washed with four 100 ml portions of water, then with brine and thereafter dried ($Na_2SO_4$). The dried solution was filtered and concentrated to dryness to obtain 0.76 g (100%) of (E,Z)-2-cyanomethylidene-1,3,4,6,7,12b-hexahydrobenzo[b]thieno[2,3-a]quinolizine.

Anal. for $C_{17}H_{16}N_2OS$: Calc'd: C, 72.82; H, 5.75; N, 9.99; Found: C, 72.71; H, 5.73; N, 9.90.

Step C: Preparation of (2R,12bS)-2-Aminoethylamino-2-cyanomethyl-1,3,4,6,7,12b-hexahydrobenzo[b]thieno[2,3-a]quinolizine 0.76 gram (2.72 mmol) of (E,Z)-2-cyanomethylidene-1,3,4,6,7,12b-hexahydrobenzo[b]thieno[2,3-a]quinolizine and 10 milliliters (0.15 mol) of ethylenediamine were stirred in 60 ml of absolute ethanol under argon at 65° C. for 5 days, then concentrated to dryness. The residue was partitioned between methylene chloride and water. The organic layer was washed with two 100 ml portions of water, then brine and thereafter dried ($Na_2SO_4$). The dried solution was filtered, concentrated to dryness and then flash chromatographed on a silica gel column, eluting with chloroform saturated with ammonia:methanol, 95:5 to obtain 0.6 g (66%) of (2R, 12bS)-2-aminoethylamino-2-cyanomethyl-1,3,4,6,7,12b-hexahydrobenzo[b]thieno[2,3-a]quinolizine.

Anal. for $C_{19}H_{24}S \cdot \frac{1}{4}CH_3OH$: Calc'd: C, 66.34; H, 7.23; N, 16.08; Found: C, 66.28; H, 7.20; N, 16.18.

Step D: Preparation of (2R, 12bS)-2-cyanomethyl-2-methanesulfonamidoethylamino-1,3,4,6,7,12b-hexahydrobenzo[b]thieno[2,3-a]quinolizine A mixture of 0.6 gram (1.76 mmol) of (2R,12bS)-2-aminoethylamino-2-cyanomethyl-1,3,4,6,7,12b-hexahydrobenzo[b]thieno[2,3-a]quinolizine, 0.73 gram (5.28 mmol) of anhydrous potassium carbonate and 0.54 g (3.52 mmol) of methanesulfonic anhydride was stirred vigorously in 50 milliliters of chloroform and 50 milliliters of water under argon for 6 hours. The chloroform layer was separated, washed with two 50 ml portions of water, then brine and thereafter dried ($Na_2SO_4$). The dried solution was filtered and concentrated to dryness to obtain 0.74 g (100% yield) of (2R,12bS)-2-cyanomethyl-methanesulfonamidoethylamino-1,3,4,6,7,12b-hexahydrobenzo[b]thieno[2,3-a]quinolizine.

Step E: Preparation of (2R,12bS)-2-aminoethyl-2-methanesulfonamidoethylamino-1,3,4,6,7,12b-hexahydrobenzo[b]thieno[2,3-a]quinolizine 0.24 gram (6.27 mmol) of lithium aluminum hydride was suspended in 50 milliliters of dry diethyl ether with magnetic stirring at 0° C. in an ice-water bath under argon. A solution of 0.74 gram (1.79 mmol) of (2R,12bS)-2-cyanomethyl-2-methylsulfonamidoethylamino-1,3,4,6,7,12b-hexahydrobenzo[b]thieno[2,3-a]quinolizine in 10 milliliters of dry tetrahydrofuran was added dropwise and the mixture was stirred for 18 hours at 25° C. The reaction mixture was cooled to 0° C. and decomposed with 50 ml of saturated aqueous sodium potassium tartrate solution, the ether layer separated and the aqueous layer washed with three 50 ml portions of chloroform, the ether and chloroform layers combined, washed with $H_2O$, brine and dried ($Na_2SO_4$) to obtain 0.55 g (73%) of (2R,12bS)-2-aminoethyl-2-methanesulfonamidoethylamino-1,3,4,6,7,12b-hexahydrobenzo[b]thieno[2,3-a]quinolizine. The product, after flash chromatography on a silica gel column eluting with CHCl₃ saturated with ammonia:methanol, 95:5 had [α]$_D$ −64.2° (2.2 mg/ml, CHCl₃).

Anal. for $C_{20}H_{30}N_4O_2S_2 \cdot \frac{3}{4}H_2O$: Calc'd: C, 55.08; H, 7.28; N, 12.85; Found: C, 55.22; H, 6.99; N, 12.87.

Step F: Preparation of (2R,12bS)-1,3,4,5',6,6',7,12b-octahydro-3'-(2-methanesulfonamidoethyl)spiro-(2H-benzo[b]-thieno[2,3-a]quinolizine,2,4'-(1'H-pyrimidin-2'(3H)-one)

A solution of 0.16 gram (0.38 mmol) of (2R,12bS)-2-aminoethyl-2-methanesulfonamidoethylamino-1,3,4,6,7,12b-hexahydrobenzo[b]thieno[2,3-a]quinolizine in 40 milliliters of dry tetrahydrofuran under nitrogen was cooled to −78° C. in a dry ice acetone bath. n-Butyl lithium (2.5M in hexane; 337 microliters (μl), 0.84 mmol) was added with stirring. The reaction mixture was allowed to warm to 25° C. over 15 minutes then cooled back down to −78° C. 2.18 microliters (0.42 mmol) of phosgene (1.93M in toluene) was added via a syringe. After stirring at −78° C., for 1-2 hours the reaction mixture was brought to 25° C., quenched with saturated NaHCO₃ solution to pH 8, the THF removed in vacuo and the residue extracted with three 20 milliliter portions of methylene chloride. The organic layers were combined, washed with brine and dried (Na₂SO₄), filtered and concentrated to obtain 0.16 gram (81%) of (2R,12bS)-1,3,4,5',6,6',7,12b-octahydro-3'-(2-methanesulfonamidoethyl)-spiro (2H-benzo[b]-thieno[2,3-a]quinolizine-2,4'-(1'H-pyrimidin-2'(3'H)-one. After chromatography on silica gel eluting with CHCl₃ saturated with ammonia:methanol, 97:3, the product was converted to the hydrochloride salt, m.p. 171°–174° C.

Anal. for $C_{21}H_{28}N_4O_3S_2 \cdot HCl$: Calc'd: C, 52.00; H, 6.03; N, 11.55; Found: C, 52.36; H, 5.83; N, 11.65.

Preparation of Starting Materials

The following preparation of (12bSR)-1,3,4,6,7,12b-hexahydrobenzo[b]furo[2,3-a]-quinolizin-2-one more fully described in aforecited copending applications of Baldwin et al., is representative of the preparation of quinolizin-2-one starting materials of Formula (VI).

Step A: Preparation of 3-Cyanomethylbenzo[b]furan

To a suspension of 2.64 grams (0.11 mole) of oil free sodium hydride in 200 milliliters of tetrahydrofuran (THF) was added dropwise a solution of 19.47 grams (0.11 mole) of diethyl cyanomethylphosphonate in 75 milliliters of THF. After the H₂ evolution had ceased, a solution of 13.4 grams (0.1 mole) of 3-(2H)-benzo[b]-furanone in 100 milliliters of THF was added. The solution was heated at 70° C. for 1.5 hours, cooled, and poured into 500 milliliters of 5% HCl, and worked up using conventional procedures and finally distilled at 96°–100° C./0.075 mm Hg to obtain a yellow oil product which crystallized upon standing.

Step B: Preparation of 2-(3-benzo[b]furanyl)ethylamine

A solution of 3.97 grams (0.025 mole) of 3-cyanomethylbenzo[b]furan in 200 milliliters of diethyl ether was slowly added to a refluxing suspension of 3.84 grams (0.1 mole) of lithium aluminum hydride in 400 milliliters of ether and the mixture was heated 3 hours, then cooled and water was slowly added. The suspension was filtered and the filtrate was evaporated to obtain an oily product, the hydrochloride salt of which has m.p. 183°–185° C.

Step C: Preparation of 3-(2-formamidoethyl)benzo[b]furan

A solution of 2.35 grams (0.015 mole) of 2-(3-benzo[b]furanyl)ethylamine and 5 milliliters of ethyl formate was heated at 60° C. for 3 hours, poured into 2N HCl extracted with methylene chloride, the latter washed with 5% sodium hydroxide, dried, filtered and concentrated to obtain the product.

Step D: Preparation of 3,4-dihydrobenzo[b]furo[2,3-c]pyridine 2.28 grams (0.012 mole) of 3-(2-formamidoethyl)benzo[b]furan was added to 28 grams of polyphosphoric acid which was preheated to 100° C. After 1–1.5 hours, the reaction mixture was poured onto ice and the residues were washed with water. The polyphosphoric acid was dissolved in water, filtered, the filtrate made basic with concentrated ammonia to obtain a precipitate product, m.p. 170°–171° C.

Step E: Preparation of (12bSR)-1,3,4,6,7,12b-Hexahydrobenzo[b]furo[2,3-a]quinolizin-2-one To a solution of 12 grams (0.070 mol) of 3,4-dihydrobenzo[b]furo[2,3-c]pyridine dissolved in 500 milliliters of acetonitrile at 60° C. was added 20 grams (0.140 mol) of 2-trimethylsiloxy-1,3-butadiene followed by 13.6 grams (0.10 mol) of anhydrous zinc chloride. The mixture was heated at 60° C. for 1.5 hours, cooled to 25° C. and 30 milliliters of 5% HCl was added and stirred 10 minutes. 40% Sodium hydroxide was added until the reaction was basic; 200 milliliters of water was added; and the acetonitrile layer was separated. The aqueous layer was filtered and washed with ether. The combined organic layers were dried, filtered, and concentrated and the residue chromatographed (silica, ethyl acetate/hexane (1:1)) to obtain (12b,SR)-1,3,4,6,7,12b-hexahydrobenzo[b]furo[2,3-a]quinolizin-2-one product, m.p. 108°–109° C.

If desired the quinolizinone product may be resolved employing (−)-di-p-toluoyl-L-tartaric acid monohydrate or (+)-di-p-toluoyl-D-tartaric acid monohydrate in a manner similar to that described in the aforementioned Baldwin applications.

What is claimed:

1. A hexahydroarylquinolizine compound of the formula

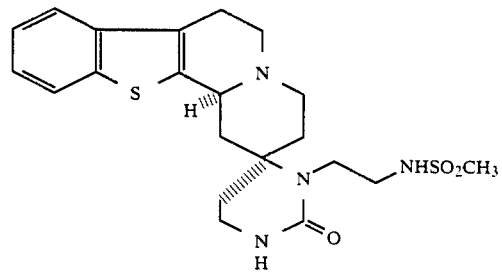

or a pharmaceutically acceptable salt thereof.

2. A compound according to claim 1 which is (2b,12bS)-1,3,4,5',6,6',7,12b-octahydro-3'-(2-methanesulfonamidoethyl)-spiro (2H-benzo[b]-thieno[2,3-a]quinolizin-2,4'-(1'H-pyrimidin-2'(3'H)-one), (2S,12bR)-1,3,4,5',6,6',7,12b-octahydro-3'-(2-methanesulfonamidoethyl)spiro (2H-benzo[b]thieno[2,3-a]quinolizin-2,4'-(1'H-pyrimidin-2'(3'H)-one) or a mixture thereof.

* * * * *